(12) United States Patent
Bower et al.

(10) Patent No.: US 11,304,657 B2
(45) Date of Patent: Apr. 19, 2022

(54) COGNITIVE PLATFORM COUPLED WITH A PHYSIOLOGICAL COMPONENT

(71) Applicant: Akili Interactive Labs, Inc., Boston, MA (US)

(72) Inventors: Jeffrey Bower, Norwood, MA (US); Titiimaea Alailima, Cambridge, MA (US); Jason Johnson, Novato, CA (US); Walter Edward Martucci, Westwood, MA (US); Isabella Slaby, Boston, MA (US); Matthew Omernick, Larkspur, CA (US); Adam Piper, Sebastopol, CA (US); Paul Rand Pierce, Seattle, WA (US); Ashley Mateus, Cambridge, MA (US); Scott Kellogg, Mattapoisett, MA (US)

(73) Assignee: Akili Interactive Labs, Inc., Boston, MA (US)

( * ) Notice: Subject to any disclaimer, the term of this patent is extended or adjusted under 35 U.S.C. 154(b) by 568 days.

(21) Appl. No.: 16/327,144

(22) PCT Filed: Aug. 25, 2017

(86) PCT No.: PCT/US2017/048698
§ 371 (c)(1),
(2) Date: Feb. 21, 2019

(87) PCT Pub. No.: WO2018/039610
PCT Pub. Date: Mar. 1, 2018

(65) Prior Publication Data
US 2019/0216392 A1    Jul. 18, 2019

Related U.S. Application Data

(63) Continuation-in-part of application No. PCT/US2017/042938, filed on Jul. 19, 2017.
(Continued)

(51) Int. Cl.
*A61B 5/00*    (2006.01)
*A61B 5/0533*    (2021.01)
(Continued)

(52) U.S. Cl.
CPC .......... *A61B 5/4884* (2013.01); *A61B 5/0533* (2013.01); *A61B 5/162* (2013.01);
(Continued)

(58) Field of Classification Search
CPC . A61B 2562/0219; A61B 5/021; A61B 5/024; A61B 5/0533; A61B 5/162;
(Continued)

(56) References Cited

U.S. PATENT DOCUMENTS 6,585,518 B1    7/2003    Jenkins et al.
8,016,416 B1    9/2011    Straus
(Continued)

FOREIGN PATENT DOCUMENTS

EP    2031572 A2    3/2009
JP    2006503359 A    1/2006
(Continued)

OTHER PUBLICATIONS

Gerson et al., "Cortical origins of response time variability during rapid discrimination of visual objects." Neuroimage, vol. 28, No. 2, pp. 342-353. 2005. Elsevier, Amsterdam, NL.
(Continued)

*Primary Examiner* — Jonathan T Kuo
(74) *Attorney, Agent, or Firm* — Gregory Finch; Finch Paolino, LLC

(57) ABSTRACT

Example systems, methods, and apparatus, including cognitive platforms, are provided for computing performance metrics of an individual based at least in part on user interaction(s) with computerized tasks and/or interference and at least one physiological measure of the individual,
(Continued)

where the performance metric provides an indication of the cognitive abilities of the individual. The apparatus can be coupled to at least one physiological component to perform the physiological measurement of the individual. The apparatus also can be configured to adapt the tasks and/or interferences to enhance the individual's cognitive abilities.

33 Claims, 24 Drawing Sheets

Related U.S. Application Data

(60) Provisional application No. 62/380,116, filed on Aug. 26, 2016.

(51) Int. Cl.
| | |
|---|---|
| A61B 5/16 | (2006.01) |
| G16H 50/20 | (2018.01) |
| G16H 30/40 | (2018.01) |
| G16H 20/30 | (2018.01) |
| G16H 50/50 | (2018.01) |
| G16H 40/63 | (2018.01) |
| G16H 20/70 | (2018.01) |
| A61B 5/369 | (2021.01) |
| A61B 5/021 | (2006.01) |
| A61B 5/024 | (2006.01) |
| G09B 5/00 | (2006.01) |
| G09B 7/00 | (2006.01) |
| G16H 50/00 | (2018.01) |
| G06N 20/00 | (2019.01) |

(52) U.S. Cl.
CPC .............. *A61B 5/168* (2013.01); *A61B 5/369* (2021.01); *A61B 5/4076* (2013.01); *A61B 5/4088* (2013.01); *A61B 5/7267* (2013.01); *G16H 20/30* (2018.01); *G16H 20/70* (2018.01); *G16H 30/40* (2018.01); *G16H 40/63* (2018.01); *G16H 50/20* (2018.01); *G16H 50/50* (2018.01); *A61B 5/021* (2013.01); *A61B 5/024* (2013.01); *A61B 2562/0219* (2013.01); *G06N 20/00* (2019.01); *G09B 5/00* (2013.01); *G09B 7/00* (2013.01); *G16H 50/00* (2018.01)

(58) Field of Classification Search
CPC ......... A61B 5/163; A61B 5/168; A61B 5/369; A61B 5/4076; A61B 5/4088; A61B 5/4884; A61B 5/7267; G06N 20/00; G09B 5/00; G09B 7/00; G16H 20/30; G16H 20/70; G16H 30/40; G16H 40/63; G16H 50/20; G16H 50/50; G16H 50/00–50/80
See application file for complete search history.

(56) References Cited

U.S. PATENT DOCUMENTS

| | | | |
|---|---|---|---|
| 8,343,012 B2 | 1/2013 | Redmann | |
| 9,265,458 B2 | 2/2016 | Stack | |
| 9,302,179 B1 | 4/2016 | Merzenich et al. | |
| 9,566,029 B2 | 2/2017 | Faubert et al. | |
| 9,940,844 B2* | 4/2018 | Gazzaley | A61B 5/162 |
| 2004/0175683 A1 | 9/2004 | Duffy et al. | |
| 2005/0175972 A1 | 8/2005 | Goldman et al. | |
| 2005/0199010 A1 | 9/2005 | Coleman et al. | |
| 2006/0089335 A1 | 4/2006 | Liu et al. | |
| 2007/0141541 A1 | 6/2007 | Chan et al. | |
| 2007/0299319 A1 | 12/2007 | Chan et al. | |
| 2008/0028276 A1 | 1/2008 | Li et al. | |
| 2008/0280276 A1 | 11/2008 | Raber et al. | |
| 2009/0031217 A1 | 1/2009 | Tysbo | |
| 2009/0312817 A1 | 12/2009 | Hogle et al. | |
| 2010/0092929 A1 | 4/2010 | Hallowell et al. | |
| 2010/0094155 A1 | 4/2010 | Prichep | |
| 2010/0152249 A1 | 6/2010 | Rasgon | |
| 2010/0292545 A1 | 11/2010 | Berka et al. | |
| 2011/0005532 A1 | 1/2011 | Faubert et al. | |
| 2012/0059229 A1 | 3/2012 | Faubert et al. | |
| 2012/0077160 A1 | 3/2012 | DeGutis et al. | |
| 2012/0088222 A1 | 4/2012 | Considine et al. | |
| 2012/0090446 A1 | 4/2012 | Moreno | |
| 2012/0108997 A1 | 5/2012 | Guan et al. | |
| 2012/0196257 A1 | 8/2012 | Verghese et al. | |
| 2012/0208169 A1 | 8/2012 | Nutley et al. | |
| 2012/0214143 A1 | 8/2012 | Severson et al. | |
| 2012/0258436 A1 | 10/2012 | Lee | |
| 2012/0271194 A1 | 10/2012 | MacLullich et al. | |
| 2013/0091453 A1 | 4/2013 | Kotler et al. | |
| 2013/0344000 A1 | 12/2013 | Kaplin et al. | |
| 2014/0019059 A1 | 1/2014 | Shankle et al. | |
| 2014/0107494 A1 | 4/2014 | Kato et al. | |
| 2014/0279746 A1 | 9/2014 | De Bruin et al. | |
| 2014/0315169 A1 | 10/2014 | Bohbot | |
| 2014/0323013 A1 | 10/2014 | Gonzalez-Heydrich et al. | |
| 2014/0370479 A1* | 12/2014 | Gazzaley | A61B 5/4884 |
| | | | 434/322 |
| 2015/0004577 A1 | 1/2015 | Wu et al. | |
| 2015/0024357 A1 | 1/2015 | Faubert et al. | |
| 2015/0112899 A1 | 4/2015 | Dagum | |
| 2015/0187227 A1 | 7/2015 | Zhang et al. | |
| 2015/0199010 A1 | 7/2015 | Coleman et al. | |
| 2015/0248470 A1 | 9/2015 | Coleman et al. | |
| 2016/0078780 A1 | 3/2016 | Alexander et al. | |
| 2016/0125748 A1 | 5/2016 | Ashford | |
| 2016/0155355 A1 | 6/2016 | Merzenich et al. | |
| 2016/0262680 A1 | 9/2016 | Martucci et al. | |
| 2016/0310059 A1 | 10/2016 | Faubert et al. | |
| 2016/0351069 A1 | 12/2016 | Faubert et al. | |
| 2017/0007147 A1 | 1/2017 | Hasegawa | |
| 2017/0098385 A1* | 4/2017 | Martucci | A61B 5/4848 |
| 2019/0159716 A1 | 5/2019 | Alailima et al. | |
| 2020/0060603 A1 | 2/2020 | Bower et al. | |
| 2020/0174557 A1 | 6/2020 | Alailima et al. | |
| 2020/0380882 A1 | 12/2020 | Alailima et al. | |

FOREIGN PATENT DOCUMENTS

| | | |
|---|---|---|
| JP | 2006-227850 | 8/2006 |
| JP | 2009-285000 A | 12/2009 |
| JP | 2011-150408 A | 8/2011 |
| JP | 2014-508309 A | 3/2014 |
| JP | 2014508309 A | 4/2014 |
| WO | WO-2004036499 A1 | 4/2004 |
| WO | 2012064999 A1 | 5/2012 |
| WO | WO-2012064999 A1 | 5/2012 |
| WO | 2012165602 | 12/2012 |
| WO | WO-2014138925 A1 | 9/2014 |
| WO | WO-2015049234 A1 | 4/2015 |
| WO | 2015111331 A1 | 7/2015 |
| WO | 2015177908 A1 | 11/2015 |
| WO | WO-2015179522 A1 | 11/2015 |
| WO | WO-2015192021 A1 | 12/2015 |
| WO | 2016049234 A1 | 3/2016 |
| WO | 2016065013 | 4/2016 |
| WO | 2018081134 A1 | 9/2019 |

OTHER PUBLICATIONS

Extended European Search Report, Application No. EP 17844519.3. dated Dec. 3, 2019. European Patent Office, Munich, DE.
Anguera, et al., "Video game training enhances cognitive control in older adults," Nature, (Sep. 2013), vol. 501. 36 pages.
Annex to European Patent Office Communication dated Sep. 19, 2018, for Application No. 15795907.3, 5 pg.
Australian Examination Report No. 1 dated Nov. 26, 2018 for Application No. 2015264260, 3 pages.

(56) References Cited

OTHER PUBLICATIONS

Baniqued, et al., "Selling Points: What Cognitive Abilities are Tapped by Casual Video Games?," Acta psycholgica, (2013), vol. 142, No. 1, pp. 74-86.
Caron, "Gaming & Culture—Of gyroscopes and gaming: the tech behind the Wii MotionPlus," Aug. 26, 2008, https://arstechnica.com/gaming/2008/08/wii-motion-sensor/, pp. 1-8.
Charron, et al., Divided Representation of Concurrent Goals in the Human Frontal Lobes, Science, (Apr. 2010), vol. 328, No. 5975, pp. 360-363.
Colich, et al., "Neural Aspects of Inhibition Following Emotional Primes in Depressed Adolescents," J Clin Child Adolesc Psychol., (2016), vol. 45, No. 1, pp. 21-30.
Communication Pursuant to Article 94(3) dated Sep. 19, 2018, for Application No. 15795907.3, 2 pg.
Communication Pursuant to Rule 161(2) and 162 dated Jan. 4, 2017, for Application No. 15795907.3, 2 pg.
Communication Pursuant to Rule 161(2) and 162 dated Feb. 28, 2019, for Application No. 17831833.3, 3 pg.
Communication Pursuant to Rule 161(2) and 162 dated Mar. 12, 2019, for Application No. 17837724.8, 3 pg.
International Search Report and Written Opinion dated Nov. 28, 2018, for Application No. PCT/US2018/00179, 18 pg.
Extended European Search Report dated Oct. 11, 2018, for Application No. 16762544.9, 11 pg.
Hastie, et al., The Elements of Statistical Learning, 2nd Edition, Springer (2009), 44 pages.
International Preliminary Report on Patentability dated Nov. 22, 2016 for International Application No. PCT/US2015/031780 (14 pages).
International Search Report and Written Opinion dated Aug. 19, 2015 for International Application No. PCT/US2015/031780 (12 pages).
International Search Report and Written Opinion dated Dec. 4, 2018 for International Application No. PCT/US2018/045206 (19 pages).
International Search Report and Written Opinion dated Nov. 7, 2017 for International Application No. PCT/US2017/048698 (30 pages).
International Search Report and Written Opinion dated Oct. 13, 2017 for International Application No. PCT/US2017/045385 (30 pages).
International Search Report and Written Opinion dated Sep. 29, 2017 for International Application No. PCT/US2017/042938 (21 pages).
International Search Report and Written Opinion dated Dec. 28, 2017 for International Application No. PCT/US2017/058103. 18 pages.
International Search Report and Written Opinion dated Mar. 7, 2018 for International Application No. PCT/US2017/66214. 13 pages.
International Search Report and Written Opinion dated Mar. 29, 2018 for International Application No. PCT/US2018/13182. 12 pages.
Japanese Notice of Reasons for Rejection dated Dec. 7, 2018, for Application No. 2017-513600, 5 page.
Junco, et al. "Perceived Academic Effects of Instant Messaging Use," Computers & Education, (2011), vol. 56, pp. 370-378.
Kautz, et al., "Fostering and Measuring Skills: Improving Cognitive and Non-Cognitive Skills to Promote Lifetime Success," National Bureau of Economic Research, (Sep. 2007), 87 pages.
Laricchiuta, et al., Individual differences in response to positive and negative stimuli: endocannabinoid-based insight on approach and avoidance behaviors, Frontiers in Systems Neuroscience, (Dec. 2014), vol. 8, Article 238, 22 pages.
Mayer, et al., "Nine Ways to Reduce Cognitive Load in Multimedia Learning," Education Psychologist, (2003), vol. 38, No. 1, pp. 43-52.
Pashler, "Dual-Task Interference in Simple Tasks: Data and Theory," Psychological Bulletin, (1994), vol. 116, No. 2, pp. 220-244.
Written Opinion dated May 26, 2016, for Application No. PCT/US2016/022115, 13 pg.
Compass, "Psilocybin therapy Background and Key findings from prior published studies," Compass Pathways Powerpoint presentation, (2018), 11 pages.
Compass, Transforming mental health through psychoactive care pathways, Compass Pathways Powerpoint presentation, (Jan. 2018), 19 pages.
Rucker, et al., "Psychedelics in the treatment of unipolar mood disorders: a systematic review," Journal of Psychopharmacology, (2016), pp. 1-10.
Examination Report, Australian application No. 2017314831. dated Oct. 5, 2021. IP Australia, Phillip, AU.
Office Action, Japanese application No. 2019-511612. English translation. dated Jun. 14, 2021. Japan Patent Office, Tokyo, JP.
Office Action, European application No. 17844519.3. dated Aug. 11, 2020. European Patent Office, Rijswijk, NL.
Office Action, Korean application No. 10-2019-7008399. English translation. dated Aug. 27, 2021. Korean Intellectual Property Office, Daejeon, Republic of Korea.
Office Action, Japanese application No. 2019-505412. English translation. dated Oct. 4, 2021. Japan Patent Office, Tokyo, JP.

\* cited by examiner

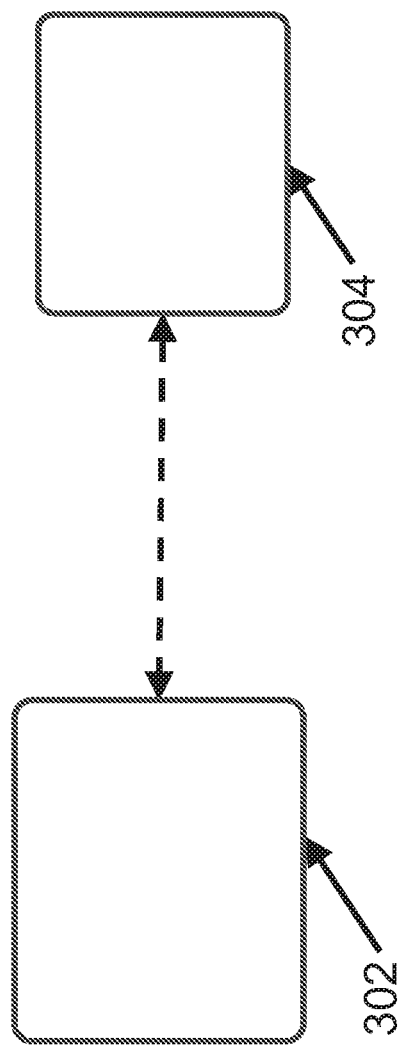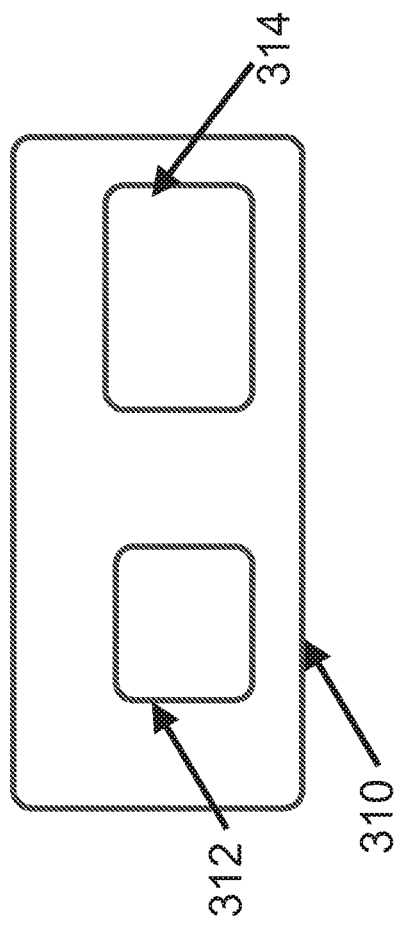
FIG. 3A
FIG. 3B

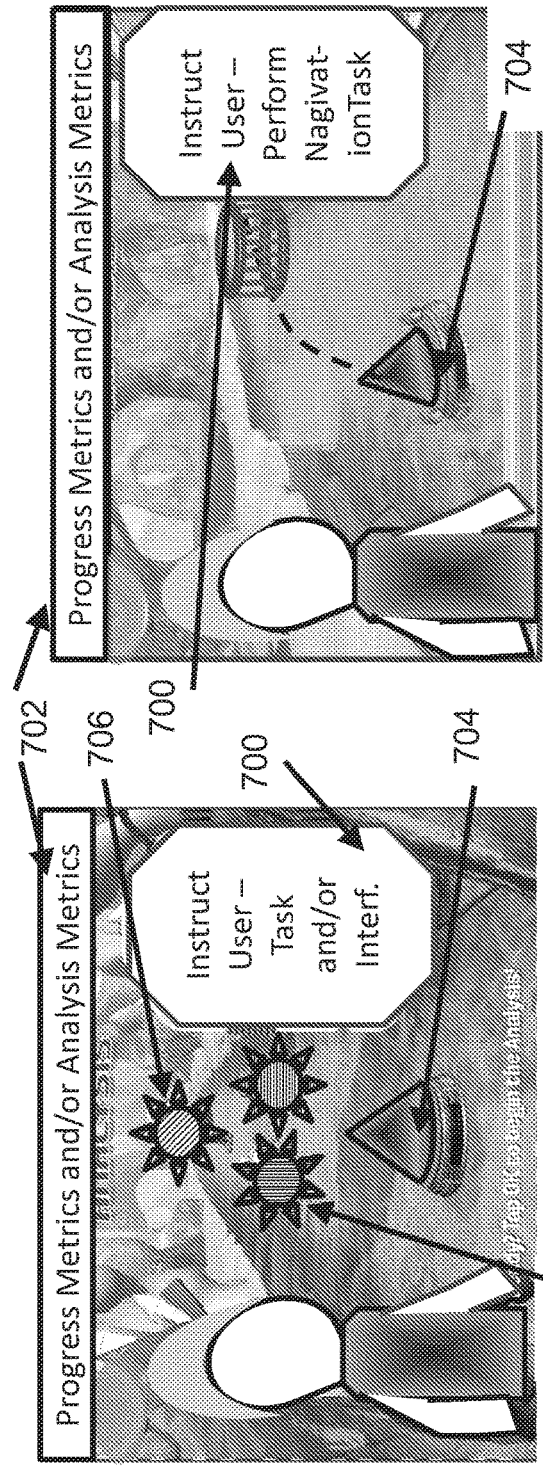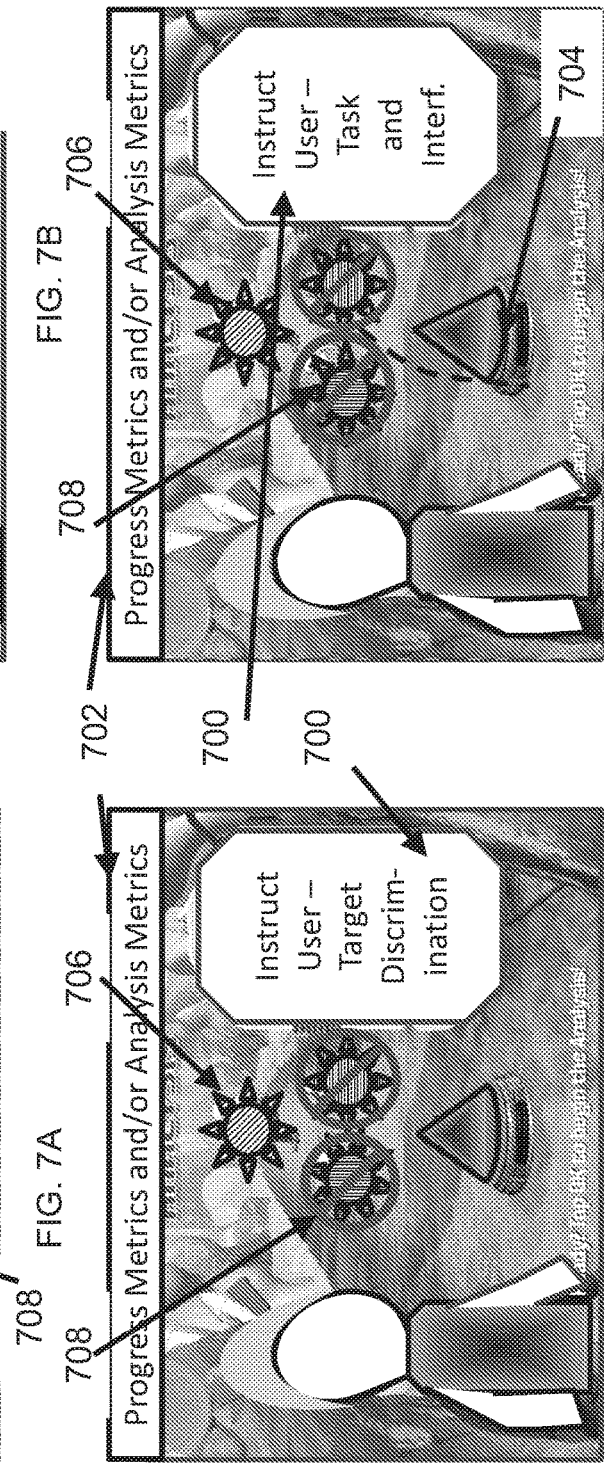
FIG. 7A
FIG. 7B
FIG. 7C
FIG. 7D

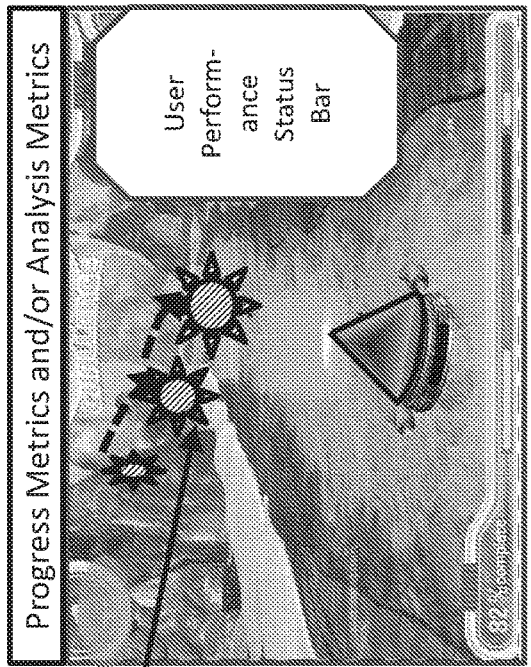
FIG. 8A
FIG. 8B
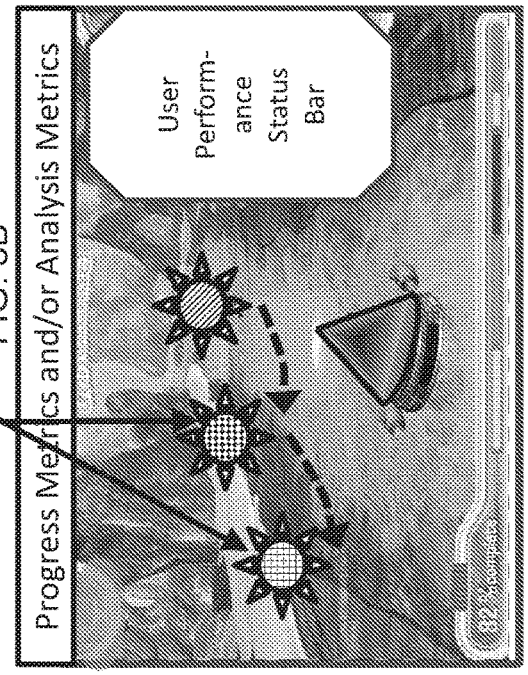
FIG. 8C
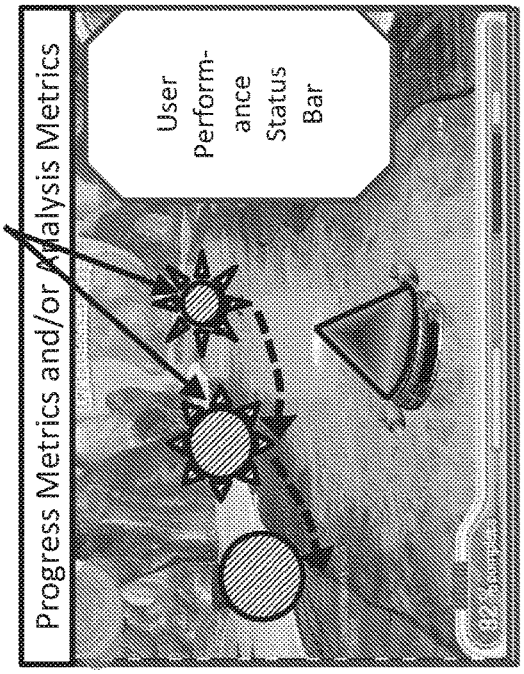
FIG. 8D

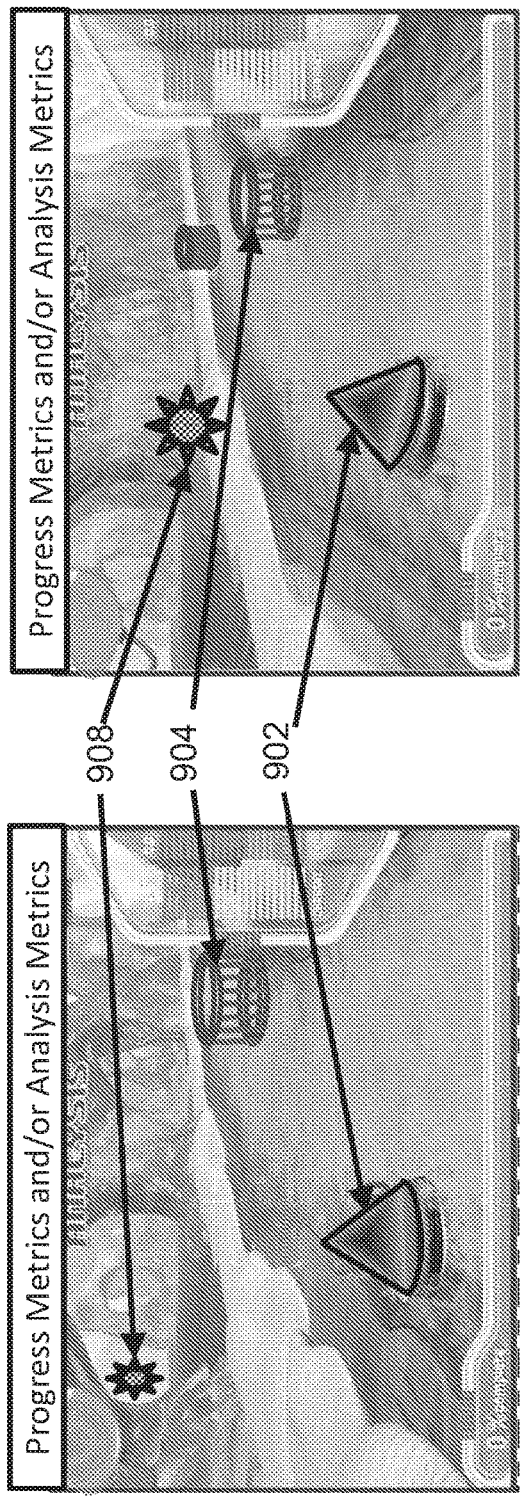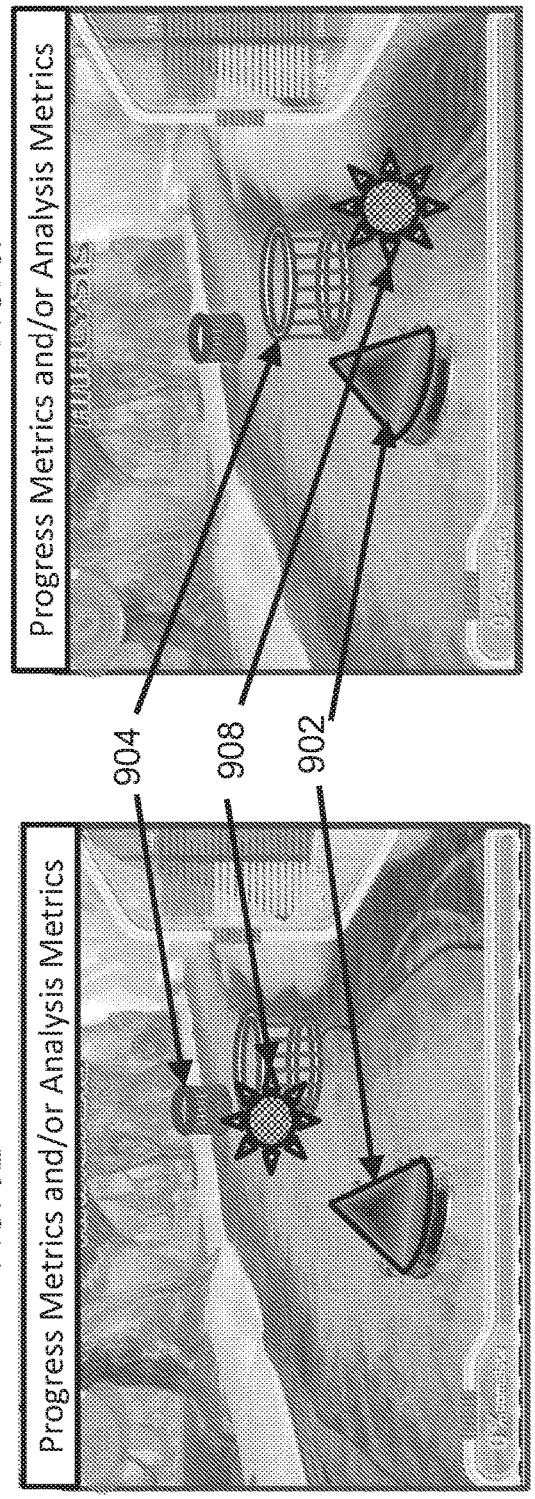
FIG. 9E
FIG. 9F
FIG. 9G
FIG. 9H

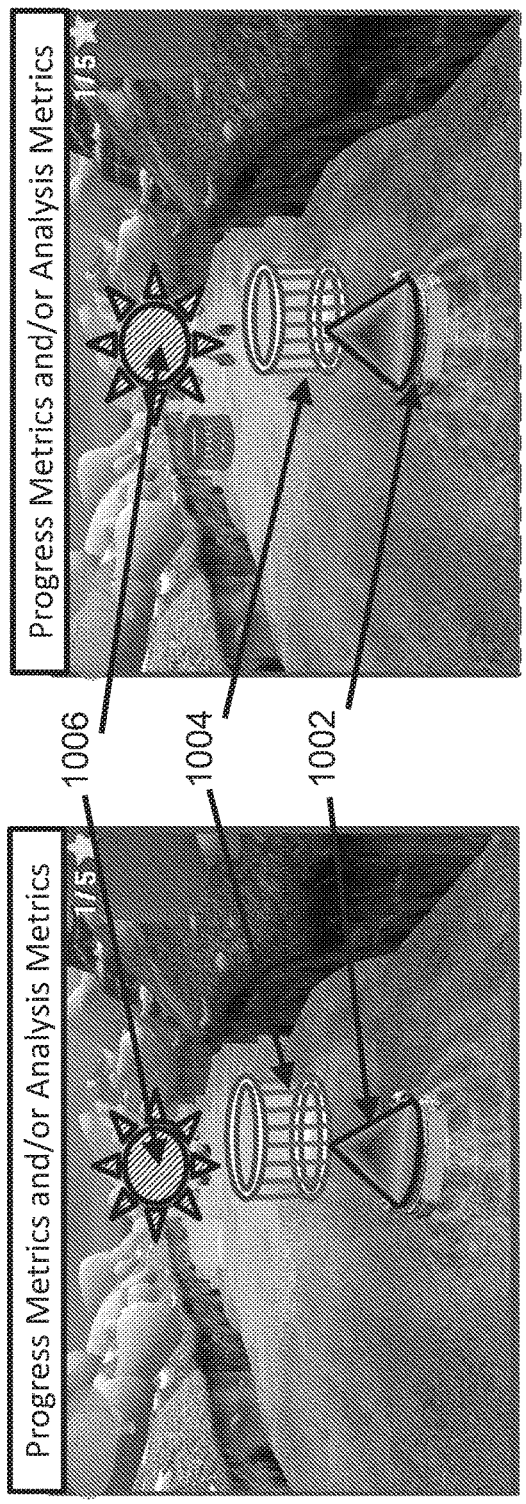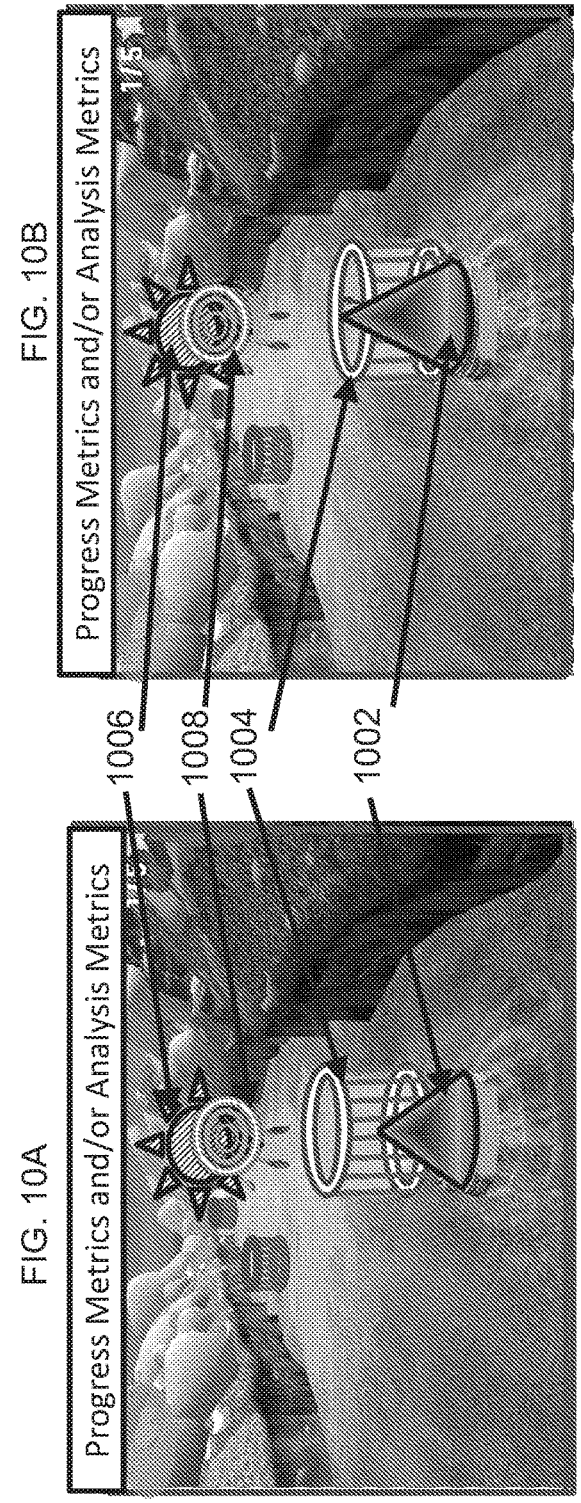

COGNITIVE PLATFORM COUPLED WITH A PHYSIOLOGICAL COMPONENT

CROSS-REFERENCE TO RELATED APPLICATIONS

This application claims priority benefit of international patent application No. PCT/US2017/048698, filed Aug. 26, 2017, which claims priority benefit of U.S. provisional application No. 62/380,116, entitled "COGNITIVE PLATFORM COUPLED WITH A PHYSIOLOGICAL COMPONENT" filed on Aug. 26, 2016, and is a continuation-in-part of U.S. international application No. PCT/US2017/042938, entitled "PLATFORMS TO IMPLEMENT SIGNAL DETECTION METRICS IN ADAPTIVE RESPONSE-DEADLINE PROCEDURES" filed on Jul. 19, 2017, each of which is incorporated herein by reference in its entirety, including drawings.

BACKGROUND OF THE DISCLOSURE

In the normal course of aging, individuals can experience a certain amount of cognitive decline. This can cause an individual to experience increased difficulty in challenging situations, such as time-limited, attention-demanding conditions. In both older and younger individuals, certain cognitive conditions, diseases, or executive function disorders can result in compromised performance at tasks that require attention, memory, motor function, reaction, executive function, decision-making skills, problem-solving skills, language processing, or comprehension.

SUMMARY OF THE DISCLOSURE

In view of the foregoing, apparatus, systems and methods are provided for quantifying aspects of cognition (including cognitive abilities) which takes into account the individual's degree of engagement or attention to a cognitive platform. In certain configurations, the example apparatus, systems and methods can be implemented for enhancing certain cognitive abilities.

The example apparatus, systems and methods cognitive platforms configured to implement software and/or other processor-executable instructions for the purpose of measuring data indicative of a user's performance at one or more tasks, to provide a user performance metric. The example performance metric can be used to derive an assessment of a user's cognitive abilities and/or to measure a user's response to a cognitive treatment, and/or to provide data or other quantitative indicia of a user's physiological condition or cognitive bias. The measurements of physiological condition of the individual can be used to provide an indicator of the user's level of engagement or attention to the cognitive platform.

In a general aspect, an apparatus for generating a quantifier of cognitive skills in an individual is provided. The apparatus includes a user interface; a memory to store processor-executable instructions; and a processing unit communicatively coupled to the user interface and the memory, in which upon execution of the processor-executable instructions by the processing unit, the processing unit is configured to render a first instance of a primary task with an interference at the user interface, requiring a first response from the individual to the first instance of the primary task in the presence of the interference, where the interference comprises one or both of an interruptor or a distraction, and to render a second instance of the primary task without the interference at the user interface, requiring a second response from the individual to the second instance of the primary task. The processing unit is configured to receive a secondary response to the interference at substantially the same time as the processing unit receives the second response; or (ii) receive the secondary response to the interference that is an interruptor at substantially the same time as the processing unit receives the first response and not receive the secondary response to the interference that is a distraction at substantially the same time that processing unit receives the first response. The processing unit is further configured to receive data indicative of at least one physiological profile of the individual, the physiological profile being based on one or more measurements of the at least one physiological component, the at least one physiological component being coupled to measure a physiological measurement of the individual. The processing unit is further configured to receive data indicative of the first response, the second response, and the at least one physiological profile, and analyze the differences in the individual's performance from performing the primary task without interference and with interference at least in part by determining a difference between the data indicative of the first response and the data indicative of the second response relative to the at least one physiological profile to determine a performance metric of the individual, the performance metric comprising an indicator of the cognitive ability of the individual.

In another general aspect, a computer-implemented method for generating a quantifier of cognitive skills in an individual is provided. The method includes rendering a first instance of a primary task with an interference at the user interface, requiring a first response from the individual to the first instance of the primary task in the presence of the interference, where the interference comprises one or both of an interruptor or a distraction, and rendering a second instance of the primary task without the interference at the user interface, requiring a second response from the individual to the second instance of the primary task. To implement the method, a processing unit is configured to receive a secondary response to the interference at substantially the same time as the processing unit receives the second response; or (ii) receive the secondary response to the interference that is an interruptor at substantially the same time as the processing unit receives the first response and not receive the secondary response to the interference that is a distraction at substantially the same time that processing unit receives the first response. To implement the method, the processing unit is further configured to receive data indicative of at least one physiological profile of the individual, the physiological profile being based on one or more measurements of the at least one physiological component, the at least one physiological component being coupled to measure a physiological measurement of the individual. The method includes receiving data indicative of the first response, the second response, and the at least one physiological profile, and analyzing the differences in the individual's performance from performing the primary task without interference and with interference at least in part by determining a difference between the data indicative of the first response and the data indicative of the second response relative to the at least one physiological profile to determine a performance metric of the individual, the performance metric comprising an indicator of the cognitive ability of the individual.

In another general aspect, an apparatus for generating a quantifier of cognitive skills in an individual is provided.

The apparatus includes a user interface; a memory to store processor-executable instructions; and a processing unit communicatively coupled to the user interface and the memory, in which upon execution of the processor-executable instructions by the processing unit, the processing unit is configured to render a first instance of a primary task with an interference at the user interface, requiring a first response from the individual to the first instance of the primary task in the presence of the interference, where the interference comprises one or both of an interruptor or a distraction, and to render a second instance of the primary task without the interference at the user interface, requiring a second response from the individual to the second instance of the primary task. The processing unit is configured to receive a secondary response to the interference at substantially the same time as the processing unit receives the second response; or (ii) receive the secondary response to the interference that is an interruptor at substantially the same time as the processing unit receives the first response and not receive the secondary response to the interference that is a distraction at substantially the same time that processing unit receives the first response. The processing unit is further configured to receive data indicative of at least one physiological profile of the individual, the physiological profile being based on one or more measurements of the at least one physiological component, the at least one physiological component being coupled to measure a physiological measurement of the individual. The processing unit is further configured to receive data indicative of the first response, the second response, and the at least one physiological profile, and analyze the differences in the individual's performance from performing the primary task without interference and with interference at least in part by determining a difference between the data indicative of the first response and the data indicative of the second response relative to the at least one physiological profile to determine a first performance metric of the individual, the first performance metric comprising a first indicator of a cognitive ability of the individual. The processing unit is further configured to adjust a difficulty of one or both of the primary task or the interference based on the at least one physiological profile such that the apparatus renders one or both of a third instance of the primary task or the interference at a second difficulty level, and determine a second performance metric of the individual, the second performance metric comprising a second indicator of the cognitive ability of the individual.

In another general aspect, a computer-implemented method for generating a quantifier of cognitive skills in an individual is provided. The method includes rendering a first instance of a primary task with an interference at the user interface, requiring a first response from the individual to the first instance of the primary task in the presence of the interference, where the interference comprises one or both of an interruptor or a distraction, and rendering a second instance of the primary task without the interference at the user interface, requiring a second response from the individual to the second instance of the primary task. To implement the method, a processing unit is configured to receive a secondary response to the interference at substantially the same time as the processing unit receives the second response; or (ii) receive the secondary response to the interference that is an interruptor at substantially the same time as the processing unit receives the first response and not receive the secondary response to the interference that is a distraction at substantially the same time that processing unit receives the first response. To implement the method, the processing unit is further configured to receive data indicative of at least one physiological profile of the individual, the physiological profile being based on one or more measurements of the at least one physiological component, the at least one physiological component being coupled to measure a physiological measurement of the individual. The method includes receiving data indicative of the first response, the second response, and the at least one physiological profile, and analyzing the differences in the individual's performance from performing the primary task without interference and with interference at least in part by determining a difference between the data indicative of the first response and the data indicative of the second response relative to the at least one physiological profile to determine a first performance metric of the individual, the first performance metric comprising a first indicator of a cognitive ability of the individual. The method includes adjusting a difficulty of one or both of the primary task or the interference based on the at least one physiological profile such that the apparatus renders one or both of a third instance of the primary task or the interference at a second difficulty level, and determining a second performance metric of the individual, the second performance metric comprising a second indicator of the cognitive ability of the individual.

For each apparatus, the processing unit can be further configured to use one or both of the first performance metric or the second performance metric to perform at least one of: (i) changing one or more of an amount, concentration, or dose titration of a pharmaceutical agent, drug, or biologic; (ii) identifying a likelihood of the individual experiencing an adverse event in response to administration of the pharmaceutical agent, drug, or biologic; (iii) identifying a change in cognitive abilities of the individual; (iv) recommending a treatment regimen; or (v) recommending or determining a degree of effectiveness of at least one of a behavioral therapy, counseling, or physical exercise.

Each method can further include, based at least in part on the performance metric (including the first and second performance metrics), generating an output to the user interface indicative of at least one of (i) a change in one or more of the amount, concentration, or dose titration of the pharmaceutical agent, drug, or biologic, (ii) a likelihood of the individual experiencing an adverse event in response to administration of the pharmaceutical agent, drug, or biologic, (iii) identifying a change in the individual's cognitive abilities, (iv) recommending a treatment regimen, or (v) recommending or determining a degree of effectiveness of at least one of a behavioral therapy, counseling, or physical exercise.

The details of one or more of the above aspects and implementations are set forth in the accompanying drawings and the description below. Other features, aspects, and advantages will become apparent from the description, the drawings, and the claims.

BRIEF DESCRIPTION OF DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIGS. 3A-3B show example systems, according to the principles herein.

FIGS. 7A-7D show example user interfaces with instructions to a user that can be rendered to an example user interface, according to the principles herein.

FIGS. 8A-8D show examples of the time-varying features of example objects (targets or non-targets) that can be rendered to an example user interface, according to the principles herein.

FIGS. 10A-10D show examples of the dynamics of tasks and interferences that can be rendered at user interfaces, according to the principles herein.

DETAILED DESCRIPTION

Figure 1:
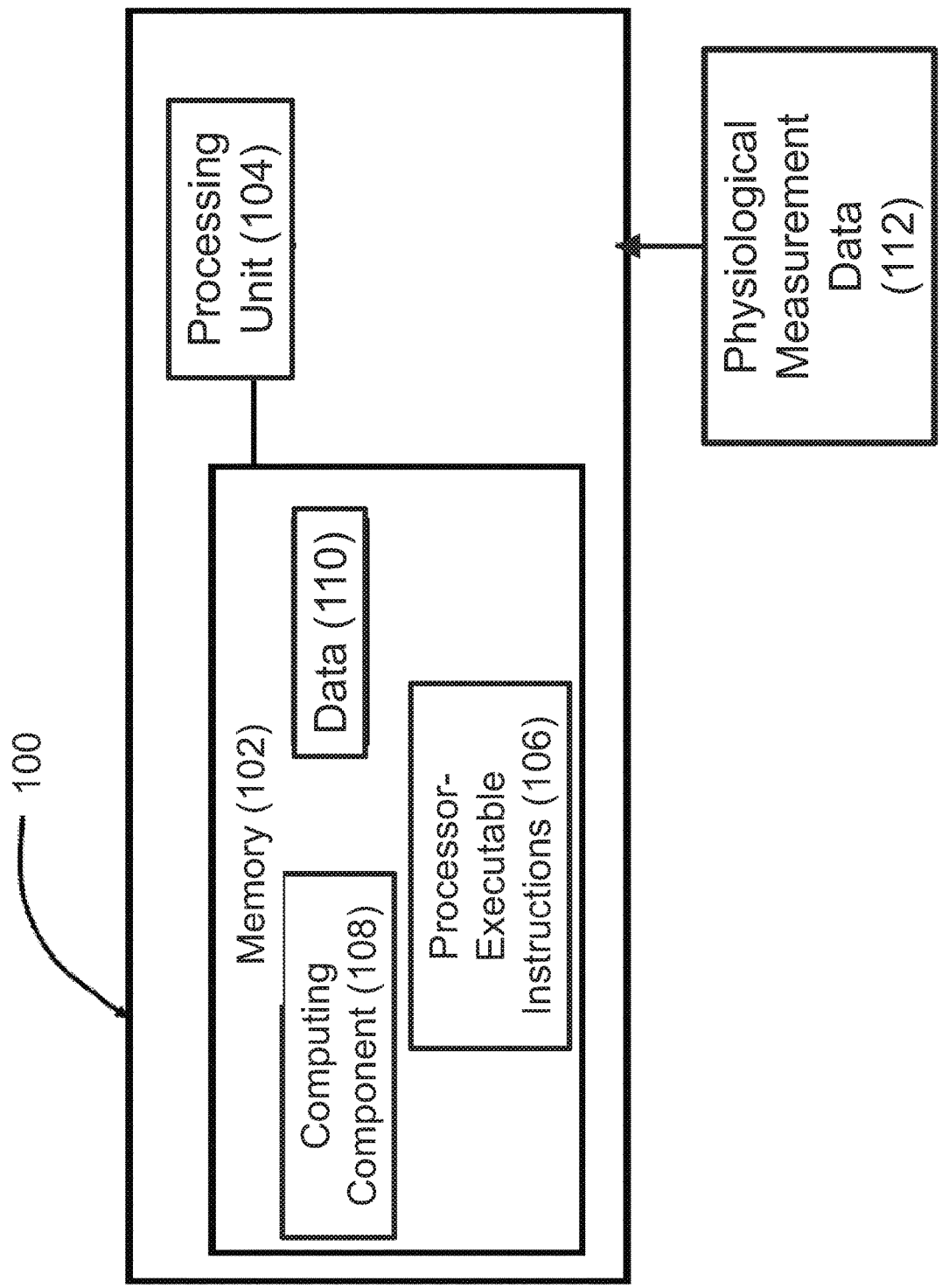
FIG. 1 shows a block diagram of an example apparatus, according to the principles herein.

It should be appreciated that all combinations of the concepts discussed in greater detail below (provided such concepts are not mutually inconsistent) are contemplated as being part of the inventive subject matter disclosed herein. It also should be appreciated that terminology explicitly employed herein that also may appear in any disclosure incorporated by reference should be accorded a meaning most consistent with the particular concepts disclosed herein.

Following below are more detailed descriptions of various concepts related to, and embodiments of, inventive methods, apparatus and systems comprising a cognitive platform configured for coupling with one or more physiological components, and for analyzing data indicative of at least one measurement of the one or more physiological components. As non-limiting examples, the cognitive platform can be configured for cognitive training and/or for clinical purposes. According to the principles herein, the cognitive platform may be integrated with the one or more physiological components.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, the term "including" means including but not limited to. The term "based on" means based at least in part on.

As used herein, the term "target" refers to a type of stimulus that is specified to an individual (e.g., in instructions) to be the focus for an interaction. A target differs from a non-target in at least one characteristic or feature. Two targets may differ from each other by at least one characteristic or feature, but overall are still instructed to an individual as a target, in an example where the individual is instructed/required to make a choice.

As used herein, the term "non-target" refers to a type of stimulus that is not to be the focus for an interaction, whether indicated explicitly or implicitly to the individual.

As used herein, the term "task" refers to a goal and/or objective to be accomplished by an individual. Using the example systems, methods, and apparatus described herein, the computerized task is rendered using programmed computerized components, and the individual is instructed (e.g., using a computing device) as to the intended goal or objective from the individual for performing the computerized task. The task may require the individual to provide or withhold a response to a particular stimulus, using at least one component of the computing device (e.g., one or more sensor components of the computing device). The "task" can be configured as a baseline cognitive function that is being measured.

As used herein, the term "interference" refers to a type of stimulus presented to the individual such that it interferes with the individual's performance of a primary task. In any example herein, an interference is a type of task that is presented/rendered in such a manner that it diverts or interferes with an individual's attention in performing another task (including the primary task). In some examples herein, the interference is configured as a secondary task that is presented simultaneously with a primary task, either over a discrete time period (e.g., a short, discrete time period) or over an extended time period (e.g., less than the time frame over which the primary task is presented), or over the entire period of time of the primary task. In any example herein, the interference can be presented/rendered continuously, or continually (i.e., repeated in a certain frequency, irregularly, or somewhat randomly). For example, the interference can be presented at the end of the primary task or at discrete, interim periods during presentation of the primary task. The degree of interference can be modulated based on the type, amount, and/or temporal length of presentation of the interference relative to the primary task.

As used herein, the term "stimulus" refers to a sensory event configured to evoke a specified functional response from an individual. The degree and type of response can be quantified based on the individual's interactions with a measuring component (including using sensor devices or other measuring components). Non-limiting examples of a stimulus include a navigation path (with an individual being instructed to control an avatar or other processor-rendered guide to navigate the path), or a discrete object, whether a target or a non-target, rendered to a user interface (with an individual being instructed to control a computing component to provide input or other indication relative to the discrete object). In any example herein, the task and/or interference includes a stimulus, which can be a time-varying feature as described hereinbelow.

As used herein, a "trial" includes at least one iteration of rendering of a task and/or interference (either or both with time-varying feature) and at least one receiving of the individual's response(s) to the task and/or interference (either or both with time-varying feature). As non-limiting examples, a trial can include at least a portion of a single-tasking task and/or at least a portion of a multi-tasking task. For example, a trial can be a period of time during a navigation task (including a visuo-motor navigation task) in which the individual's performance is assessed, such as but not limited to, assessing whether or the degree of success to which an individual's actions in interacting with the platform result in a guide (including a computerized avatar) navigating along at least a portion of a certain path or in an environment for a time interval (such as but not limited to, fractions of a second, a second, several seconds, or more) and/or causes the guide (including computerized avatar) to cross (or avoid crossing) performance milestones along the path or in the environment. In another example, a trial can be a period of time during a targeting task in which the individual's performance is assessed, such as but not limited to, assessing whether or the degree of success to which an individual's actions in interacting with the platform result in identification/selection of a target versus a non-target (e.g., red object versus yellow object), or discriminates between two different types of targets. In these examples, the segment of the individual's performance that is designated as a trial for the navigation task does not need to be co-extensive or aligned with the segment of the individual's performance that is designated as a trial for the targeting task.

In any example herein, an object may be rendered as a depiction of a physical object (including a polygonal or other object), a face (human or non-human), or a caricature, other type of object.

In any of the examples herein, instructions can be provided to the individual to specify how the individual is expected to perform the task and/or interference (either or both with time-varying feature) in a trial and/or a session. In non-limiting examples, the instructions can inform the individual of the expected performance of a navigation task (e.g., stay on this path, go to these parts of the environment, cross or avoid certain milestone objects in the path or environment), a targeting task (e.g., describe or show the type of object that is the target object versus the non-target object, or describe or show the type of object that is the target object versus the non-target object, or two different types of target object that the individual is expected to choose between, and/or describe how the individual's performance is to be scored. In examples, the instructions may be provided visually (e.g., based on a rendered user interface) or via sound. In various examples, the instructions may be provided once prior to the performance two or more trials or sessions, or repeated each time prior to the performance of a trial or a session, or some combination thereof.

While some example systems, methods, and apparatus described herein are based on an individual being instructed/ required to decide/select between a target versus a non-target may, in other example implementations, the example systems, methods, and apparatus can be configured such that the individual is instructed/required to decide/choose between two different types of targets (such as but not limited to between two different degrees of a facial expression or other characteristic/feature difference).

In addition, while example systems, methods, and apparatus may be described herein relative to an individual, in other example implementations, the example systems, methods, and apparatus can be configured such that two or more individuals, or members of a group (including a clinical population), perform the tasks and/or interference (either or both with time-varying feature), either individually or concurrently.

The example platform products and cognitive platforms according to the principles described herein can be applicable to many different types of conditions, such as but not limited to social anxiety, depression, bipolar disorder, major depressive disorder, post-traumatic stress disorder, schizophrenia, autism spectrum disorder, attention deficit hyperactivity disorder (encompassing attention deficit disorder), dementia, Parkinson's disease, Huntington's disease, or other neurodegenerative condition, Alzheimer's disease, multiple-sclerosis, or lupus.

As described in greater detail below, the computing device can include an application (an "App program") to perform such functionalities as analyzing the data. For example, the data from the at least one sensor component can be analyzed as described herein by a processor executing the App program on an example computing device to receive (including to measure) substantially simultaneously two or more of: (i) the response from the individual to a task, (ii) a secondary response of the individual to an interference, and (iii) a response of the individual to at least one time-varying feature. As another example, the data from the at least one sensor component can be analyzed as described herein by a processor executing the App program on an example computing device to analyze the data indicative of the first response and the response of the individual to the at least one time-varying feature to compute at least one performance metric comprising at least one quantified indicator of cognitive abilities.

An example system according to the principles herein provides for generating a quantifier of cognitive skills in an individual (including using a machine learning predictive model (such as but not limited to a machine learning classifier)) and/or enhancing cognitive skills in an individual. In an example implementation, the example system employs an App program running on a mobile communication device or other hand-held devices. Non-limiting examples of such mobile communication devices or hand-held device include a smartphone, such as but not limited to an iPhone®, a BlackBerry®, or an Android-based smartphone, a tablet, a slate, an electronic-reader (e-reader), a digital assistant, or other electronic reader or hand-held, portable, or wearable computing device, or any other equivalent device, an Xbox®, a Wii®, or other computing system that can be used to render game-like elements. In some example implementations, the example system can include a head-mounted device, such as smart eyeglasses with built-in displays, a smart goggle with built-in displays, or a smart helmet with built-in displays, and the user can hold a controller or an input device having one or more sensors in which the controller or the input device communicates wirelessly with the head-mounted device. In some example implementations, the computing system may be stationary, such as a desktop computing system that includes a main computer and a desktop display (or a projector display), in which the user provides inputs to the App program using a keyboard, a computer mouse, a joystick, handheld consoles, wristbands, or other wearable devices having sensors that communicate with the main computer using wired or wireless communication. In other examples herein, the example system may be a virtual reality system, an augmented reality system, or a mixed reality system. In examples herein, the sensors can be configured to measure movements of the user's hands, feet, and/or any other part of the body. In some example implementations, the example system can be formed as a virtual reality (VR) system (a simulated environment including as an immersive, interactive 3-D experience for a user), an augmented reality (AR) system (including a live direct or indirect view of a physical, real-world environment whose elements are augmented by computer-generated sensory input such as but not limited to sound, video, graphics and/or GPS data), or a mixed reality (MR) system (also referred to as a hybrid reality which merges the real and virtual worlds to produce new environments and visualizations where physical and digital objects co-exist and interact substantially in real time).

As used herein, the term "predictive model" encompasses models trained and developed based on models providing continuous output values and/or models based on discrete labels. In any example herein, the predictive model encompasses a classifier model.

The instant disclosure is also directed to computer-implemented devices formed as example platform products configured to implement software and/or other processor-executable instructions for the purpose of measuring data indicative of a user's performance at one or more tasks, to provide a user performance metric. The example performance metric can be used to derive an assessment of a user's cognitive abilities and/or to measure a user's response to a cognitive treatment, and/or to provide data or other quantitative indicia of a user's physiological condition or cognitive bias. The measurements of physiological condition may be used to provide an indicator of the user's mood, emotional state, and/or level of engagement or attention to the cognitive platform.

In any example herein, the platform product or cognitive platform can be configured as a medical device platform or other device platform.

The instant disclosure is also directed to example systems that include platform products and cognitive platforms that are configured for coupling with one or more physiological components, as well as example systems where the platform products and cognitive platforms are integrated with one or more physiological components.

In any example herein, the one or more physiological components are configured for performing physiological measurements. The physiological measurements provide quantitative measurement data of physiological parameters and/or data that can be used for visualization of physiological structure and/or functions.

In any example herein, the one or more physiological components can include any means of measuring physical characteristics of the body and nervous system, including electrical activity, heart rate, blood flow, and oxygenation levels. This can include camera-based heart rate detection, measurement of galvanic skin response, blood pressure measurement, electroencephalogram, electrocardiogram, magnetic resonance imaging, near-infrared spectroscopy, and/or pupil dilation measures.

Examples of physiological measurements include, but are not limited to, the measurement of body temperature, heart or other cardiac-related functioning using an electrocardiograph (ECG), electrical activity using an electroencephalogram (EEG), event-related potentials (ERPs), functional magnetic resonance imaging (fMRI), blood pressure, electrical potential at a portion of the skin, galvanic skin response (GSR), magneto-encephalogram (MEG), eye-tracking device or other optical detection device including processing units programmed to determine degree of pupillary dilation, functional near-infrared spectroscopy (fNIRS), and/or positron emission tomography (PET).

The EEG measurements involve the collection of data indicative of the intrinsic electrical activity in the brain, based on the propagation of electric impulses along a nerve fiber in the peripheral nervous system, when groups of neurons in the central nervous system fire in tandem or when groups of neuron in the central nervous system fire synchronously or asynchronously. The EEG can be analyzed in frequency bands that correspond to different mental states. For example, the alpha-frequency (8-13 Hz) can be associated with a relaxed mental state. In an example implementation, data indicative of the small potential changes in the EEG signal can be collected before, during, and/or after a user interacts with the platform product or cognitive platform. This allows the recordation of specific brain responses to specific sensory, cognitive and other mental events. In these examples, the ERP is the measured brain response that is the direct result of a specific sensory, cognitive, and/or motor event or stimulus from the platform product or cognitive platform. The ERPs can provide measurement data for the investigation of psychophysiological states and cognitive information processing.

In some examples herein, the EEG signals herein can be measured independent of individual ERP events.

The fMRI provides measurement data indicative of neuronal activation, based on the difference in magnetic properties of oxygenated versus de-oxygenated blood supply to the brain. The fMRI can provide an indirect measure of neuronal activity by measuring regional changes in blood supply, based on a positive correlation between neuronal activity and brain metabolism.

In an example, simultaneous EEG-fMRI or MEG-fMRI recordings can be made, using magnetic resonance imaging (MRI) compatible EEG/MEG amplifiers (respectively) and electrodes. An EEG-fMRI or MEG-fMRI measurement allows for simultaneous acquisition of electrophysiology (EEG/MEG) data and hemodynamic (fMRI) data.

The TMS involves the excitation of neurons in the brain using weak electric currents that are induced in the tissue by rapidly changing magnetic fields, known as electromagnetic induction. The induced TMS pulse can be applied to interfere with neuronal signaling, causing a temporary neuronal inhibition. TMS allows for localization of cognitive, motor and sensory functions and can play a role in validating other functional imaging methods, such as but not limited to fMRI.

In any example herein, the cognitive platform and systems including the cognitive platform can be configured as an integration of the physiological measurements with computerized tasks and platform interactions that inform cognitive assessment or deliver treatment associated with an example device platform that is implemented using a computing device.

In any example herein, a task can involve one or more activities that a user is required to engage in. Any one or more of the tasks can be computer-implemented as computerized stimuli or interaction (described in greater detail below). For a targeting task, the cognitive platform may require temporally-specific and/or position-specific responses from a user. For a navigation task, the cognitive platform may require position-specific and/or motion-specific responses from the user. For a facial expression recognition or object recognition task, the cognitive platform may require temporally-specific and/or position-specific responses from the user. The multi-tasking tasks can include any combination of two or more tasks. In non-limiting examples, the user response to tasks, such as but not limited to targeting and/or navigation and/or facial expression recognition or object recognition task(s), can be recorded using an input device of the cognitive platform. Non-limiting examples of such input devices can include a touch, swipe or other gesture relative to a user interface or image capture device (such as but not limited to a touch-screen or other pressure sensitive screen, or a camera), including any form of user interface configured for recording a user interaction. In other non-limiting examples, the user response recorded using the cognitive platform for tasks, such as but not limited to targeting and/or navigation and/or facial expression recognition or object recognition task(s), can include user actions that cause changes in a position, orientation, or movement of a computing device including the cognitive platform. Such changes in a position, orientation, or movement of a computing device can be recorded using an input device disposed in or otherwise coupled to the computing device, such as but not limited to a sensor. Non-limiting examples of sensors include a motion sensor, position sensor, and/or an image capture device (such as but not limited to a camera). In an example implementation involving multi-tasking tasks, the computer device is configured (such as using at least one specially-programmed processing unit) to cause the cognitive platform to present to a user two or more different type of tasks, such as but not limited to, targeting and/or navigation and/or facial expression recognition or object recognition tasks, during a short time frame (including in real-time and/or substantially simultaneously). The computer device is also configured (such as using at least one specially-programmed processing unit) to collect data indicative of the type of user response received to the multi-tasking tasks, within the short time frame (including in real-time and/or substantially simultaneously). In these examples, the two or more different types of tasks can be presented to the individual within the short time frame (including in real-time and/or substantially simultaneously), and the computing device can be configured to receive data indicative of the user response(s) relative to the two or more different types of tasks within the short time frame (including in real-time and/or substantially simultaneously).

In some examples, the short time frame can be of any time interval at a resolution of up to about 1.0 millisecond or greater. The time intervals can be, but are not limited to, durations of time of any division of a periodicity of about 2.0 milliseconds or greater, up to any reasonable end time. The time intervals can be, but are not limited to, about 3.0 millisecond, about 5.0 millisecond, about 10 milliseconds, about 25 milliseconds, about 40 milliseconds, about 50 milliseconds, about 60 milliseconds, about 70 milliseconds, about 100 milliseconds, or greater. In other examples, the short time frame can be, but is not limited to, fractions of a second, about a second, between about 1.0 and about 2.0 seconds, or up to about 2.0 seconds, or more.

In some examples, the platform product or cognitive platform can be configured to collect data indicative of a reaction time of a user's response relative to the time of presentation of the tasks. For example, the computing device can be configured to cause the platform product or cognitive platform to provide smaller or larger reaction time window for a user to provide a response to the tasks as a way of adjusting the difficulty level.

In a non-limiting example implementation, the example platform product herein may be formed as, be based on, or be integrated with, an AKILI™ platform product (also referred to herein as an "APP") by Akili Interactive Labs, Inc., Boston, Mass.

As used herein, the term "cData" refers to data collected from measures of an interaction of a user with a computer-implemented device formed as a platform product.

As used herein, the term "nData" refers to data collected from measurements of the one or more physiological components, such as but not limited to EEG/ERP measurement data.

In any example herein, the data (including cData and nData) is collected with user consent.

As used herein, the term "computerized stimuli or interaction" or "CSI" refers to a computerized element that is presented to a user to facilitate the user's interaction with a stimulus or other interaction. As non-limiting examples, the computing device can be configured to present auditory stimulus (presented, e.g., as an auditory computer-implemented time-varying element or an element of a computerized auditory task) or initiate other auditory-based interaction with the user, and/or to present vibrational stimuli (presented, e.g., as a vibrational computer-implemented time-varying element or an element of a computerized vibrational task) or initiate other vibrational-based interaction with the user, and/or to present tactile stimuli (presented, e.g., as a tactile computer-implemented time-varying element or an element of a computerized tactile task) or initiate other tactile-based interaction with the user, and/or to present visual stimuli or initiate other visual-based interaction with the user.

In an example where the computing device is configured to present visual CSI, the CSI can be rendered at at least one user interface to be presented to a user. In some examples, the at least one user interface is configured for measuring responses as the user interacts with CSI computerized element rendered at the at least one user interface. In a non-limiting example, the user interface can be configured such that the CSI computerized element(s) are active, and may require at least one response from a user, such that the user interface is configured to measure data indicative of the type or degree of interaction of the user with the platform product. In another example, the user interface can be configured such that the CSI computerized element(s) are a passive and are presented to the user using the at least one user interface but may not require a response from the user. In this example, the at least one user interface can be configured to exclude the recorded response of an interaction of the user, to apply a weighting factor to the data indicative of the response (e.g., to weight the response to lower or higher values), and/or to measure data indicative of the response of the user with the platform product as a measure of a misdirected response of the user (e.g., to issue a notification or other feedback to the user of the misdirected response).

In an example, the platform product can be configured as a processor-implemented system, method or apparatus that includes a display component, an input device, and at least one processing unit. In an example, the at least one processing unit can be programmed to render at least one user interface, for display at the display component, to present the computerized stimuli or interaction (CSI) or other interactive elements to the user for interaction. In other examples, the at least one processing unit can be programmed to cause an actuating component of the platform product to effect auditory, tactile, or vibrational computerized elements (including CSIs) to effect the stimulus or other interaction with the user. The at least one processing unit can be programmed to cause a component of the program product to receive data indicative of at least one user response based on the user interaction with the CSI or other interactive element (such as but not limited to cData), including responses provided using the input device. In an example where at least one user interface is rendered to present the computerized stimuli or interaction (CSI) or other interactive elements to the user, the at least one processing unit can be programmed to cause user interface to receive the data indicative of at least one user response. The at least one processing unit also can be programmed to: analyze the cData to provide a measure of the individual's cognitive condition, and/or analyze the differences in the individual's performance based on determining the differences between the user's responses (including based on differences in the cData), and/or adjust the difficulty level of the primary task and/or the interference based on the analysis of the cData (including the measures of the individual's performance determined in the analysis), and/or provide an output or other feedback from the platform product that can be indicative of the individual's performance, and/or cognitive assessment, and/or response to cognitive treatment, and/or assessed measures of cognition.

Non-limiting examples of an input device include a touch-screen, or other pressure-sensitive or touch-sensitive surface, a motion sensor, a position sensor, and/or an image capture device (such as but not limited to a camera). The analysis of the individual's performance may include using the computing device to compute percent accuracy, number of hits and/or misses during a session or from a previously completed session. Other indicia that can be used to compute performance measures is the amount time the individual takes to respond after the presentation of a task (e.g., as a targeting stimulus). Other indicia can include, but are not limited to, reaction time, response variance, number of correct hits, omission errors, false alarms, learning rate, spatial deviance, subjective ratings, and/or performance threshold, etc.

In a non-limiting example, the user's performance can be further analyzed to compare the effects of two different types of tasks on the user's performances, where these tasks present different types of interferences (e.g., a distraction or an interruptor). The computing device is configured to present the different types of interference as CSIs or other interactive elements that divert the user's attention from a primary task. For a distraction, the computing device is configured to instruct the individual to provide a primary response to the primary task and not to provide a response (i.e., to ignore the distraction). For an interruptor, the computing device is configured to instruct the individual to provide a response as a secondary task, and the computing device is configured to obtain data indicative of the user's secondary response to the interruptor within a short time frame (including at substantially the same time) as the user's response to the primary task (where the response is collected using at least one input device). The computing device is configured to compute measures of one or more of a user's performance at the primary task without an interference, performance with the interference being a distraction, and performance with the interference being an interruption. The user's performance metrics can be computed based on these measures. For example, the user's performance can be computed as a cost (performance change) for each type of interference (e.g., distraction cost and interruptor/multi-tasking cost). The user's performance level on the tasks can be analyzed and reported as feedback, including either as feedback to the cognitive platform for use to adjust the difficulty level of the tasks, and/or as feedback to the individual concerning the user's status or progression.

In a non-limiting example, the computing device can also be configured to analyze, store, and/or output the reaction time for the user's response and/or any statistical measures for the individual's performance (e.g., percentage of correct or incorrect response in the last number of sessions, over a specified duration of time, or specific for a type of tasks (including non-target and/or target stimuli, a specific type of task, etc.).

In a non-limiting example, the computerized element includes at least one task rendered at a user interface as a visual task or presented as an auditory, tactile, or vibrational task. Each task can be rendered as interactive mechanics that are designed to elicit a response from a user after the user is exposed to stimuli for the purpose of cData and/or nData collection.

In a non-limiting example of a computerized auditory task, the individual may be required to follow a certain computer-rendered path or navigate other environment based on auditory cues emitted to the individual. The processing unit may be configured to cause an auditory component to emit the auditory cues (e.g., sounds or human voices) to provide the individual with performance progress milestones to maintain or modify the path of a computerized avatar in the computer environment, and/or to indicate to the individual their degree of success in performing the physical actions measured by the sensors of the computing device to cause the computerized avatar to maintain the expected course or path.

In a non-limiting example of a computerized vibrational task, the individual may be required to follow a certain computer-rendered path or navigate other environment based on vibrational cues emitted to the individual. The processing unit may be configured to control an actuating component to vibrate (including causing a component of the computing device to vibrate) to provide the individual with the performance progress milestones to maintain or modify the path of a computerized avatar in the computer environment, and/or to indicate to the individual their degree of success in performing the physical actions measured by the sensors of the computing device to cause the computerized avatar to maintain the expected course or path.

In a non-limiting example of a computerized auditory task, the individual may be required to interact with one or more sensations perceived through the sense of touch. In a non-limiting example, a computer-implemented time-varying element may be controlled using a processing unit to actuate an actuating component to present differing types of tactile stimuli (e.g., sensation of touch, textured surfaces, and/or temperatures) for interaction with an individual. For example, an individual with an autism spectrum disorder (ASD) may be sensitive to (including having an aversion to) certain tactile sensory sensations (including being touched as they dress or groom themselves); individuals with Alzheimer's disease and other dementias may benefit through the sense of touch or other tactile sensation. An example tactile task may engage a tactile-sensitive individual in physical actions that causes them to interact with textures and touch sensations.

In a non-limiting example, the computerized element includes at least one platform interaction (gameplay) element of the platform rendered at a user interface, or as auditory, tactile, or vibrational element of a program product. Each platform interaction (gameplay) element of the platform product can include interactive mechanics (including in the form of videogame-like mechanics) or visual (or cosmetic) features that may or may not be targets for cData and/or nData collection.

As used herein, the term "gameplay" encompasses a user interaction (including other user experience) with aspects of the platform product.

In a non-limiting example, the computerized element includes at least one element to indicate positive feedback to a user. Each element can include an auditory signal and/or a visual signal emitted to the user that indicates success at a task or other platform interaction element, i.e., that the user responses at the platform product has exceeded a threshold success measure on a task or platform interaction (gameplay) element.

In a non-limiting example, the computerized element includes at least one element to indicate negative feedback to a user. Each element can include an auditory signal and/or a visual signal emitted to the user that indicates failure at a task or platform interaction (gameplay) element, i.e., that the user responses at the platform product has not met a threshold success measure on a task or platform interaction element.

In a non-limiting example, the computerized element includes at least one element for messaging, i.e., a communication to the user that is different from positive feedback or negative feedback. In a non-limiting example, the computerized element includes at least one element for indicating a reward. A reward computer element can be a computer-generated feature that is delivered to a user to promote user satisfaction with the CSIs and as a result, increase positive user interaction (and hence enjoyment of the user experience).

In a non-limiting example, the cognitive platform can be configured to render multi-task interactive elements. In some examples, the multi-task interactive elements are referred to as multi-task gameplay (MTG). The multi-task interactive elements include interactive mechanics configured to engage the user in multiple temporally-overlapping tasks, i.e., tasks that may require multiple, substantially simultaneous responses from a user.

In any example herein, the multi-tasking tasks can include any combination of two or more tasks. The multi-task interactive elements of an implementation include interactive mechanics configured to engage the individual in multiple temporally-overlapping tasks, i.e., tasks that may require multiple, substantially simultaneous responses from an individual. In non-limiting examples herein, in an individual's performance of at least a portion of a multi-tasking task, the system, method, and apparatus are configured to measure data indicative of the individual's multiple responses in real-time, and also to measure a first response from the individual to a task (as a primary task) substantially simultaneously with measuring a second response from the individual to an interference (as a secondary task).

In an example implementation involving multi-tasking tasks, the computer device is configured (such as using at least one specially-programmed processing unit) to cause the cognitive platform to present to a user two or more different types of tasks, such as but not limited to, target discrimination and/or navigation and/or facial expression recognition or object recognition tasks, during a short time frame (including in real-time and/or substantially simultaneously). The computer device is also configured (such as using at least one specially-programmed processing unit) to collect data indicative of the type of user response received for the multi-tasking tasks, within the short time frame (including in real-time and/or substantially simultaneously). In these examples, the two or more different types of tasks can be presented to the individual within the short time frame (including in real-time and/or substantially simultaneously), and the computing device can be configured to receive data indicative of the user response(s) relative to the two or more different types of tasks within the short time frame (including in real-time and/or substantially simultaneously).

Based on the type of computerized task presented to an individual using the cognitive platform, the types of response(s) expected as a result of the individual interacting with the cognitive platform to perform the task(s), and types of data expected to be received (including being measured) using the cognitive platform, depends on the type of the task(s). For a target discrimination task, the cognitive platform may require a temporally-specific and/or a position-specific response from an individual, including to select between a target and a non-target (e.g., in a GO/NO-GO task) or to select between two differing types of targets, e.g., in a two-alternative forced choice (2AFC) task (including choosing between two differing degrees of a facial expression or other characteristic/feature difference). For a navigation task, the cognitive platform may require a position-specific and/or a motion-specific response from the user. For a facial expression recognition or object recognition task, the cognitive platform may require temporally-specific and/or position-specific responses from the user. In non-limiting examples, the user response to tasks, such as but not limited to targeting and/or navigation and/or facial expression recognition or object recognition task(s), can be recorded using an input device of the cognitive platform. Non-limiting examples of such input devices can include a device for capturing a touch, swipe or other gesture relative to a user interface, an audio capture device (e.g., a microphone input), or an image capture device (such as but not limited to a touch-screen or other pressure-sensitive or touch-sensitive surface, or a camera), including any form of user interface configured for recording a user interaction. In other non-limiting examples, the user response recorded using the cognitive platform for tasks, such as but not limited to targeting and/or navigation and/or facial expression recognition or object recognition task(s), can include user actions that cause changes in a position, orientation, or movement of a computing device including the cognitive platform. Such changes in a position, orientation, or movement of a computing device can be recorded using an input device disposed in or otherwise coupled to the computing device, such as but not limited to a sensor. Non-limiting examples of sensors include a motion sensor, position sensor, and/or an image capture device (such as but not limited to a camera).

In the example herein, "substantially simultaneously" means tasks are rendered, or response measurements are performed, within less than about 5 milliseconds of each other, or within about 10 milliseconds, about 20 milliseconds, about 50 milliseconds, about 75 milliseconds, about 100 milliseconds, or about 150 milliseconds or less, about 200 milliseconds or less, about 250 milliseconds or less, of each other. In any example herein, "substantially simultaneously" is a period of time less than the average human reaction time. In another example, two tasks may be substantially simultaneous if the individual switches between the two tasks within a pre-set amount of time. The set amount of time for switching considered "substantially simultaneously" can be about 1 tenth of a second, 1 second, about 5 seconds, about 10 seconds, about 30 seconds, or greater.

In some examples, the short time frame can be of any time interval at a resolution of up to about 1.0 millisecond or greater. The time intervals can be, but are not limited to, durations of time of any division of a periodicity of about 2.0 milliseconds or greater, up to any reasonable end time. The time intervals can be, but are not limited to, about 3.0 millisecond, about 5.0 millisecond, about 10 milliseconds, about 25 milliseconds, about 40 milliseconds, about 50 milliseconds, about 60 milliseconds, about 70 milliseconds, about 100 milliseconds, or greater. In other examples, the short time frame can be, but is not limited to, fractions of a second, about a second, between about 1.0 and about 2.0 seconds, or up to about 2.0 seconds, or more.

In any example herein, the cognitive platform can be configured to collect data indicative of a reaction time of a user's response relative to the time of presentation of the tasks (including an interference with a task). For example, the computing device can be configured to cause the platform product or cognitive platform to provide smaller or larger reaction time window for a user to provide a response to the tasks as an example way of adjusting the difficulty level.

In a non-limiting example, the cognitive platform can be configured to render single-task interactive elements. In some examples, the single-task interactive elements are referred to as single-task gameplay (STG). The single-task interactive elements include interactive mechanics configured to engage the user in a single task in a given time interval.

According to the principles herein, the term "cognition" refers to the mental action or process of acquiring knowledge and understanding through thought, experience, and the senses. This includes, but is not limited to, psychological concepts/domains such as, executive function, memory, perception, attention, emotion, motor control, and interference processing. An example computer-implemented device according to the principles herein can be configured to collect data indicative of user interaction with a platform product, and to compute metrics that quantify user performance. The quantifiers of user performance can be used to provide measures of cognition (for cognitive assessment) or to provide measures of status or progress of a cognitive treatment.

According to the principles herein, the term "treatment" refers to any manipulation of CSI in a platform product (including in the form of an APP) that results in a measurable improvement of the abilities of a user, such as but not limited to improvements related to cognition, a user's mood, emotional state, and/or level of engagement or attention to the cognitive platform. The degree or level of improvement can be quantified based on user performance measures as describe herein. In an example, the term "treatment" may also refer to a therapy.

According to the principles herein, the term "session" refers to a discrete time period, with a clear start and finish, during which a user interacts with a platform product to receive assessment or treatment from the platform product (including in the form of an APP). In examples herein, a session can refer to at least one trial or can include at least one trial and at least one other type of measurement and/or other user interaction. As a non-limiting example, a session can include at least one trial and one or more of a measurement using a physiological or monitoring component and/or a cognitive testing component. As another non-limiting example, a session can include at least one trial and receipt of data indicative of one or more measures of an individual's condition, including physiological condition and/or cognitive condition.

According to the principles herein, the term "assessment" refers to at least one session of user interaction with CSIs or other feature or element of a platform product. The data collected from one or more assessments performed by a user using a platform product (including in the form of an APP) can be used as to derive measures or other quantifiers of cognition, or other aspects of a user's abilities.

In an example, an assessment can include presenting a task and optionally an interference to an individual, and evaluating the data indicative of the performance of the individual with and/or without the interference. An assessment is different from a training session in that it does not seek to train the individual, but rather to evaluate the performance of the individual. For example, unlike a training session, the difficulty level from trial to trial (or from session to session) in an assessment does not change or adapt to the performance of the individual. The computing system can be configured to maintain the difficulty level in an assessment substantially the same, e.g. at the difficulty level determined by using thresholding (described in greater detail below). In another example, the assessment may be adapted using a psychometric analysis technique, such as but not limited to staircase procedures or maximum likelihood procedures, to adaptively determine the ability of the individual. An assessment may be performed prior to and/or after one or more training sessions (based on adaptively modified tasks and/or interference).

According to the principles herein, the term "cognitive load" refers to the amount of mental resources that a user may need to expend to complete a task. This term also can be used to refer to the challenge or difficulty level of a task or gameplay.

According to the principles herein, the term "emotional load" refers to cognitive load that is specifically associated with processing emotional information or regulating emotions or with affective bias in an individual's preference for a negative emotion, perspective, or outcome as compared to a positive emotion, perspective, or outcome. The emotional load may be modified (i.e., increased or decreased) by using an example apparatus, system or method to configure a computer-implemented time-varying element to indicate to the individual(s) their degree of success in performing a portion of a task and/or an interference (including a task with or without an interference).

According to the principles herein, the term "ego depletion" refers to a state reached by a user after a period of effortful exertion of self-control, characterized by diminished capacity to exert further self-control. The state of ego-depletion may be measured based on data collected for a user's responses to the interactive elements rendered at user interfaces, or as auditory, tactile, or vibrational elements, of a platform product described hereinabove.

According to the principles herein, the term "emotional processing" refers to a component of cognition specific to cognitive and/or neurologic processing of emotion/affect/mood or parasympathetic arousal. The degree of emotional processing may be measured based on data collected for a user's responses to the interactive computer-implemented time-varying elements rendered at user interfaces (including as an auditory, tactile, or vibrational element), of a platform product described hereinabove.

An example system, method, and apparatus according to the principles herein includes a platform product (including using an APP) that uses a cognitive platform configured to render at least one computer-implemented time-varying element, to provide additional control of cognitive load as an overt component for tasks in MTG or STG. In one example, the computer-implemented time-varying element is used in the tasks configured to assess cognition or improve cognition related to emotions, and the data (including cData) collected as a measure of user interaction with the rendered computer-implemented time-varying element in the platform product is used to determine the measures of the assessment of cognition or the improvement to measures of cognition after a treatment configured for interaction using the user interface, or as auditory, tactile, or vibrational elements, of the platform product. The computer-implemented time-varying element can be configured to collect data to measure the impact of emotions on non-emotional cognition, such as by causing the user interface to render spatial tasks for the user to perform, and/or to collect data to measure the impact of non-emotional cognition on emotions, such as by causing the user interface to render features that employ measures of executive function to regulate emotions. In one example implementation, the user interface can be configured to render tasks for identifying the emotion indicated by the CSI (based on measurement data), maintaining that identification in working memory, and comparing it with the measures of emotion indicated by subsequent CSI, while under cognitive load due to MTG.

In an example, the program platform comprises a computing device that is configured to present to a user a cognitive platform based on interference processing. In an example system, method and apparatus that implements interference processing, at least one processing unit is programmed to render at least one first user interface or cause an actuating component to generate an auditory, tactile, or vibrational signal, to present first CSIs as a primary task that requires a first type of response from a user. The example system, method and apparatus is also configured to cause the at least one processing unit to render at least one second user interface or cause the actuating component to generate an auditory, tactile, or vibrational signal, to present second CSIs as a interference with the primary task, requiring a second type of response from the user to the primary task in the presence of the interference. In a non-limiting example, the second type of response can include the first type of response to the primary task and a secondary response to the interference. In another non-limiting example, the second type of response may not include, and be quite different from, the first type of response. The at least one processing unit is also programmed to receive data indicative of the first type of response and the second type of response based on the user interaction with the platform product (such as but not limited to cData), such as but not limited to by rendering the at least one user interface to receive the data. The platform product also can be configured to receive nData indicative of the measurements made using the one or more physiological components before, during, and/or after the user interacts with the cognitive platform. The at least one processing unit also can be programmed to: analyze the cData and/or nData to provide a measure of the individual's physiological condition and/or cognitive condition, and/or analyze the differences in the individual's performance based on determining the differences between the measures of the user's first type and second type of responses (including based on differences in the cData) and differences in the associated nData. The at least one processing unit also can be programmed to: adjust the difficulty level of the primary task and/or the interference based on the analysis of the cData and/or nData (including the measures of the individual's performance and/or physiological condition determined in the analysis), and/or provide an output or other feedback from the platform product that can be indicative of the individual's performance, and/or cognitive assessment, and/or response to cognitive treatment, and/or assessed measures of cognition.

In an example, the feedback from the differences in the individual's performance based on determining the differences between the measures of the user's first type and second type of responses and the nData can be used as an input in the cognitive platform that indicates real-time performance of the individual during one or more session(s). The data of the feedback can be used to as an input to a computation component of the computing device to determine a degree of adjustment that the cognitive platform makes to a difficulty level of the primary task and/or the interference that the user interacts within the same ongoing session and/or within a subsequently-performed session.

As a non-limiting example, the cognitive platform based on interference processing can be based on the Project: EVO™ platform by Akili Interactive Labs, Inc., Boston, Mass.

In an example system, method and apparatus according to the principles herein that is based on interference processing, the user interface is configured such that, as a component of the interference processing, one of the discriminating features of the targeting task that the user responds to is a feature in the platform that displays an emotion, a shape, a color, and/or a position that serves as an interference element in interference processing.

In another example system, method and apparatus according to the principles herein that is based on interference processing, a platform product may include a working-memory task such as cognitive tasks that employs computer-implemented time-varying element, where the affective content is either a basis for matching or a distractive element as part of the user interaction, within a MTG or a STG.

An example system, method, and apparatus according to the principles herein includes a platform product (including using an APP) that uses a cognitive platform configured to render at least one integrating computer-implemented time-varying element in a MTG or a STG, where the user interface is configured to not explicitly call attention to the computer-implemented time-varying element. The user interface of the platform product may be configured to render computer-implemented time-varying element for the purpose of assessing or adjusting emotional biases in attention, interpretation, or memory, and to collected data indicative of the user interaction with the platform product.

An example system, method, and apparatus according to the principles herein includes a platform product (including using an APP) that uses a cognitive platform configured to render at least one computer-implemented time-varying element that reinforces positive or negative feedback provided within the one or more tasks.

An example system, method, and apparatus according to the principles herein includes a platform product (including using an APP) that uses a cognitive platform configured to render at least one computer-implemented time-varying element that introduces fixed or adjustable levels of cognitive or emotional load to the user interaction (including to gameplay). This could be used for the purposes of modulating the difficulty of a MTG or a STG. This includes using computer-implemented time-varying element(s) that conflicts with the positive feedback or negative feedback provided within the one or more tasks, or using computer-implemented time-varying element(s) to induce ego depletion to impact the user's cognitive control capabilities.

An example system, method, and apparatus according to the principles herein includes a platform product (including using an APP) that uses a cognitive platform configured to render and integrate at least one simultaneous conflicting computer-implemented time-varying element(s) into different tasks during a MTG. This could be used for the purpose of assessing or improving measures of cognition related to the user interaction with the platform product indicating the user's handling of conflicting emotional information.

An example system, method, and apparatus according to the principles herein includes a platform product (including using an APP) that is configured to set baseline CSI levels/attributes in APP session(s) based on measures of physiological measures (such as but not limited to EEG measurements and ERP events detection) including measurement nData indicative of cognition and/or neuropsychological disorders, to increase accuracy of assessment and efficiency of treatment. The CSIs may be used to calibrate physiological measurements (including EEG measurements and ERP events detection) to individual user dynamics of nData.

An example system, method, and apparatus according to the principles herein includes a platform product (including using an APP) that is configured to collect and analyze cData and/or nData, and adjust the cognitive platform to cause subtle manipulation of CSIs, such that the physiological measurements (including EEG measurements and ERP events detection) indicate a change that normalizes the physiological measurements to those reflecting an attentive state of cognition of the user.

An example system, method, and apparatus according to the principles herein includes a platform product (including using an APP) that is configured to collect and analyze cData and/or nData, and adjust the cognitive platform to cause overt manipulation of CSIs when the physiological measurements (including EEG measurements and ERP events detection) are indicative of an inattentive state of the user.

An example system, method, and apparatus according to the principles herein includes a platform product (including using an APP) that is configured to use physiological measurements (including EEG measurements and ERP events detection) to detect attentive states to optimize delivery of CSIs related to treatment or assessment.

An example system, method, and apparatus according to the principles herein includes a platform product (including using an APP) that is configured to use analysis of nData from physiological measurements (including EEG measurements and ERP events detection) with CSI cData to detect and direct attention to specific CSIs related to treatment or assessment through subtle or overt manipulation of CSIs.

An example system, method, and apparatus according to the principles herein includes a platform product (including using an APP) that is configured to use analysis of CSIs patterns of cData with nData from physiological measurements (including EEG measurements and ERP events detection) within or across assessment or treatment sessions to generate user physiological profiles (including profiles of ideal, optimal, or desired user responses) of cData and nData and manipulate CSIs across or within sessions to guide users to replicate these user physiological profiles. For example, based on analysis of the cData and nData measured and collected, and the performance metrics derived from such data, in the changes in values of the cData and nData can be correlated to the changes made to the CSIs executed at the user interfaces, and the patterns in the correlation can be identified and used to construct the user physiological profile. The ideal, optimal, and/or desired user responses can be determined as those collected from individuals known to exhibit full dedicated attention and/or effort to performing the tasks and/or interference. The cData and nData measured and collected, and the performance metrics computed for a set of individuals known as having exhibited the ideal, optimal, and/or desired user responses, can be used to generate the user physiological profile(s). In an example, the computing system can be configured to compare the cData and/or nData measured and collected from a test individual that is to be assessed and/or trained to the user physiological profile(s), to classify the responses of the test individual, e.g., as to level of user engagement, degree of user focus, rate of improvement of user performance, and the like. In an example, the computing system can be configured to compare the cData and/or nData measured and collected from a test individual that is to be assessed and/or trained to the user physiological profile(s), to compute a weighting factor to be applied to a computed performance metric for the test individual to determine a weighted performance metric. The weighted performance metric can be used in pace of the actual performance metric to determine the adjustment (adapting) of the difficulty levels from one trial to another and/or from one session to another. The CSIs can be modified such that cData and/or nData measured and collected from a test individual's performance of the tasks and/or interference correlates highly with (including substantially matching with) the user physiological profile(s), thereby replicating the user physiological profile(s). That is, the difficulty level of the tasks and/or interference can be adjusted such that the cData and/or nData indicative of the response from the test individual more closely correlates with a predetermined user physiological profile.

An example system, method, and apparatus according to the principles herein includes a platform product (including using an APP) that is configured to compute the physiological profile based on measurements using two or more differing types of physiological components and/or two or more different physiological measurements over time.

An example system, method, and apparatus according to the principles herein includes a platform product (including using an APP) that is configured to monitor physiological measurements (including EEG measurements and ERP events detection) for indicators of parameters related to user engagement and to optimize the cognitive load generated by the CSIs to align the individual's performance level, as a function of time, to an optimal engaged state (such as but not limited to through comparison to the user physiological profile(s)), to maximize neural plasticity and transfer of benefit resulting from treatment.

As used herein, the term "neural plasticity" refers to targeted re-organization of the central nervous system.

An example system, method, and apparatus according to the principles herein includes a platform product (including using an APP) that is configured to monitor physiological measurements (including EEG measurements and ERP events detection) indicative of anger and/or frustration to promote continued user interaction (also referred to as "play") with the cognitive platform by offering alternative CSIs or disengagement from CSIs.

An example system, method, and apparatus according to the principles herein includes a platform product (including using an APP) that is configured to monitor physiological measurements (including EEG measurements and ERP events detection) indicative of happiness and/or satisfaction (e.g., based on a meditative state and/or state of focused attention) to promote continued user interaction (also referred to as "play") with the cognitive platform by offering alternative CSIs or disengagement from CSIs.

An example system, method, and apparatus according to the principles herein includes a platform product (including using an APP) that is configured to monitor physiological measurements (including EEG measurements and ERP events detection) indicative of anger and/or frustration to promote continued user interaction (also referred to as "play") with the cognitive platform by modulating CSI cognitive load to normalize EEG signals in nData to reflect an emotionally regulated state.

An example system, method, and apparatus according to the principles herein includes a platform product (including using an APP) that is configured to change CSI dynamics within or across assessment or treatment sessions to optimize physiological measurements (including EEG measurements and ERP events detection) related to cognition or other physiological or cognitive aspects of the user.

An example system, method, and apparatus according to the principles herein includes a platform product (including using an APP) that is configured to adjust the CSIs or CSI cognitive load if physiological measurement signals (including EEG/ERP measurement signals) of task automation (e.g., the user is exhibiting little engagement or is providing responses indicating lack of interest in providing the responses) are detected, or the physiological measurements that relate to task learning show signs of attenuation.

An example system, method, and apparatus according to the principles herein includes a platform product (including using an APP) that is configured to monitor physiological measurement signals (including EEG/ERP measurement signals) of positive and negative feedback and adjust feedback levels from the cognitive platform and CSIs (including by adjusting the level of difficulty of tasks and/or interference presented from one trial or session to another, and/or adjusting the type of performance metrics or progress indicators output to the individual), to normalize and/or optimize the performance metrics computed based on the measured and collected response data from the individual (including cData and/or nData). The normalized and/or optimized performance metrics can be output or otherwise displayed to the individual to promote user attention to, and user engagement with, the CSIs used to present the tasks and/or interference.

An example system, method, and apparatus according to the principles herein includes a platform product (including using an APP) that is configured to monitor physiological measurement indicating signals of user engagement and to continuously adjust auditory characteristics, such as but not limited to volume, pitch, or rhythm, and/or visual characteristics, such as but not limited to color or brightness, in a feedback loop. The example feedback loop can be implemented using one or more controllers, such as but not limited to a proportional controller, a proportional/integral controller, a proportional/differential controller, or a proportional/integral/differential (PID) controller. Based on the analysis of the data indicative of the physiological measurement, the one or more controllers can be applied to issue control signals effect the feedback loop, i.e., to continuously adjust the auditory characteristics and/or visual characteristics of the tasks and/or interference presented to the user, until the physiological measurements of the individual indicate signals of a sufficient level of user engagement. In any example herein, the engagement level can be pre-specified or determined based on a compilation (e.g., average) of previous measurements from an individual.

An example system, method, and apparatus according to the principles herein includes a platform product (including using an APP) that is configured to monitor physiological measurement indicating signals of user engagement and to cause the processing unit to introduce visual or auditory messages with the tasks and/or interference until strength of the physiological measurement move to levels indicative of sufficient user engagement.

An example system, method, and apparatus according to the principles herein includes a platform product (including using an APP) that is configured to monitor physiological measurement indicating signals of user engagement and to analyze data indicative of a score of an individual in interacting with the tasks and/or interference to determine the effects of the adjustment of the visual or auditory messages and/or the adjustments to visual or auditory characteristics used with the tasks and/or interference on the user's physiological measurements, to determine the type messages and/or adjustments are more likely to have a desired effect on the individual (such as increased user engagement). The results of the analysis can be used to control the processing unit to adjust the visual or auditory messages and/or to adjust the visual or auditory characteristics used with the tasks and/or interference, until the physiological measurement of the individual change to levels indicative of sufficient user engagement.

In any example herein, the physiological measurement indicating signals of user engagement can be, but are not limited to alpha and/or theta wave EEG signals, and/or heart-rate as indicators, and/or measurements from other types of physiological components as described herein.

An example system, method, and apparatus according to the principles herein includes a platform product (including using an APP) that is configured to detect sub-optimal perceptual detection and/or discrimination of CSI stimuli and adjust stimuli across or within treatment or assessment sessions as informed by physiological measurements (including EEG measurements and ERP events detection).

An example system, method, and apparatus according to the principles herein includes a platform product (including using an APP) that is configured to detect physiological measurements (including ERP measurements) related to errors in an inattentive user state versus non-engaged user state and adjust patterns and dynamics of CSIs to encourage engagement of a user to result in physiological measurement data indicative of an optimal physiological response profile of nData.

An example system, method, and apparatus according to the principles herein includes a platform product (including using an APP) that is configured to combine signals from CSI cData with physiological measurements (including EEG measurements and ERP events detection) of user task engagement to optimize individualized treatment promoting improvement of indicators of cognitive abilities, and thereby, cognition.

An example system, method, and apparatus according to the principles herein includes a platform product (including using an APP) that is configured to use physiological measurements (including EEG measurements and ERP events detection) to indicate cases of a user providing deliberately deviant responses to CSIs, as an indicator of an individual that is "faking bad", e.g., deviant responses indicating that the individual is deliberately providing poor or false performance in response to the tasks and/or interference, in their interaction(s) with the platform.

An example system, method, and apparatus according to the principles herein includes a platform product (including using an APP) that is configured to use a physiological profile of nData from physiological measurements (including EEG measurements and ERP events detection) to confirm/verify/authenticate a user's identity.

An example system, method, and apparatus according to the principles herein includes a platform product (including using an APP) that is configured to use physiological measurements (including EEG measurements and ERP events detection) to detect positive emotional response to CSIs in order to catalog individual user preferences to customize CSIs to optimize enjoyment and promote continued engagement with assessment or treatment sessions.

An example system, method, and apparatus according to the principles herein includes a platform product (including using an APP) that is configured to generate user physiological profiles of cognitive improvement (such as but not limited to, user physiological profiles associated with users classified or known to exhibit improved working memory, attention, processing speed, and/or perceptual detection/discrimination), and deliver a treatment that adapts CSIs to optimize the profile of a new user as confirmed by profiles from nData from physiological measurements (including EEG measurements and ERP events detection). In an example, the profile of the new user can be optimized by adjusting the difficulty level of the tasks and/or interference to such that the cData and/or nData indicative of the response from the individual more closely correlates with a predetermined reference user physiological profile.

An example system, method, and apparatus according to the principles herein includes a platform product (including using an APP) that is configured to adjust the difficulty level by adjusting one or more of a sound, music, message of encouragement, and/or imposing a delay in rendering of the primary task and/or the interference (e.g., to allow the individual additional time to enter an attentive or meditative state).

An example system, method, and apparatus according to the principles herein includes a platform product (including using an APP) that is configured to provide to a user a selection of one or more profiles configured for cognitive improvement.

An example system, method, and apparatus according to the principles herein includes a platform product (including using an APP) that is configured to monitor auditory and visual physiological measurements (including EEG measurements and ERP events detection) to detect interference from external environmental sources that may interfere with the assessment or treatment being performed by a user using an APP.

An example system, method, and apparatus according to the principles herein includes a platform product (including using an APP) that is configured to use localized signals from physiological measurements (including EEG measurements and ERP events detection) to detect concurrent user engagement with and attention to CSIs, to ensure that a user is being attentive to and interacting with the CSI, and the user is engaged with the CSIs to an optimal degree as required for assessment or treatment.

An example system, method, and apparatus according to the principles herein includes a platform product (including using an APP) that is configured to use localized signals from physiological measurements (including EEG measurements and ERP events detection) to use specific physiological profiles of nData from physiological measurements (including EEG measurements and ERP events detection) as a determinant or decision of whether a user (including a patient using a medical device) is likely to respond or not to respond to treatment. For example, the example system, method, and apparatus can be configured to select whether a user (including a patient using a medical device) should receive treatment based on specific physiological measurements (including EEG measurements and ERP events detection) that can be used as signatures that have been validated to predict efficacy in certain user populations (including patient populations).

An example system, method, and apparatus according to the principles herein includes a platform product (including using an APP) that is configured to use physiological measurements (including EEG measurements and ERP events detection) to monitor a user's ability to anticipate CSI(s) and manipulate CSIs patterns and/or rules. For example, the measured nData can be analyzed to determine physiological signals indicating that a user no longer exerts a threshold level of attention or engagement in the tasks and/or interference, even though the individual is still performing the physical actions to provide the responses. The computing system can be configured to identify the pattern of anticipation, and modify the difficulty level of the tasks and/or interference to disrupt user anticipation of response to CSIs, and as a result, optimize the treatment and/or assessment of the individual in the APP.

An example system, method, and apparatus according to the principles herein includes a platform product (including using an APP) that uses video or audio sensors to detect the performance of physical or vocal actions by the user, as a means of response to CSI within a task. These actions may be representations of emotions, such as facial or vocal expressions, or words.

An example system, method, and apparatus according to the principles herein includes a platform product (including using an APP) that uses a cognitive platform configured to render at least one computer-implemented time-varying element as part of an emotional regulation strategy to enable better user engagement with the platform product when the analysis of the collected date indicates that the user is in a non-optimal emotional state. For example, if the data analysis of the performance measures of the platform product determines that the user is frustrated and unable to properly engage in treatment or assessment, the platform product could be configured to introduce some sort of break in the normal interaction sequence that employs computer-implemented time-varying elements until after a time interval that the user is deemed ready to engage sufficiently again. This can be a fixed interval of time or an interval of time computed based on the user's previous performance data.

An example system, method, and apparatus according to the principles herein includes a platform product (including using an APP) that uses a cognitive platform configured to render at least one computer-implemented time-varying element in the interaction sequence, measure user responses, and adjust the CSI accordingly. These measurements may be compared with the user responses to interaction sequences in the platform that do not present computer-implemented time-varying elements, in order to determine measures of the user's emotional reactivity. This measurement, with or without comparison to measurements made during interaction sequences that do not present computer-implemented time-varying elements, may be for the purpose of assessing the user's emotional state. The CSI adjustments might be initiating an emotional regulation strategy to enable better engagement with the platform product or initiating certain interactive elements, such as but not limited to tasks or rewards, only under certain emotional conditions. The user response measurement may employ use of inputs such as touchscreens, keyboards, or accelerometers, or passive external sensors such as video cameras, microphones, eye-tracking software/devices, bio-sensors, and/or neural recording (e.g., electroencephalogram), and may include responses that are not directly related to interactions with the platform product, as well as responses based on user interactions with the platform product. The platform product can present measures of a user's emotional state that include a measure of specific moods and/or a measure of general state of ego depletion that impacts emotional reactivity.

An example system, method, and apparatus according to the principles herein includes a platform product (including using an APP) that uses a cognitive platform configured to render at least one computer-implemented time-varying element to suggest possible appropriate task responses. This may be used to evaluate the user's ability to discern emotional cues, or to choose appropriate emotional responses.

An example system, method, and apparatus according to the principles herein includes a platform product (including using an APP) that uses a cognitive platform configured to render at least one computer-implemented time-varying element in time-limited tasks, where the time limits may be modulated. This may be for the purposes of measuring user responses via different cognitive processes, such as top-down conscious control vs. bottom-up reflexive response.

An example system, method, and apparatus according to the principles herein includes a platform product (including using an APP) that uses a cognitive platform configured to render at least one computer-implemented time-varying element with levels of valence determined based on previous user responses to computer-implemented time-varying element at one or more level of valence. This may apply an adaptive algorithm to progressively adjust the level of valence to achieve specific goals, such as creating a psychometric curve of expected user performance on a task across stimulus or difficulty levels, or determining the specific level at which a user's task performance would meet a specific criterion like 50% accuracy in a Go/No-Go task.

As described hereinabove, the example systems, methods, and apparatus according to the principles herein can be implemented, using at least one processing unit of a programmed computing device, to provide the cognitive platform of a platform product. FIG. 1 shows an example apparatus 100 according to the principles herein that can be used to implement the cognitive platform described hereinabove herein. The example apparatus 100 includes at least one memory 102 and at least one processing unit 104.

The at least one processing unit 104 is communicatively coupled to the at least one memory 102.

Example memory 102 can include, but is not limited to, hardware memory, non-transitory tangible media, magnetic storage disks, optical disks, flash drives, computational device memory, random access memory, such as but not limited to DRAM, SRAM, EDO RAM, any other type of memory, or combinations thereof. Example processing unit 104 can include, but is not limited to, a microchip, a processor, a microprocessor, a special purpose processor, an application specific integrated circuit, a microcontroller, a field programmable gate array, any other suitable processor, or combinations thereof.

The at least one memory 102 is configured to store processor-executable instructions 106 and a computing component 108. In a non-limiting example, the computing component 108 can be used to receive (including to measure) substantially simultaneously two or more of: (i) the response from the individual to a task (providing at least a portion of cData), (ii) a secondary response of the individual to an interference (providing at least a portion of cData), and (iii) at least one physiological measure using of the individual (using a measurement of at least one physiological component to provide at least a portion of nData). In a non-limiting example, the computing component 108 can be used to analyze the cData and/or nData received from the cognitive platform coupled with the one or more physiological components as described herein to compute at least one performance metric comprising at least one quantified indicator of cognitive abilities. In another non-limiting example, the computing component 108 can be used to compute signal detection metrics in computer-implemented adaptive response-deadline procedures. As shown in FIG. 1, the memory 102 also can be used to store data 110, such as but not limited to the physiological measurement data 112 received from a physiological component coupled to or integral with the apparatus 100 and/or data indicative of the response of an individual to the one or more tasks, including responses to tasks rendered at a user interface of the apparatus 100 and/or tasks generated using an auditory, tactile, and/or vibrational signal from an actuating component coupled to or integral with the apparatus 100, and/or data indicative of one or more of an amount, concentration, or dose titration, or other treatment regimen of a drug, pharmaceutical agent, biologic, or other medication being or to be administered to an individual.

In a non-limiting example, the at least one processing unit 104 executes the processor-executable instructions 106 stored in the memory 102 at least to measure substantially simultaneously two or more of: (i) the response from the individual to a task (providing at least a portion of cData), (ii) a secondary response of the individual to an interference (providing at least a portion of cData), and (iii) at least one physiological measure using of the individual (using a measurement of at least one physiological component to provide at least a portion of nData). The at least one processing unit 104 also executes the processor-executable instructions 106 stored in the memory 102 at least to analyze the cData and/or nData received from the cognitive platform coupled with the one or more physiological components as described herein to compute at least one performance metric comprising at least one quantified indicator of cognitive abilities, using the computing component 108. The at least one processing unit 104 also executes processor-executable instructions 106 to control a transmission unit to transmit values indicative of the analysis of the cData and/or nData received from the cognitive platform coupled with the one or more physiological components as described herein, and/or controls the memory 102 to store values indicative of the analysis of the cData and/or nData (including the at least one performance metric). The at least one processing unit 104 also may be programmed to execute processor-executable instructions 106 to control a transmission unit to transmit values indicative of the computed signal detection metrics and/or controls the memory 102 to store values indicative of the signal detection metrics In another non-limiting example, the at least one processing unit 104 executes the processor-executable instructions 106 stored in the memory 102 at least to apply signal detection metrics in computer-implemented adaptive response-deadline procedures.

In any example herein, the user interface may be a graphical user interface.

In another non-limiting example, the measurement data 112 can be collected from measurements using one or more physiological or monitoring components and/or cognitive testing components. In any example herein, the one or more physiological components are configured for performing physiological measurements. The physiological measurements provide quantitative measurement data of physiological parameters and/or data that can be used for visualization of physiological structure and/or functions.

In any example herein, the measurement data 112 can include reaction time, response variance, correct hits, omission errors, number of false alarms (such as but not limited to a response to a non-target), learning rate, spatial deviance, subjective ratings, and/or performance threshold, or data from an analysis, including percent accuracy, hits, and/or misses in the latest completed trial or session. Other non-limiting examples of measurement data 112 include response time, task completion time, number of tasks completed in a set amount of time, preparation time for task, accuracy of responses, accuracy of responses under set conditions (e.g., stimulus difficulty or magnitude level and association of multiple stimuli), number of responses a participant can register in a set time limit number of responses a participant can make with no time limit, number of attempts at a task needed to complete a task, movement stability, accelerometer and gyroscope data, and/or self-rating.

In any example herein, the one or more physiological components can include any means of measuring physical characteristics of the body and nervous system, including electrical activity, heart rate, blood flow, and oxygenation levels, to provide the measurement data 112. This can include camera-based heart rate detection, measurement of galvanic skin response, blood pressure measurement, electroencephalogram, electrocardiogram, magnetic resonance imaging, near-infrared spectroscopy, and/or pupil dilation measures, to provide the measurement data 112. The one or more physiological components can include one or more sensors for measuring parameter values of the physical characteristics of the body and nervous system, and one or more signal processors for processing signals detected by the one or more sensors.

Other examples of physiological measurements to provide measurement data 112 include, but are not limited to, the measurement of body temperature, heart or other cardiac-related functioning using an electrocardiograph (ECG), electrical activity using an electroencephalogram (EEG), event-related potentials (ERPs), functional magnetic resonance imaging (fMRI), blood pressure, electrical potential at a portion of the skin, galvanic skin response (GSR), magneto-encephalogram (MEG), eye-tracking device or other optical detection device including processing units programmed to determine degree of pupillary dilation, functional near-infrared spectroscopy (fNIRS), and/or a positron emission tomography (PET) scanner. An EEG-fMRI or MEG-fMRI measurement allows for simultaneous acquisition of electrophysiology (EEG/MEG) data and hemodynamic (fMRI) data.

The example apparatus 100 of FIG. 1 can be configured as a computing device for performing any of the example methods described herein. The computing device can include an App program for performing some of the functionality of the example methods described herein.

In any example herein, the example apparatus 100 can be configured to communicate with one or more of a cognitive monitoring component, a disease monitoring component, and a physiological measurement component, to provide for biofeedback and/or neurofeedback of data to the computing device, for adjusting a type or a difficulty level of one or more of the task, the interference, and the computer-implemented time-varying element, to achieve the desired performance level of the individual. As a non-limiting example, the biofeedback can be based on physiological measurements of the individual as they interact with the apparatus 100, to modify the type or a difficulty level of one or more of the task, the interference, and the computer-implemented time-varying element based on the measurement data indicating, e.g., the individual's attention, mood, or emotional state. As a non-limiting example, the neurofeedback can be based on measurement and monitoring of the individual using a cognitive and/or a disease monitoring component as the individual interacts with the apparatus 100, to modify the type or a difficulty level of one or more of the task, the interference, and the computer-implemented time-varying element based on the measurement data indicating, e.g., the individual's cognitive state, disease state (including based on data from monitoring systems or behaviors related to the disease state).

Figure 2:
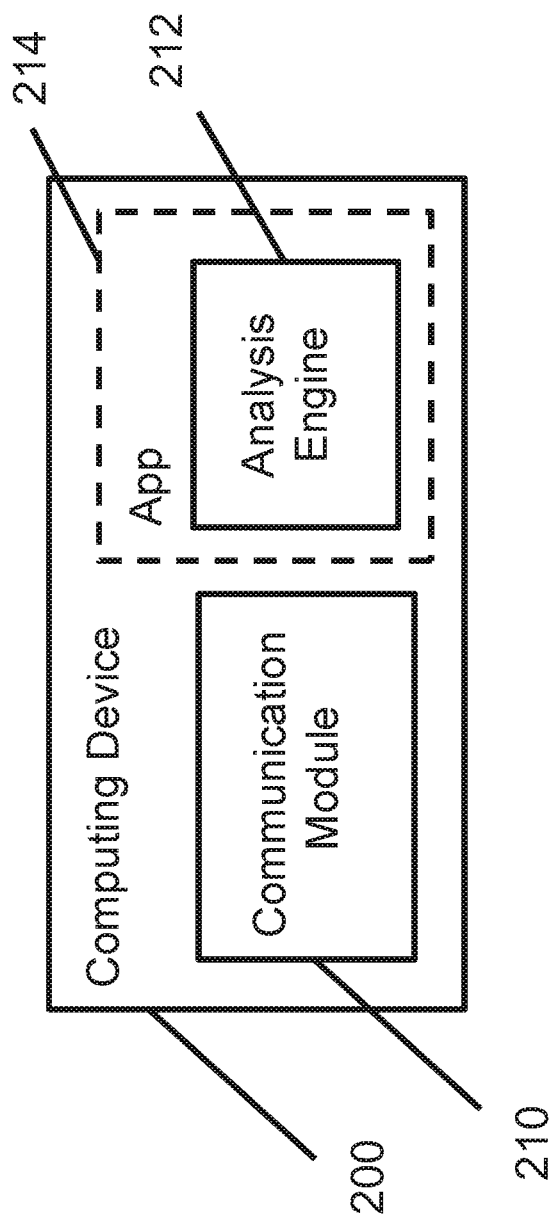
FIG. 2 shows a block diagram of an example computing device, according to the principles herein.

FIG. 2 shows another example apparatus according to the principles herein, configured as a computing device 200 that can be used to implement the cognitive platform according to the principles herein. The example computing device 200 can include a communication module 210 and an analysis engine 212. The communication module 210 can be implemented to receive data indicative of at least one response of an individual to the task in the absence of an interference, and/or at least one response of an individual to the task that is being rendered in the presence of the interference. In an example, the communication module 210 can be implemented to receive substantially simultaneously two or more of: (i) the response from the individual to a task, (ii) a secondary response of the individual to an interference, and (iii) a response of the individual to at least one computer-implemented time-varying element. The analysis engine 212 can be implemented to analyze the data from the at least one sensor component as described herein and/or to analyze the data indicative of the first response and the response of the individual to the at least one computer-implemented time-varying element to compute at least one performance metric comprising at least one quantified indicator of cognitive abilities. In another example, the analysis engine 212 can be implemented to analyze data to generate a response profile, decision boundary metric (such as but not limited to response criteria), a predictive model, and/or other metrics and analyses described herein. As shown in the example of FIG. 2, the computing device 200 can include processor-executable instructions such that a processor unit can execute an application program (App 214) that a user can implement to initiate the analysis engine 212. In an example, the processor-executable instructions can include software, firmware, or other instructions.

The example communication module 210 can be configured to implement any wired and/or wireless communication interface by which information may be exchanged between the computing device 200 and another computing device or computing system. Non-limiting examples of wired communication interfaces include, but are not limited to, USB ports, RS232 connectors, RJ45 connectors, and Ethernet connectors, and any appropriate circuitry associated therewith. Non-limiting examples of wireless communication interfaces may include, but are not limited to, interfaces implementing Bluetooth® technology, Wi-Fi, Wi-Max, IEEE 802.11 technology, radio frequency (RF) communications, Infrared Data Association (IrDA) compatible protocols, Local Area Networks (LAN), Wide Area Networks (WAN), and Shared Wireless Access Protocol (SWAP).

In an example implementation, the example computing device 200 includes at least one other component that is configured to transmit a signal from the apparatus to a second computing device. For example, the at least one component can include a transmitter or a transceiver configured to transmit a signal including data indicative of a measurement by at least one sensor component to the second computing device.

In any example herein, the App 214 on the computing device 200 can include processor-executable instructions such that a processor unit of the computing device implements an analysis engine to analyze data indicative of the individual's response to the rendered tasks and/or interference (either or both with computer-implemented time-varying element) and the response of the individual to the at least one computer-implemented time-varying element to compute at least one performance metric comprising at least one quantified indicator of cognitive abilities. In another example, the App 214 on the computing device 200 can include processor-executable instructions such that a processor unit of the computing device implements an analysis engine to analyze the data indicative of the individual's response to the rendered tasks and/or interference (either or both with computer-implemented time-varying element) and the response of the individual to the at least one computer-implemented time-varying element to provide a predictive model based on the computed values of the performance metric, to generate a predictive model output indicative of a measure of cognition, a mood, a level of cognitive bias, or an affective bias of the individual. In some examples, the App 214 can include processor-executable instructions such that the processing unit of the computing device implements the analysis engine to provide a predictive model as to response profile, decision boundary metric (such as but not limited to response criteria), a predictive model, and other metrics and analyses described herein. In some example, the App 214 can include processor-executable instructions to provide one or more of: (i) a predictive model output indicative of the cognitive capabilities of the individual, (ii) a likelihood of the individual experiencing an adverse event in response to administration of the pharmaceutical agent, drug, or biologic, (iii) a change in one or more of the amount, concentration, or dose titration of the pharmaceutical agent, drug, or biologic, and (iv) a change in the individual's cognitive capabilities, a recommended treatment regimen, or recommending or determining a degree of effectiveness of at least one of a behavioral therapy, counseling, or physical exercise.

In any example herein, the App 214 can be configured to receive measurement data including physiological measurement data of an individual received from a physiological component, and/or data indicative of the response of an individual to a task and/or an interference rendered at a user interface of the apparatus 100 (as described in greater detail below), and/or data indicative of one or more of an amount, concentration, or dose titration, or other treatment regimen of a drug, pharmaceutical agent, biologic, or other medication being or to be administered to an individual.

FIG. 3A shows a non-limiting example system, method, and apparatus according to the principles herein, where the platform product (including using an APP) is configured as a cognitive platform 302 that is separate from, but configured for coupling with, one or more of the physiological components 304.

FIG. 3B shows another non-limiting example system, method, and apparatus according to the principles herein, where the platform product (including using an APP) is configured as an integrated device 310, where the cognitive platform 312 that is integrated with one or more of the physiological components 314.

Figure 4:
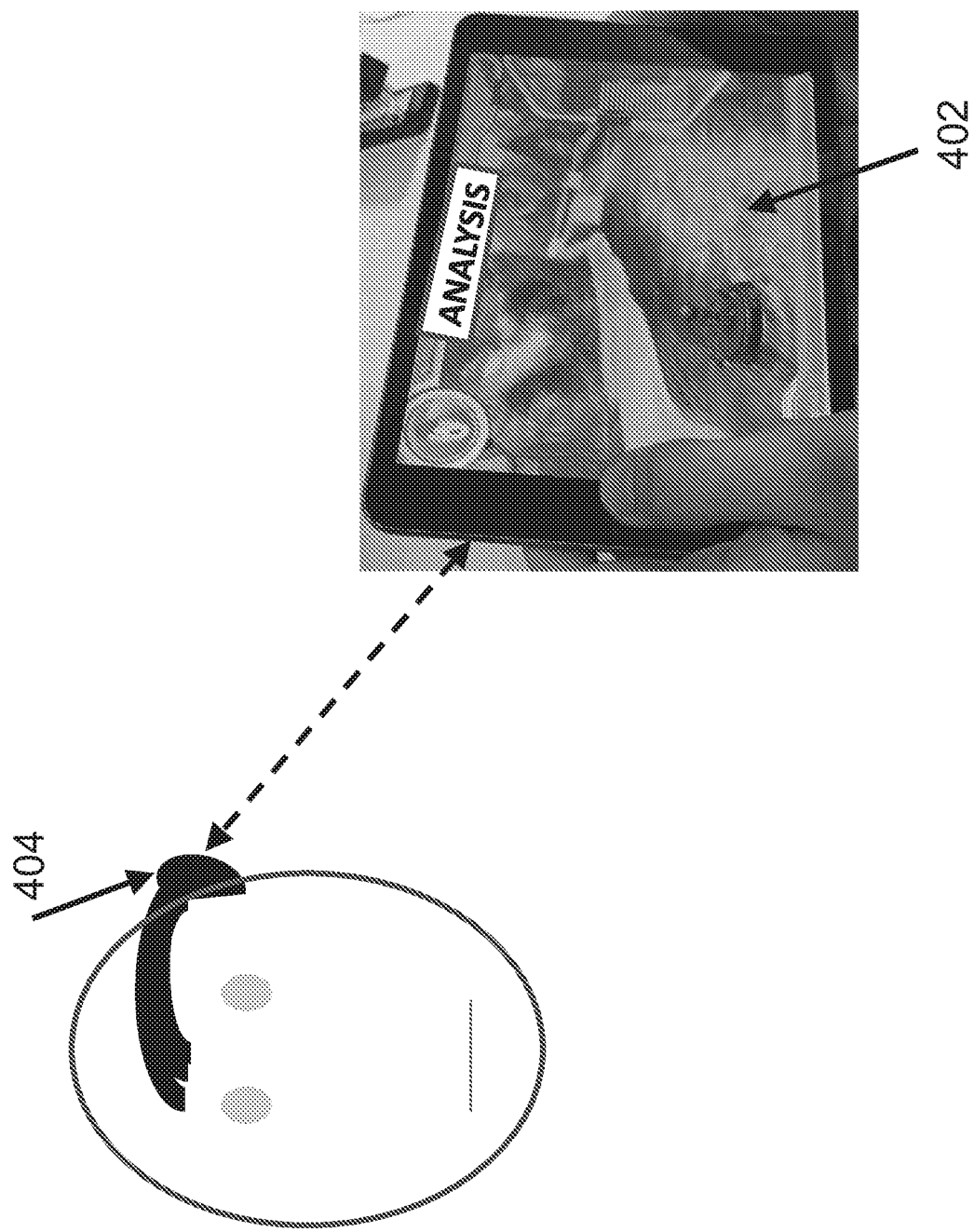
FIG. 4 shows another example system, according to the principles herein.

FIG. 4 shows a non-limiting example implementation of a system, where the platform product (including using an APP) is configured as a cognitive platform 402 that is configured for coupling with a physiological component 404. In this example, the cognitive platform 402 is configured as a tablet including at least one processor programmed to implement the processor-executable instructions associated with the tasks and CSIs described hereinabove, to receive cData associated with user responses from the user interaction with the cognitive platform 402, to receive the nData from the physiological component 404, to analyze the cData and/or nData as described hereinabove, and to analyze the cData and/or nData to provide a measure of the individual's physiological condition and/or cognitive condition, and/or analyze the differences in the individual's performance based on determining the differences between the user's responses and the nData, and/or adjust the difficulty level of the computerized stimuli or interaction (CSI) or other interactive elements based on the individual's performance determined in the analysis and based on the analysis of the cData and/or nData, and/or provide an output or other feedback from the platform product indicative of the individual's performance, and/or cognitive assessment, and/or response to cognitive treatment, and/or assessed measures of cognition. In this example, the physiological component 404 is configured as an EEG mounted to a user's head, to perform the measurements before, during and/or after user interaction with the cognitive platform 402, to provide the nData.

In a non-limiting example implementation, the EEG can be a low-cost EEG for medical treatment validation and personalized medicine. The low-cost EEG device can be easier to use and has the potential to vastly improve the accuracy and the validity of medical applications. In this example, the platform product may be configured as an integrated device including the EEG component coupled with the cognitive platform, or as a cognitive platform that is separate from, but configured for coupling with the EEG component.

In a non-limiting example use for treatment validation, the user interacts with a cognitive platform, and the EEG is used to perform physiological measurements of the user. Any change in EEG measurements data (such as brainwaves) are monitored based on the actions of the user in interacting with the cognitive platform. The nData from the measurements using the EEG (such as brainwaves) can be collected and analyzed to detect changes in the EEG measurements. This analysis can be used to determine the types of response from the user, such as whether the user is performing according to an optimal or desired physiological profile.

In a non-limiting example use for personalized medicine, the nData from the EEG measurements be used to identify changes in user performance/condition that indicate that the cognitive platform treatment is having the desired effect (including to determine the type of tasks and/or CSIs that works for a given user). The analysis can be used to determine whether the cognitive platform should be caused to provide tasks and/or CSIs to enforce or diminish these user results that the EEG is detecting, by adjusting users experience in the application.

In this example and any other example herein, the cData and/or nData can be collected in real-time.

In this example and any other example herein, the adjustments to the type of tasks and/or CSIs can be made in real-time.

Non-limiting examples of the computing device include a smartphone, a tablet, a slate, an e-reader, a digital assistant, or any other equivalent device, including any of the mobile communication devices described hereinabove. As an example, the computing device can include a processor unit that is configured to execute an application that includes an analysis module for analyzing the data indicative of the individual's response to the rendered tasks and/or interference (either or both with computer-implemented time-varying element).

The example systems, methods, and apparatus can be implemented as a component in a product comprising a computing device that uses computer-implemented adaptive psychophysical procedures to assess human performance or delivers psychological/perceptual therapy.

A non-limiting example characteristic of a type of decision boundary metric that can be computed based on the response profile is the response criterion (a time-point measure), calculated using the standard procedure to calculate response criterion for a signal detection psychophysics assessment. See, e.g., Macmillan and Creelman (2004), "Signal Detection: A Users Guide" $2^{nd}$ edition, Lawrence Erlbaum USA.

In other non-limiting examples, the decision boundary metric may be more than a single quantitative measure but rather a curve defined by quantitative parameters based on which decision boundary metrics can be computed, such as but not limited to an area to one side or the other of the response profile curve. Other non-limiting example types of decision boundary metrics that can be computed to characterize the decision boundary curves for evaluating the time-varying characteristics of the decision process include a distance between the initial bias point (the starting point of the belief accumulation trajectory) and the criterion, a distance to the decision boundary, a "waiting cost" (e.g., the distance from the initial decision boundary and the maximum decision boundary, or the total area of the curve to that point), or the area between the decision boundary and the criterion line (including the area normalized to the response deadline to yield a measure of an "average decision boundary" or an "average criterion"). While examples herein may be described based on computation of a response criterion, other types of decision boundary metrics are applicable.

Following is a description of a non-limiting example use of a computational model of human decision-making (based on a drift diffusion model). While the drift diffusion model is used as the example, other types of models apply, including a Bayesian model. The drift-diffusion model (DDM) can be applied for systems with two-choice decision making. See, e.g., Ratcliff, R. (1978), "A theory of memory retrieval." Psychological Review, 85, 59-108; Ratcliff, R., & Tuerlinckx, F. (2002), "Estimating parameters of the diffusion model: Approaches to dealing with contaminant reaction times and parameter variability," Psychonomic Bulletin & Review, 9, 438-481. The diffusion model is based on an assumption that binary decision processes are driven by systematic and random influences.

Figure 5A:
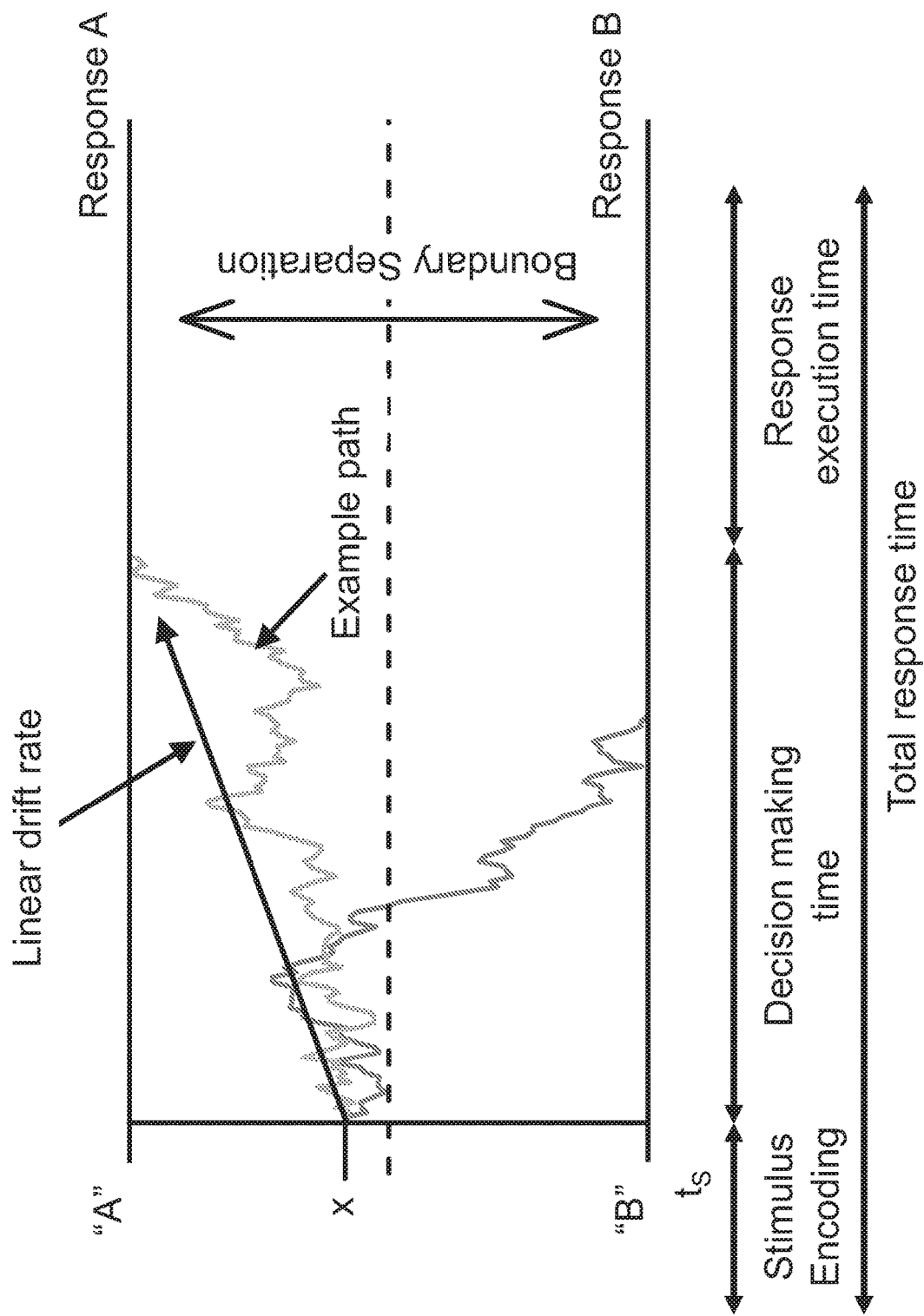
FIG. 5A shows an example graphical depiction of a drift-diffusion model for linear belief accumulation, according to the principles herein.

FIG. 5A shows an example plot of the diffusion model with a stimulus that results in a linear drift rate, showing example paths of the accumulation of belief from a stimulus. It shows the distributions of drift rates across trials for targets (signal) and non-targets (noise). The vertical line is the response criterion. The drift rate on each trial is determined by the distance between the drift criterion and a sample from the drift distribution. The process starts at point x, and moves over time until it reaches the lower threshold at "A" or the upper threshold at "B". The DDM assumes that an individual is accumulating evidence for one or other of the alternative thresholds at each time step, and integrating that evidence to develop a belief, until a decision threshold is reached. Depending on which threshold is reached, different responses (i.e., Response A or Response B) are initiated by the individual. In a psychological application, this means that the decision process is finished and the response system is being activated, in which the individual initiates the corresponding response. As described in non-limiting examples below, this can require a physical action of the individual to actuate a component of the system or apparatus to provide the response (such as but not limited to tapping on the user interface in response to a target). The systematic influences are called the drift rate, and they drive the process in a given direction. The random influences add an erratic fluctuation to the constant path. With a given set of parameters, the model predicts distributions of process durations (i.e., response times) for the two possible outcomes of the process.

FIG. 5A also shows an example drift-diffusion path of the process, illustrating that the path is not straight but rather oscillates between the two boundaries, due to random influences. In a situation in which individuals are required to categorize stimuli, the process describes the ratio of information gathered over time that causes an individual to foster each of the two possible stimulus interpretations. Once belief points with sufficient clarity is reached, the individual initiates a response. In the example of FIG. 5A, processes reaching the upper threshold are indicative of a positive drift rate. In some trials, the random influences can outweigh the drift, and the process terminates at the lower threshold.

Example parameters of the drift diffusion model include quantifiers of the thresholds ("A" or "B"), the starting point (x), the drift rate, and a response time constant (to). The DDM can provide a measure of conservatism, an indication that the process takes more time to reach one threshold and that it will reach the other threshold (opposite to the drift) less frequently. The starting point (x) provides an indicator of bias (reflecting differences in the amount of information that is required before the alternative responses are initiated). If x is closer to "A", an individual requires a smaller (relative) amount of information to develop a belief to execute Response A, as compared with a larger (relative) amount of information that the individual would need to execute Response B. The smaller the distance between the starting point (x) and a threshold, the shorter the process durations would be for the individual to execute the corresponding response. A positive value of drift rate (v) serves as a measure of the mean rate of approach to the upper threshold ("A"). The drift rate indicates the relative amount of information per time unit that the individual absorbs information on a stimulus to develop a belief in order to initiate and execute a response. In an example, comparison of the drift rates computed from data of one individual to data from another can provide a measure of relative perceptual sensitivity of the individuals. In another example, comparison of the drift rates can provide a relative measure of task difficulty. For computation of the response time, the DDM allows for estimating their total duration, and the response time constant ($t_o$) indicates the duration of extra-decisional processes. The DDM has been shown to describe accuracy and reaction times in human data for tasks. In the non-limiting example of FIG. 5A, the total response time is computed as a sum of the magnitude of time for stimulus encoding ($t_s$), the time the individual takes for the decision, and the time for response execution.

As compared to the traditional drift diffusion model that is based on stimuli that result in linear drift rates, the example systems, methods, and apparatus according to the principles herein are configured to render stimuli that result in non-linear drift rates, which stimuli are based on tasks and/or interference (either or both with computer-implemented time-varying element) that are time-varying and have specified response deadlines. As a result, the example systems, methods, and apparatus according to the principles herein are configured to apply a modified diffusion model (modified DDM) based on these stimuli that result in non-linear drift rates.

Figure 5B:
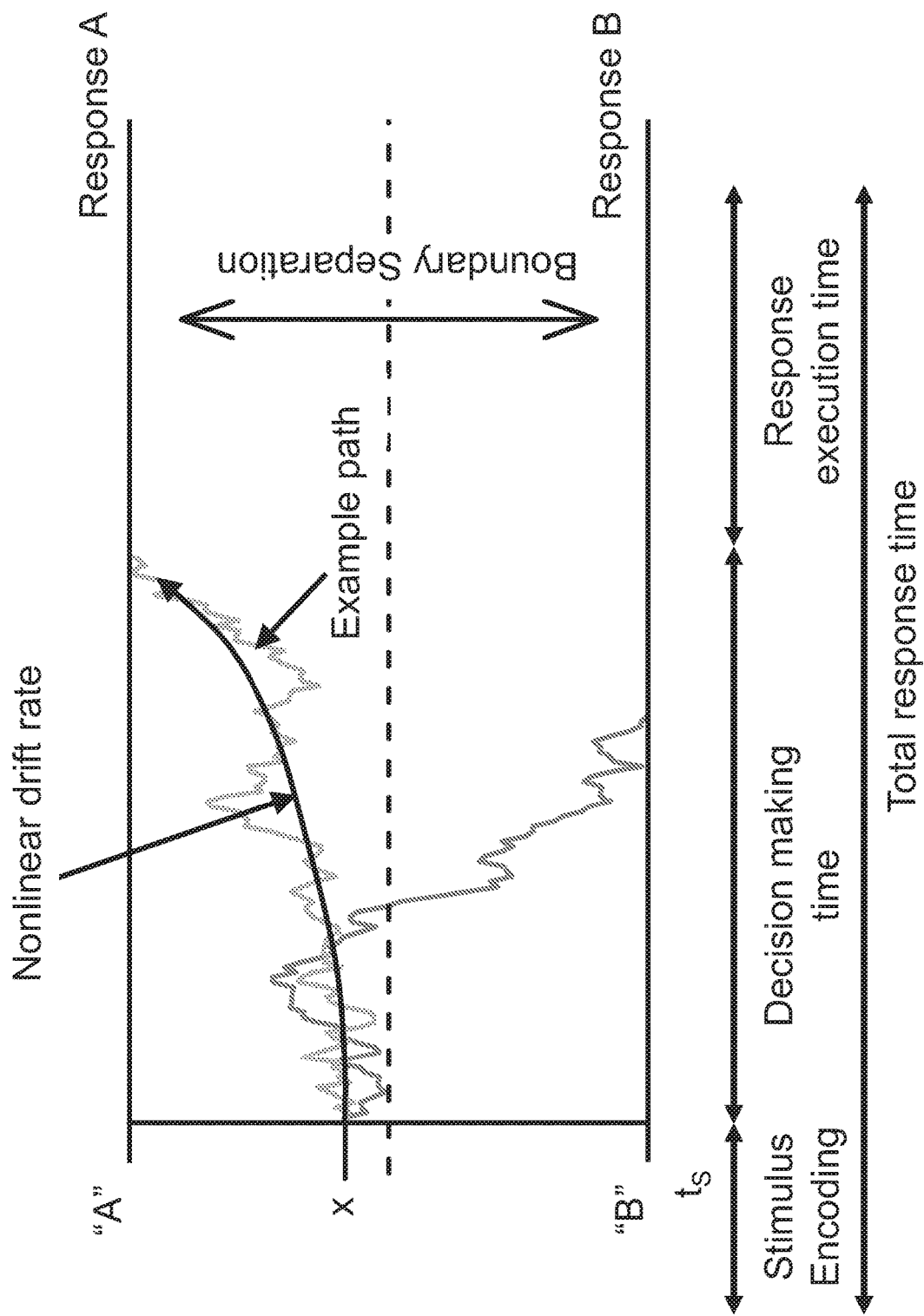
FIG. 5B shows an example graphical depiction of a drift-diffusion model for non-linear belief accumulation, according to the principles herein.

FIG. 5B shows an example plot of a non-linear drift rate in a drift diffusion computation. Example parameters of the modified DDM also include quantifiers of the thresholds ("A" or "B"), the starting point (x), the drift rate, and a response time constant (to). Based on data collected from user interaction with the example systems, methods, and apparatus herein, the systems, methods, and apparatus are configured to apply the modified DDM with the non-linear drift rates to provide a measure of the conservatism or impulsivity of the strategy employed in the user interaction with the example platforms herein. The example systems, methods, and apparatus are configured to compute a measure of the conservatism or impulsivity of the strategy used by an individual based on the modified DDM model, to provide an indication of the time the process takes for a given individual to reach one threshold and as compared to reaching the other threshold (opposite to the drift). The starting point (x) in FIG. 5B also provides an indicator of bias (reflecting differences in the amount of information that is required before the alternative responses are initiated). For computation of the response time, the DDM allows for estimating their total duration, and the response time constant (to) indicates the duration of extra-decisional processes.

In the example systems, methods, and apparatus according to the principles herein, the non-linear drift rate results from the time-varying nature of the stimuli, including (i) the time-varying feature of portions of the task and/or interference (either or both with computer-implemented time-varying element) rendered to the user interface for user response (as a result of which the amount of information available for an individual to develop a belief is presented in a temporally non-linear manner), and (ii) the time limit of the response deadlines of the task and/or interference (either or both with computer-implemented time-varying element), which can influence an individual's sense of timing to develop a belief in order to initiate a response. In this example as well, a positive value of drift rate (v) serves as a measure of the mean rate of approach to the upper threshold ("A"). The non-linear drift rate indicates the relative amount of information per time unit that the individual absorbs to develop a belief in order to initiate and execute a response. In an example, comparison of the drift rate computed from response data collected from one individual to the drift rate computed from response data collected from another individual can be used to provide a measure of relative perceptual sensitivity of the individuals. In another example, comparison of the drift rate computed from response data collected from a given individual from two or more different interaction sessions can be used to provide a relative measure of task difficulty. For computation of the response time of the individual's responses, the modified DDM also allows for estimating the total duration of the response time, and the response time constant ($t_0$) indicates the duration of extra-decisional processes. In the non-limiting example of FIG. 5A, the total response time is computed as a sum of the magnitude of time for stimulus encoding ($t_s$), the time the individual takes for the decision, and the time for response execution.

For the modified DDM, the distance between the thresholds (i.e., between "A" and "B") provides a measure of conservatism—that is, the larger the separation, the more information is collected prior to an individual executing a response. The starting point (x) also provides an estimate of relative conservatism: if the process starts above or below the midpoint between the two thresholds, different amounts of information are required for both responses; that is, a more conservative decision criterion is applied for one response, and a more liberal criterion (i.e., impulsive) for the opposite response. The drift rate (v) indicates the (relative) amount of information gathered per time, denoting either perceptual sensitivity or task difficulty.

Figure 6:
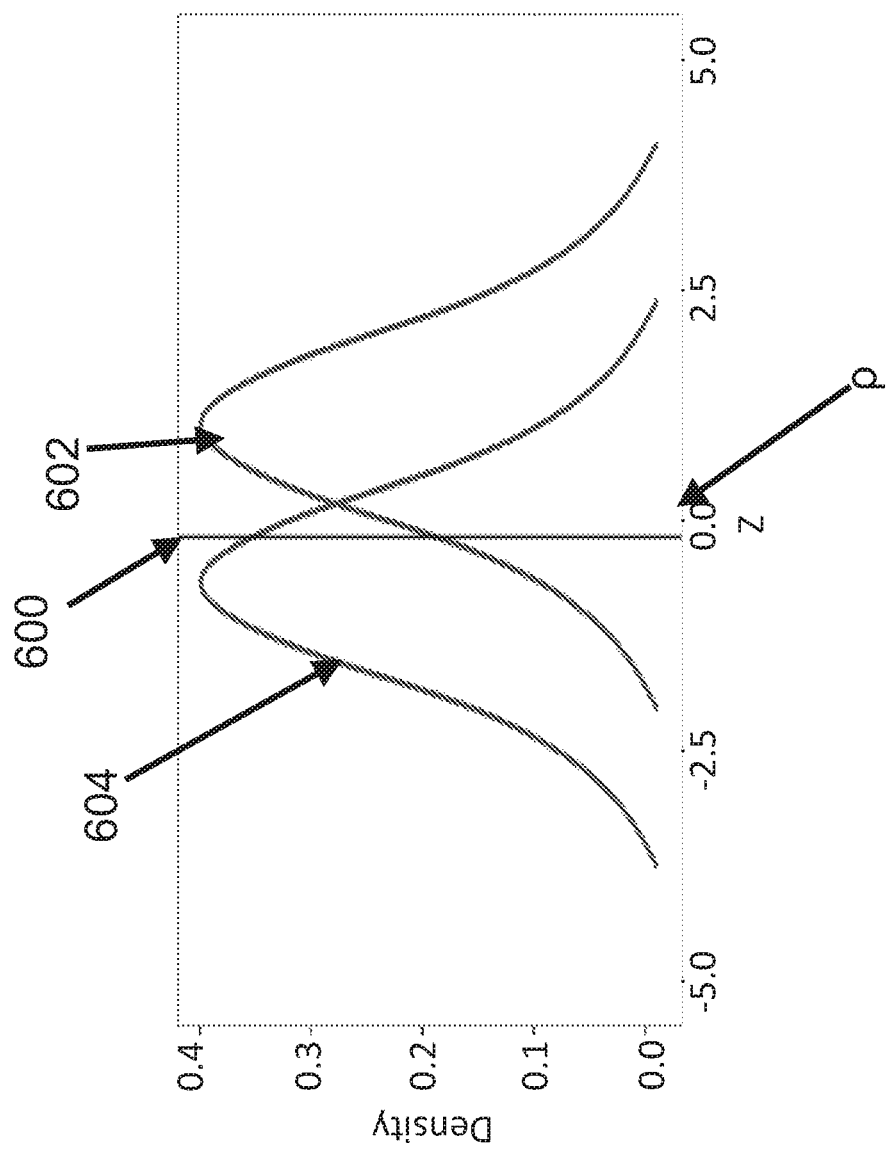
FIG. 6 shows an example plot of the signal and noise based on an example cognitive platform, according to the principles herein.

FIG. 6 shows an example plot of the signal (right curve 602) and noise (left curve 604) distributions of an individual or group psychophysical data, and the computed response criterion 600, based on data collected from an individual's responses with the tasks and/or interference rendered at a user interface of a computing device according to the principles herein (as described in greater detail hereinbelow). The intercept of the criterion line on the X axis (in Z units) can be used to provide an indication of the tendency of an individual to respond 'yes' (further right) or 'no' (further left). The response criterion 600 is positioned to the left side of the zero-bias decision point (p) and to the left side of where the signal and noise distributions intersect. In the non-limiting example of FIG. 6, $\rho$ is the location of the zero-bias decision on the decision axis in Z-units, and response criterion values to the left of $\rho$ indicate an impulsive strategy and response criterion values to the right of $\rho$ indicate a conservative strategy, with intercepts on the zero-bias point indicating a balanced strategy.

The example systems, methods, and apparatus according to the principles herein can be configured to compute a response criterion based on the detection or classification task(s) described herein that are composed of signal and non-signal response targets (as stimuli), in which a user indicates a response that indicates a feature, or multiple features, are present in a series of sequential presentations of stimuli or simultaneous presentation of stimuli.

The data indicative of the results of the classification of an individual according to the principles herein (including a predictive model output) can be transmitted (with the pertinent consent) as a signal to one or more of a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in one or more of an amount, concentration, or dose titration of a drug, biologic or other pharmaceutical agent being or to be administered to the individual and/or to determine an optimal type or combination of drug, biologic or other pharmaceutical agent to be administered to the individual.

The example systems, methods, and apparatus herein provide computerized predictive models, treatment tools, and other tools that can be used by a medical, behavioral, healthcare, or other professional as an aid in an assessment and/or enhancement of an individual's attention, working memory, and goal management. In an example implementation, the example systems, methods, and apparatus herein apply the modified DDM to the collected data to provide measures of conservatism or impulsivity. The example analysis performed using the example systems, methods, and apparatus according to the principles herein can be used to provide measures of attention deficits and impulsivity (including ADHD). The example systems, methods, and apparatus herein provide computerized predictive models, treatment tools, and other tools that can be used as aids in assessment and/or enhancement in other cognitive domains, such as but not limited to attention, memory, motor, reaction, executive function, decision-making, problem-solving, language processing, and comprehension. In some examples, the systems, methods, and apparatus can be used to compute measures for use for cognitive monitoring and/or disease monitoring. In some examples, the systems, methods, and apparatus can be used to compute measures for use for cognitive monitoring and/or disease monitoring during treatment of one or more cognitive conditions and/or diseases and/or executive function disorders.

An example system, method, and apparatus according to the principles herein can be configured to execute an example classifier to generate a quantifier of the cognitive skills in an individual. The example classifier can be built using a machine learning tool, such as but not limited to linear/logistic regression, principal component analysis, generalized linear mixed models, random decision forests, support vector machines, and/or artificial neural networks. In a non-limiting example, classification techniques that may be used to train a classifier using the performance measures of a labeled population of individuals (e.g., individuals with known cognitive disorders, executive function disorder, disease or other cognitive condition). The trained classifier can be applied to the computed values of the performance metric, to generate a classifier output indicative of a measure of cognition, a mood, a level of cognitive bias, or an affective bias of the individual. The trained classifier can be applied to measures of the responses of the individual to the tasks and/or interference (either or both with computer-implemented time-varying element) to classify the individual as to a population label (e.g., cognitive disorder, executive function disorder, disease or other cognitive condition). In an example, machine learning may be implemented using cluster analysis. Each measurement of the cognitive response capabilities of participating individuals can be used as the parameter that groups the individuals to subsets or clusters. For example, the subset or cluster labels may be a diagnosis of a cognitive disorder, cognitive disorder, executive function disorder, disease or other cognitive condition. Using a cluster analysis, a similarity metric of each subset and the separation between different subsets can be computed, and these similarity metrics may be applied to data indicative of an individual's responses to a task and/or interference (either or both with computer-implemented time-varying element) to classify that individual to a subset. In another example, the classifier may be a supervised machine learning tool based on artificial neural networks. In such a case, the performance measures of individuals with known cognitive abilities may be used to train the neural network algorithm to model the complex relationships among the different performance measures. A trained classifier can be applied to the performance/response measures of a given individual to generate a classifier output indicative of the cognitive response capabilities of the individual. Other applicable techniques for generating a classifier include a regression or Monte Carlo technique for projecting cognitive abilities based on his/her cognitive performance. The classifier may be built using other data, including a physiological measure (e.g., EEG) and demographic measures.

In a non-limiting example, classification techniques that may be used to train a classifier using the performance measures of a labeled population of individuals, based on each individual's computed performance metrics, and other known outcome data on the individual, such as but not limited to outcome in the following categories: (i) an adverse event each individual experience in response to administration of a particular pharmaceutical agent, drug, or biologic; (ii) the amount, concentration, or dose titration of a pharmaceutical agent, drug, or biologic, administered to the individuals that resulted in a measurable or characterizable outcome for the individual (whether positive or negative); (iii) any change in the individual's cognitive capabilities based on one or more interactions with the single-tasking and multi-tasking tasks rendered using the computing devices herein; (iv) a recommended treatment regimen, or recommending or determining a degree of effectiveness of at least one of a behavioral therapy, counseling, or physical exercise that resulted in a measurable or characterizable outcome for the individual (whether positive or negative); (v) the performance score of the individual at one or more of a cognitive test or a behavioral test, and (vi) the status or degree of progression of a cognitive condition, a disease or an executive function disorder of the individual. The example classifier can be trained based on the computed values of performance metrics of the known individuals, to be able to classify other yet-to-be classified individuals as to potential outcome in any of the possible categories.

In an example implementation, a programmed processing unit is configured to execute processor-executable instructions to render a task with an interference at a user interface. As described in greater detail herein, one or more of the task and the interference can be time-varying and have a response deadline, such that the user interface imposes a limited time period for receiving at least one type of response from the individual interacting with the apparatus or system. The processing unit is configured to control the user interface to measure data indicative of two or more differing types of responses to the task or to the interference. The programmed processing unit is further configured to execute processor-executable instructions to cause the example system or apparatus to receive data indicative of a first response of the individual to the task and a second response of the individual to the interference, analyze at least some portion of the data to compute at least one response profile representative of the performance of the individual, and determine a decision boundary metric (such as but not limited to the response criterion) from the response profile. The decision boundary metric (such as but not limited to the response criterion) can give a quantitative measure of a tendency of the individual to provide at least one type of response of the two or more differing types of responses (Response A vs. Response B) to the task or the interference. The programmed processing unit is further configured to execute processor-executable instructions to execute a predictive model based on the computed values of the decision boundary metric (such as but not limited to the response criterion), to generate a predictive model output indicative of the cognitive response capabilities of the individual.

In an example, the processing unit further uses the predictive model output for one or more of changing one or more of the amount, concentration, or dose titration of the pharmaceutical agent, drug, biologic or other medication, identifying a likelihood of the individual experiencing an adverse event in response to administration of the pharmaceutical agent, drug, biologic or other medication, identifying a change in the individual's cognitive response capabilities, recommending a treatment regimen, or recommending or determining a degree of effectiveness of at least one of a behavioral therapy, counseling, or physical exercise.

In any example herein, the example predictive model can be used as an intelligent proxy for quantifiable assessments of an individual's cognitive abilities. That is, once a predictive model is trained, the predictive model output can be used to provide the indication of the cognitive response capabilities of multiple individuals without use of other cognitive or behavioral assessment tests.

Monitoring cognitive deficits allows individuals, and/or medical, healthcare, behavioral, or other professional (with consent) to monitor the status or progression of a cognitive condition, a disease, or an executive function disorder. For example, individuals with Alzheimer's disease may shows mild symptoms initially, but others have more debilitating symptoms. If the status or progression of the cognitive symptoms can be regularly or periodically quantified, it can provide an indication of when a form of pharmaceutical agent or other drug may be administered or to indicate when quality of life might be compromised (such as the need for assisted living). Monitoring cognitive deficits also allows individuals, and/or medical, healthcare, behavioral, or other professional (with consent) to monitor the response of the individual to any treatment or intervention, particularly in cases where the intervention is known to be selectively effective for certain individuals. In an example, a cognitive assessment tool based on the predictive models herein can be an individual patient with attention deficit hyperactivity disorder (ADHD). In another example, the predictive models and other tools herein can be used as a monitor of the presence and/or severity of any cognitive side effects from therapies with known cognitive impact, such as but not limited to chemotherapy, or that involve uncharacterized or poorly characterized pharmacodynamics. In any example herein, the cognitive performance measurements and/or predictive model analysis of the data may be performed every 30 minutes, each few hours, daily, two or more times per week, weekly, bi-weekly, each month, or once per year.

In an example, predictive model can be used as an intelligent proxy for quantifiable measures of the performance of the individual.

In a non-limiting example, the task and the interference can be rendered at the user interface such that the individual is required to provide the first response and the second response within a limited period of time. In an example, the individual is required to provide the first response and the second response substantially simultaneously.

In an example, the processing unit executes further instructions including applying at least one adaptive procedure to modify the task and/or the interference, such that analysis of the data indicative of the first response and/or the second response indicates a modification of the first response profile.

In an example, the processing unit controls the user interface to modify a temporal length of the response window associated with the response-deadline procedure.

In an example, the processing unit controls the user interface to modify a time-varying characteristics of an aspect of the task or the interference rendered to the user interface.

As described in connection with FIGS. 3A and 3B, the time-varying characteristics of the task or the interference (e.g., a time-varying target) results in the time-varying of availability of information about the task or interference, respectively, such that that a linear drift-rate is no longer sufficient to capture development of belief over time (rather, requiring a nonlinear drift rate). A time-varying characteristic can be a feature such as, but not limited to, color, shape, type of creature, facial expression, or other feature that an individual requires in order to discriminate between a target and a non-target, resulting in differing time-characteristics of availability. The trial-by-trial adjustment of the response window length also can be a time-varying characteristic that alters the individual's perception of where the decision criteria needs to be in order to respond successfully to a task and/or an interference. Another time-varying characteristic that can be modified is the degree that an interference interferes with a parallel task which can introduce interruptions in belief accumulation and/or response selection and execution.

In an example, modifying the time-varying characteristics of an aspect of the task or the interference includes adjusting a temporal length of the rendering of the task or interference at the user interface between two or more sessions of interactions of the individual.

In an example, the time-varying characteristics can be one or more of a speed of an object, a rate of change of a facial expression, a direction of trajectory of an object, a change of orientation of an object, at least one color of an object, a type of an object, or a size of an object.

In an example, the time-varying characteristics can be the rate of change or modulation in content and/or appearance of the computer-implemented time-varying elements, including one or more of a rate of change of the increase or decrease in the number of features included in the computer-implemented time-varying element, a rate of change of the types of features included in the computer-implemented time-varying element, and/or a rate of change of the speed or trajectory of movement of the features included in the computer-implemented time-varying element.

In an example, the change in type of object is effected using morphing from a first type of object to a second type of object or rendering a blendshape as a proportionate combination of the first type of object and the second type of object.

In a non-limiting example, the processing unit can be configured to render a user interface or cause another component to execute least one element for indicating a reward to the individual for a degree of success in interacting with a task and/or interference, or another feature or other element of a system or apparatus. A reward computer element can be a computer-generated feature that is delivered to a user to promote user satisfaction with the example system, method or apparatus, and as a result, increase positive user interaction and hence enjoyment of the experience of the individual.

In an example, the processing unit further computes as the predictive model output parameters indicative of one or more of a bias sensitivity derived from the data indicative of the first response and the second response, a non-decision time sensitivity to parallel tasks, a belief accumulation sensitivity to parallel task demands, a reward rate sensitivity, or a response window estimation efficiency. Bias sensitivity can be a measure of how sensitive an individual is to certain of the tasks based on their bias (tendency to one type of response versus another (e.g., Response A vs. Response B)). Non-decision time sensitivity to parallel tasks can be a measure of how much the interference interferes with the individual's performance of the primary task. Belief accumulation sensitivity to parallel task demands can be a measure of the rate of the individual to develop/accumulate belief for responding to the interference during the individual's performance of the primary task. Reward rate sensitivity can be used to measure how an individual's response changes based on the temporal length of the response deadline window. When near the end of a response deadline window (e.g., as individual sees interference about to move off the field of view), the individual realizes that he is running out of time to make a decision. This measures how the individual's responses change accordingly. Response window estimation efficiency is explained as follows. When the individual is making a decision to act/respond or not act/no response, the decision needs to be based on when the individual thinks his time to respond is running out. For a varying window, the individual will not be able to measure that window perfectly, but with enough trials/session, based the response data, it may be possible to infer how good the individual is at making that estimation based on the time-varying aspect (e.g., trajectory) of the objects in the task or interference.

An example system, method, and apparatus according to the principles herein can be configured to train a predictive model of a measure of the cognitive capabilities of individuals based on feedback data from the output of the computational model of human decision-making for individuals that are previously classified as to the measure of cognitive abilities of interest. For example, a classifier can be trained using a plurality of training datasets, where each training dataset is associated with a previously classified individual from a group of individuals. Each of the training dataset includes data indicative of the first response of the classified individual to the task and data indicative of the second response of the classified individual to the interference, based on the classified individual's interaction with an example apparatus, system, or computing device described herein. The example classifier also can take as input data indicative of the performance of the classified individual at a cognitive test, and/or a behavioral test, and/or data indicative of a diagnosis of a status or progression of a cognitive condition, a disease, or a disorder (including an executive function disorder) of the classified individual.

In any example herein, the at least one processing unit can be programmed to cause an actuating component of the apparatus (including the cognitive platform) to effect auditory, tactile, and/or vibrational computerized elements to effect the stimulus or other interaction with the individual. In a non-limiting example, the at least one processing unit can be programmed to cause a component of the cognitive platform to receive data indicative of at least one response from the individual based on the user interaction with the task and/or interference, including responses provided using an input device. In an example where at least one graphical user interface is rendered to present the computerized stimulus to the individual, the at least one processing unit can be programmed to cause the graphical user interface to receive the data indicative of at least one response from the individual.

In any example herein, the data indicative of the response of the individual to a task and/or an interference can be measured using at least one sensor device contained in and/or coupled to an example system or apparatus herein, such as but not limited to a gyroscope, an accelerometer, a motion sensor, a position sensor, a pressure sensor, an optical sensor, an auditory sensor, a vibrational sensor, a video camera, a pressure-sensitive surface, a touch-sensitive surface, or other type of sensor. In other examples, the data indicative of the response of the individual to the task and/or an interference can be measured using other types of sensor devices, including a video camera, a microphone, joystick, keyboard, a mouse, a treadmill, elliptical, bicycle, steppers, or a gaming system (including a Wii®, a Playstation®, or an Xbox® or other gaming system). The data can be generated based on physical actions of the individual that are detected and/or measured using the at least one sensor device, as the individual executed a response to the stimuli presented with the task and/or interference.

The user may respond to tasks by interacting with the computer device. In an example, the user may execute a response using a keyboard for alpha-numeric or directional inputs; a mouse for GO/NO-GO clicking, screen location inputs, and movement inputs; a joystick for movement inputs, screen location inputs, and clicking inputs; a microphone for audio inputs; a camera for still or motion optical inputs; sensors such as accelerometer and gyroscopes for device movement inputs; among others. Non-limiting example inputs for a game system include but are not limited to a game controller for navigation and clicking inputs, a game controller with accelerometer and gyroscope inputs, and a camera for motion optical inputs. Example inputs for a mobile device or tablet include a touch screen for screen location information inputs, virtual keyboard alpha-numeric inputs, go/no go tapping inputs, and touch screen movement inputs; accelerometer and gyroscope motion inputs; a microphone for audio inputs; and a camera for still or motion optical inputs, among others. In other examples, data indicative of the individual's response can include physiological sensors/measures to incorporate inputs from the user's physical state, such as but not limited to electroencephalogram (EEG), magnetoencephalography (MEG), heart rate, heart rate variability, blood pressure, weight, eye movements, pupil dilation, electrodermal responses such as the galvanic skin response, blood glucose level, respiratory rate, and blood oxygenation.

In any example herein, the individual may be instructed to provide a response via a physical action of clicking a button and/or moving a cursor to a correct location on a screen, head movement, finger or hand movement, vocal response, eye movement, or other action of the individual.

As a non-limiting example, an individual's response to a task or interference rendered at the user interface that requires a user to navigate a course or environment or perform other visuo-motor activity may require the individual to make movements (such as but not limited to steering) that are detected and/or measured using at least one type of the sensor device. The data from the detection or measurement provides the response to the data indicative of the response.

As a non-limiting example, an individual's response to a task or interference rendered at the user interface that requires a user to discriminate between a target and a non-target may require the individual to make movements (such as but not limited to tapping or other spatially or temporally discriminating indication) that are detected and/or measured using at least one type of the sensor device. The data that is collected by a component of the system or apparatus based on the detection or other measurement of the individual's movements (such as but not limited to at least one sensor or other device or component described herein) provides the data indicative of the individual's responses.

The example system, method, and apparatus can be configured to apply the predictive model, using computational techniques and machine learning tools, such as but not limited to linear/logistic regression, principal component analysis, generalized linear mixed models, random decision forests, support vector machines, or artificial neural networks, to the data indicative of the individual's response to the tasks and/or interference, and/or data from one or more physiological measures, to create composite variables or profiles that are more sensitive than each measurement alone for generating a predictive model output indicative of the cognitive response capabilities of the individual. In an example, the predictive model output can be configured for other indications such as but not limited to detecting an indication of a disease, disorder or cognitive condition, or assessing cognitive health.

The example predictive models herein can be trained to be applied to data collected from interaction sessions of individuals with the cognitive platform to provide the output. In a non-limiting example, the predictive model can be used to generate a standards table, which can be applied to the data collected from the individual's response to task and/or interference to classify the individual's cognitive response capabilities.

Non-limiting examples of assessment of cognitive abilities include assessment scales or surveys such as the Mini Mental State Exam, CANTAB cognitive battery, Test of Variables of Attention (TOVA), Repeatable Battery for the Assessment of Neuropsychological Status, Clinical Global Impression scales relevant to specific conditions, Clinician's Interview-Based Impression of Change, Severe Impairment Battery, Alzheimer's Disease Assessment Scale, Positive and Negative Syndrome Scale, Schizophrenia Cognition Rating Scale, Conners Adult ADHD Rating Scales, Hamilton Rating Scale for Depression, Hamilton Anxiety Scale, Montgomery-Asberg Depressing Rating scale, Young Mania Rating Scale, Children's Depression Rating Scale, Penn State Worry Questionnaire, Hospital Anxiety and Depression Scale, Aberrant Behavior Checklist, Activities for Daily Living scales, ADHD self-report scale, Positive and Negative Affect Schedule, Depression Anxiety Stress Scales, Quick Inventory of Depressive Symptomatology, and PTSD Checklist.

In other examples, the assessment may test specific functions of a range of cognitions in cognitive or behavioral studies, including tests for perceptive abilities, reaction and other motor functions, visual acuity, long-term memory, working memory, short-term memory, logic, and decision-making, and other specific example measurements, including but are not limited to TOVA, MOT (motion-object tracking), SART, CDT (Change detection task), UFOV (useful Field of view), Filter task, WAIS digit symbol, Troop, Simon task, Attentional Blink, N-back task, PRP task, task-switching test, and Flanker task.

In non-limiting examples, the example systems, methods, and apparatus according to the principles described herein can be applicable to many different types of neuropsychological conditions, such as but not limited to dementia, Parkinson's disease, cerebral amyloid angiopathy, familial amyloid neuropathy, Huntington's disease, or other neurodegenerative condition, autism spectrum disorder (ASD), presence of the 16p11.2 duplication, and/or an executive function disorder, such as but not limited to attention deficit hyperactivity disorder (ADHD), sensory-processing disorder (SPD), mild cognitive impairment (MCI), Alzheimer's disease, multiple-sclerosis, schizophrenia, major depressive disorder (MDD), or anxiety (including social anxiety), bipolar disorder, post-traumatic stress disorder, schizophrenia, dementia, Alzheimer's disease, or multiple-sclerosis.

The instant disclosure is directed to computer-implemented devices formed as example cognitive platforms configured to implement software and/or other processor-executable instructions for the purpose of measuring data indicative of a user's performance at one or more tasks, to provide a user performance metric. The example performance metric can be used to derive an assessment of a user's cognitive abilities and/or to measure a user's response to a cognitive treatment, and/or to provide data or other quantitative indicia of a user's condition (including physiological condition and/or cognitive condition). Non-limiting example cognitive platforms according to the principles herein can be configured to classify an individual as to a neuropsychological condition, autism spectrum disorder (ASD), presence of the 16p11.2 duplication, and/or an executive function disorder, and/or potential efficacy of use of the cognitive platform when the individual is being administered (or about to be administered) a drug, biologic or other pharmaceutical agent, based on the data collected from the individual's interaction with the cognitive platform and/or metrics computed based on the analysis (and associated computations) of that data. Yet other non-limiting example cognitive platforms according to the principles herein can be configured to classify an individual as to likelihood of onset and/or stage of progression of a neuropsychological condition, including as to a neurodegenerative condition, based on the data collected from the individual's interaction with the cognitive platform and/or metrics computed based on the analysis (and associated computations) of that data. The neurodegenerative condition can be, but is not limited to, Alzheimer's disease, dementia, Parkinson's disease, cerebral amyloid angiopathy, familial amyloid neuropathy, or Huntington's disease.

Any classification of an individual as to likelihood of onset and/or stage of progression of a neurodegenerative condition according to the principles herein can be transmitted as a signal to a medical device, healthcare computing system, or other device, and/or to a medical practitioner, a health practitioner, a physical therapist, a behavioral therapist, a sports medicine practitioner, a pharmacist, or other practitioner, to allow formulation of a course of treatment for the individual or to modify an existing course of treatment, including to determine a change in dosage of a drug, biologic or other pharmaceutical agent to the individual or to determine an optimal type or combination of drug, biologic or other pharmaceutical agent to the individual.

In any example herein, the cognitive platform can be configured as any combination of a medical device platform, a monitoring device platform, a screening device platform, or other device platform.

The instant disclosure is also directed to example systems that include cognitive platforms that are configured for coupling with one or more physiological or monitoring component and/or cognitive testing component. In some examples, the systems include cognitive platforms that are integrated with the one or more other physiological or monitoring component and/or cognitive testing component. In other examples, the systems include cognitive platforms that are separately housed from and configured for communicating with the one or more physiological or monitoring component and/or cognitive testing component, to receive data indicative of measurements made using such one or more components.

In an example system, method, and apparatus herein, the processing unit can be programmed to control the user interface to modify a temporal length of the response window associated with a response-deadline procedure.

In an example system, method, and apparatus herein, the processing unit can be configured to control the user interface to modify a time-varying characteristics of an aspect of the task or the interference rendered to the user interface. For example, modifying the time-varying characteristics of an aspect of the task or the interference can include adjusting a temporal length of the rendering of the task or interference at the user interface between two or more sessions of interactions of the individual. As another example, the time-varying characteristics is one or more of a speed of an object, a rate of change of a facial expression, a direction of trajectory of an object, a change of orientation of an object, at least one color of an object, a type of an object, or a size of an object. In any example herein, the foregoing time-varying characteristic can be applied to an object that includes the computer-implemented time-varying element to modify a cognitive or emotional load of the individual's interaction with the apparatus (e.g., computing device or cognitive platform).

In any example herein, based on the physiological measurement data, the processing unit can be configured to control the user interface to modify (adjust) a time-varying characteristics of an aspect of the task or the interference rendered to the user interface. For example, based on physiological measurement data indicating lack of attentiveness or user engagement, the time-varying characteristics of an aspect of the task or the interference can be changed to derive greater attentiveness or user engagement (i.e., until the physiological measurement indicates the desired level of attentiveness or user engagement). The modification of the time-varying characteristics of an aspect of the task or the interference can be adjusted and changed, based on a feedback loop, such that the physiological measurement data indicates that the desired level of attentiveness or user engagement is derived. The feedback loop can be implemented using one or more controllers, such as but not limited to a proportional controller, a proportional/integral controller, a proportional/differential controller, or a proportional/integral/differential (PID) controller. Based on the analysis of the data indicative of the physiological measurement, the one or more controllers can be applied to issue control signals to effect the feedback loop, i.e., to continuously adjust the time-varying characteristics of an aspect of the task or the interference presented to the user, until the physiological measurements of the individual indicate signals of a sufficient level of user engagement.

In a non-limiting example, the processing unit can be configured to use for the analysis only the data from measurements of the individual's performance of the tasks and/or interference made during the time intervals of the physiological measurement indicating more focused attention or higher user engagement to compute the performance metrics for the individual, such as but not limited to a decision boundary metric or the interference cost. In another non-limiting example, the processing unit can be configured to apply differing weighting factors to subsets the data from measurements of the individual's performance of the tasks and/or interference made during the time intervals of the physiological measurement indicating more focused attention or higher user engagement as compared to time intervals of less focused attention, prior to computing the performance metrics for the individual, such as but not limited to a decision boundary metric or the interference cost. In another non-limiting example, the processing unit can be configured to use physiological measurements indicating more focused attention or higher user engagement in a first trial or session to modify (adjust) time-varying characteristics or other characteristics of the tasks and/or interference in a subsequent trial or session, e.g., using one or more controllers to effect a feedback loop, such that physiological measurements from the individual in the subsequent trial or session indicates more focused attention or higher user engagement of the individual during interaction with the tasks and/or interference. The physiological measurement indicative of more focused attention or higher user engagement may be collected either during a previous session of the individual's interaction with the tasks and/or interference or based on preset thresholds of aggregated physiological measurement data collected based on the interaction of two or more individuals (up to a group or population) with the task and/or interference.

In a non-limiting example, the processing unit can be configured to adjusting the tasks and/or interference based on the one or more physiological measurements, such that the individual is accelerated towards, or held back from, achieving a certain goal or crossing a performance gate or other milestone in a trial or session, to derive physiological profile indicating more focused attention or higher user engagement.

In a non-limiting example, the performance of the physiological measurements can be asynchronous with the individual's interactions with the tasks and/or interference, such as before and/or after the individual interacts with the tasks and/or interference. The physiological profile from the one or more asynchronous physiological measurements can be used for computation of the performance metric(s).

In a non-limiting example, the performance of the physiological measurements can be synchronous with the individual's interactions with the tasks and/or interference, such as overlapping in time with at least a portion of the individual interactions with the tasks and/or interference. The physiological profile from the one or more synchronous physiological measurements can be used for computation of the performance metric(s).

In a non-limiting example, the measurements of the individual's responses to multiple iterations, i.e., multiple subsequent renderings, of the tasks and/or interference, coupled with the synchronous or asynchronous physiological measurement, can be aggregated to provide a combined or refined performance metric of the individual.

In an example, a composite performance metric of the performance of the individual's performance of multiple iterations of the tasks and/or interference can be computed based on (i) the data indicative of the individual's responses to two or more instances of the primary task with (i.e., in the presence of) the interference relative to the at least one physiological profile, and/or (ii) the data indicative of the individual's responses to two or more instances of the primary task without (i.e., in the absence of) the interference relative to the at least one physiological profile. The at least one physiological profile can be determined based on one or more measurements of at least one physiological component, the at least one physiological component being coupled to measure a physiological measure of the individual. The example physiological measurements can include at least one synchronous physiological measurement, or at least one asynchronous physiological measurement, or a combination of the two different types of measurements.

In a non-limiting example, the processing unit can be configured to delay the rendering of tasks and/or interference until one or more physiological measurements indicate that the individual is at the desired level of focused attention or user engagement (e.g., as determined based on the physiological profile).

In a non-limiting example, the processing unit can be configured to delay the rendering of tasks and/or interference until one or more physiological measurements indicate that the individual is exhibiting a desired state, such as but not limited to greater state of attention or engagement, less of a heightened state, less stress, or less aggression, less heart rate variability. As a non-limiting example, for an individual with autism, the interactions with the tasks and/or interference is more beneficial if the individual is in a desired state. The processing unit can be configured to analyze the physiological measurements (or use the physiological profile) to determine whether a desired state of the individual is achieved, prior to rendering the tasks and/or interference, modulating the parameters of the tasks and/or interference (including the time-varying characteristics), and/or varying the type or amount of rewards (e.g., number or types of reward stars) presented to the individual based on the interactions with the tasks and/or interference.

In an example system, method, and apparatus herein, the change in type of object is effected using morphing from a first type of object to a second type of object or rendering a blendshape as a proportionate combination of the first type of object and the second type of object.

In an example system, method, and apparatus herein, the processing unit can be further programmed to compute as the predictive model output parameters indicative of one or more of a bias sensitivity derived from the data indicative of the first response and the second response, a non-decision time sensitivity to parallel tasks, a belief accumulation sensitivity to parallel task demands, a reward rate sensitivity, or a response window estimation efficiency.

In an example system, method, and apparatus herein, the processing unit can be further programmed to control the user interface to render the task as a continuous visuo-motor tracking task.

In an example system, method, and apparatus herein, the processing unit controls the user interface to render the interference as a target discrimination task.

As used herein, a target discrimination task may also be referred to as a perceptual reaction task, in which the individual is instructed to perform a two-feature reaction task including target stimuli and non-target stimuli through a specified form of response. As a non-limiting example, that specified type of response can be for the individual to make a specified physical action in response to a target stimulus (e.g., move or change the orientation of a device, tap on a sensor-coupled surface such as a screen, move relative to an optical sensor, make a sound, or other physical action that activates a sensor device) and refrain from making such specified physical action in response to a non-target stimulus.

In a non-limiting example, the individual is required to perform a visuomotor task (as a primary task) with a target discrimination task as an interference (secondary task) (either or both including a computer-implemented time-varying element). To effect the visuomotor task, a programmed processing unit renders visual stimuli that require fine motor movement as reaction of the individual to the stimuli. In some examples, the visuomotor task is a continuous visuomotor task. The processing unit is programmed to alter the visual stimuli and recording data indicative of the motor movements of the individual over time (e.g., at regular intervals including 1, 5, 10, or 30 times per second). Example stimuli rendered using the programmed processing unit for a visuomotor task requiring fine motor movement may be a visual presentation of a path that an avatar is required to remain within. The programmed processing unit may render the path with certain types of obstacles that the individual is either required to avoid or to navigate towards. In an example, the fine motor movements effect by the individual, such as but not limited to tilting or rotating a device, are measured using an accelerometer and/or a gyroscope (e.g., to steer or otherwise guide the avatar on the path while avoiding or crossing the obstacles as specified). The target discrimination task (serving as the interference), can be based on targets and non-targets that differ in shape and/or color.

In any example, the apparatus may be configured to instruct the individual to provide the response to the computer-implemented time-varying element as an action that is read by one or more sensors (such as a movement that is sensed using a gyroscope or accelerometer or a motion or position sensor, or a touch that is sensed using a touch-sensitive, pressure sensitive or capacitance-sensitive sensor.

In some examples, the task and/or interference can be a visuomotor task, a target discrimination task, and/or a memory task.

Within the context of a computer-implemented adaptive response-deadline procedure, the response-deadline can be adjusted between trials or blocks of trials to manipulate the individual's performance characteristics towards certain goals. A common goal is driving the individual's average response accuracy towards a certain value by controlling the response deadline.

In a non-limiting example, the hit rate may be defined as the number of correct responses to a target stimuli divided by the total number of target stimuli presented, or the false alarm rate (e.g., the number of responses to a distractor stimuli divided by the number of distractor stimuli presented), the miss rate (e.g., the number of nonresponses to a target stimuli divided by the number of incorrect responses, including the nonresponses to a target stimuli added to the number of responses to a distractor stimuli), the correct response rate (the proportion of correct responses not containing signal). In an example, the correct response rate may be calculated as the number of non-responses to the distractor stimuli divided by the number of non-responses to the distractor stimuli plus the number of responses to the target stimuli.

An example system, method, and apparatus according to the principles herein can be configured to apply adaptive performance procedures to modify measures of performance to a specific stimulus intensity.

In some examples, the adaptive procedure can be based on a computational model of human decision-making (such as but not limited to the modified DDM), predictive models built from outputs of such models, and the analysis described herein based on the output of the computational model, can be more quantitatively informative on individual differences or on changes in sensitivity to a specific stimulus level. The performance metric provides a flexible tool for determining a performance of the individual. Accordingly, an adaptation procedure based on performance metric measurements at the individual or group level become a desirable source of information about the changes in performance at the individual or group level over time with repeated interactions with the tasks and computer-implemented time-varying elements described herein, and measurements of the individual's responses with the interactions.

In some examples, the procedure can be adapted based on a percent correct (PC) signal detection metric of sensitivity to a target. In an example system, the value of percent correct (i.e., percent of correct responses of the individual to a task or computer-implemented time-varying element) may be used in the adaptive algorithms as the basis for adapting the stimulus level of tasks and/or interferences rendered at the user interface for user interaction from one trial to another.

In some examples, the tasks and/or interference are presented to the individual in two or more trials and/or sessions, with an interspersed interval between each trial and/or session. In some examples, the computing system is configured to implement the tasks and/or interference in the subsequent trial(s) and/or session(s) at a difficulty level that is changed or maintained the same from one trial to another and/or from one session to another. For example, the difficulty level in each subsequent trial and/or each subsequent session can be dependent on the performance of the individual in the previous trial and/or previous session. Based on an analysis by the computing system indicating that the number of correct inputs in the responses made by the individual in a previous trial and/or session increases or reaches a specific threshold (e.g. a pre-determined percentage of correct responses), the computing system is configured to implement the tasks and/or interference in the subsequent trial and/or session at a higher difficulty level than the previous trial and/or session. Based on an analysis by the computing system indicating that the number of correct inputs in the responses made by the individual is decreased, is at or below a specified threshold, achieves a specified level of failure, or fails to achieve a level of success, in the previous trial and/or session, the computing system is configured to implement the tasks and/or interference in the subsequent trial and/or session at a lower difficulty level than the previous trial and/or session. In some examples, the computing system is configured to implement the tasks and/or interference in the subsequent trial(s) and/or session(s) at a difficulty level in a step-wise and/or in a peaks and valley fashion.

To modulate the difficulty level of a trial and/or a session, the computing system can be configured to modify the difficulty level of the primary task, or of the interference, or of some combination of the primary task and the interference. The modulation of the difficulty level may be based on either the data indicative of the actual performance of the individual in performing the task or interference (as determined by measurement as the input to a task or interference) or a more indirect parameter governed by the analysis, e.g., a performance metric such as but not limited to the interference cost (described in greater detail below) or a decision boundary metric.

In another example, the computing system can be configured to modify the difficulty level such that the platform is specifically tailored to an individual, e.g., by maintaining the difficulty level at or around a threshold success rate for the individual. For example, the computing system can be configured to target the difficulty level to maintain a substantially constant error rate from an individual (e.g., to maintain substantially approximately 80% response accuracy). In other examples, the computing system can be configured to target the difficulty level to maintain an accuracy of performance from the individual of about 50%, about 55%, about 60%, about 65%, about 70%, about 75%, about 80%, about 85%, or about 90% or more. The difficulty level of a task for a given individual may be determined by implementing the task without interference (e.g., single-tasking) initially at a default difficulty level for a category of individuals (e.g. average for an age range), a lowest level of difficulty, or a level comparable based on the individual's prior assessment. In subsequent trials and/or sessions, the difficulty level can be change until analysis of the measured data indicates that the individual is performing at a specific threshold level (e.g., percent accuracy).

In any example herein, the computing system can be configured to modify the difficulty level using adaptive thresholding methods, such as but not limited to using psychometric staircase algorithms, to dynamically and rapidly maintain the performance of the individual at a specific performance level. For example, the thresholding algorithm can be implemented to achieve as close to about 80% accuracy in the performance of the individual in the primary task (such as but not limited to a visuomotor tracking task) and/or the interference (such as but not limited to a target discrimination (or target detection) task) from the individual by adjusting the difficulty levels appropriately.

Executive function training, such as that delivered by the example systems, methods, and apparatus described herein can be configured to apply an adaptive algorithm to modify the stimulus levels (including cognitive or emotional load based on the computer-implemented time-varying element(s) implemented) between trials, to move a user's performance metric to the desired level (value), depending on the needs or preference of the individual or based on the clinical population receiving the treatment.

The example systems, methods, and apparatus described herein can be configured to apply an adaptive algorithm that is adapted based on the computed performance metric as described herein to modify the difficulty levels of the tasks and/or interference (either or both including a computer-implemented time-varying element) rendered at the user interface for user interaction from one trial to another.

In an example, the task and/or interference (either or both including a computer-implemented time-varying element) can be modified/adjusted/adapted based on an iterative estimation of metrics by tracking current estimates and selecting the features, trajectory, and response window of the targeting task, and level/type of parallel task interference for the next trial in order to maximize information the trial can provide.

In some examples, the task and/or interference (either or both including a computer-implemented time-varying element) are adaptive tasks. The task and/or interference can be adapted or modified in difficulty level based on the performance metric, as described hereinabove. Such difficulty adaptation may be used to determine the ability of the participant.

In an example, the difficulty of the task (potentially including a computer-implemented time-varying element) adapts with every stimuli that is presented, which could occur more often than once at regular time intervals (e.g., every 5 seconds, every 10 seconds, every 20 seconds or other regular schedule).

In another example, the difficulty of a continuous task (potentially including a computer-implemented time-varying element) can be adapted on a set schedule, such as but not limited to every 30 seconds, 10 seconds, 1 second, 2 times per second, or 30 times per second.

In an example, the length of time of a trial depends on the number of iterations of rendering (of the tasks/interference) and receiving (of the individual's responses) and can vary in time. In an example, a trial can be on the order of about 500 milliseconds, about 1 second (s), about 10 s, about 20 s, about 25 s, about 30 s, about 45 s, about 60 s, about 2 minutes, about 3 minutes, about 4 minutes, about 5 minutes, or greater. Each trial may have a pre-set length or may be dynamically set by the processing unit (e.g., dependent on an individual's performance level or a requirement of the adapting from one level to another).

In an example, the task and/or interference (either or both including a computer-implemented time-varying element) can be modified based on targeting changes in one or more specific metrics by selecting features, trajectory, and response window of the targeting task, and level/type of parallel task interference to progressively require improvements in those metrics in order for the apparatus to indicate to an individual that they have successfully performed the task. This could include specific reinforcement, including explicit messaging, to guide the individual to modify performance according to the desired goals.

In an example, the task and/or interference (either or both including a computer-implemented time-varying element) can be modified based on a comparison of an individual's performance with normative data or a computer model or taking user input (the individual performing the task/interference or another individual such as a clinician) to select a set of metrics to target for changing in a specific order, and iteratively modifying this procedure based on the subject's response to treatment. This could include feedback to the individual performing the task/interference or another individual to serve as notification of changes to the procedure, potentially enabling them to approve or modify these changes before they take effect.

In various examples, the difficulty level may be kept constant or may be varied over at least a portion of a session in an adaptive implementation, where the adaptive task (primary task or secondary task) increases or decreases in difficulty based on the performance metric.

An example system, method, and apparatus according to the principles herein can be configured to enhance the cognitive skills in an individual. In an example implementation, a programmed processing unit is configured to execute processor-executable instructions to render a task with an interference at a user interface. As described in greater detail herein, one or more of the task and the interference (either or both including a computer-implemented time-varying element) can be time-varying and have a response deadline, such that the user interface imposes a limited time period for receiving at least one type of response from the individual interacting with the apparatus or system.

An example processing unit is configured to control the user interface to render a first instance of a task with an interference at the user interface, requiring a first response from the individual to the first instance of the task in the presence of the interference and a response from the individual to at least one computer-implemented time-varying element. Either or both of the first instance of the task and the interference includes at least one a computer-implemented time-varying element. The user interface can be configured to measure data indicative of the response of the individual to the at least one computer-implemented time-varying element, the data including at least one measure of cognitive capabilities of the individual. The example processing unit is configured to measure substantially simultaneously the first response from the individual to the first instance of the task and the response from the individual to the at least one computer-implemented time-varying element, and to receive data indicative of the first response and the response of the individual to the at least one computer-implemented time-varying element. The example processing unit is also configured to analyze the data indicative of the first response and the response of the individual to the at least one computer-implemented time-varying element to compute at least one performance metric comprising at least one quantified indicator of cognitive abilities of the individual.

In an example, the indication of the modification of the cognitive response capabilities can be based on observation of a change in a measure of a degree of impulsiveness or conservativeness of the individual's cognitive response capabilities.

In an example, the indication of the modification of the cognitive abilities can include a change in a measure of one or more of affective bias, mood, level of cognitive bias, sustained attention, selective attention, attention deficit, impulsivity, inhibition, perceptive abilities, reaction and other motor functions, visual acuity, long-term memory, working memory, short-term memory, logic, and decision-making.

In an example, adapting the task and/or interference based on the first performance metric includes one or more of modifying the temporal length of the response window, modifying a type of reward or rate of presentation of rewards to the individual, and modifying a time-varying characteristic of the task and/or interference (including the computer-implemented time-varying element).

In an example, modifying the time-varying characteristics of an aspect of the task or the interference (including the computer-implemented time-varying element) can include adjusting a temporal length of the rendering of the task or interference at the user interface between two or more sessions of interactions of the individual.

In an example, the time-varying characteristics can include one or more of a speed of an object, a rate of change of a facial expression, a direction of trajectory of an object, a change of orientation of an object, at least one color of an object, a type of an object, or a size of an object, or modifying a sequence or balance of rendering of targets versus non-targets at the user interface.

In an example, the change in type of object is effected using morphing from a first type of object to a second type of object or rendering a blendshape as a proportionate combination of the first type of object and the second type of object.

Designing the computer-implemented adaptive procedure using a goal of explicitly measuring the shape and/or area of the decision boundary, the response deadlines can be adjusted to points where measurements produce maximal information of use for defining this boundary. These optimal deadlines may be determined using an information theoretic approach to minimize the expected information entropy.

Example systems, methods and apparatus according to the principles herein can be implemented using a programmed computing device including at least one processing unit, to determine a potential biomarker for clinical populations.

Example systems, methods and apparatus according to the principles herein can be implemented using a programmed computing device including at least one processing unit to measure change in response profile in individuals or groups after use of an intervention.

Example systems, methods and apparatus according to the principles herein can be implemented using a programmed computing device including at least one processing unit to apply the example metrics herein, to add another measurable characteristic of individual or group data that can be implemented for greater measurement of psychophysical-threshold accuracy and assessment of response profile to computer-implemented adaptive psychophysical procedures.

Example systems, methods and apparatus according to the principles herein can be implemented using a programmed computing device including at least one processing unit to apply the example metrics herein to add a new dimension to available data that can be used to increase the amount of information harvested from psychophysical testing.

An example system, method, and apparatus according to the principles herein can be configured to enhance the cognitive skills in an individual. In an example implementation, a programmed processing unit is configured to execute processor-executable instructions to render a task with an interference at a user interface. As described in greater detail herein, one or more of the task and the interference can be time-varying and have a response deadline, such that the user interface imposes a limited time period for receiving at least one type of response from the individual interacting with the apparatus or system. An example processing unit is configured to control the user interface to render a first instance of a task with an interference at the user interface, requiring a first response from the individual to the first instance of the task in the presence of the interference and a response from the individual to at least one computer-implemented time-varying element. Either or both of the first instance of the task and the interference includes at least one a computer-implemented time-varying element. The user interface can be configured to measure data indicative of the response of the individual to the at least one computer-implemented time-varying element, the data including at least one measure of cognitive capabilities of the individual. The example processing unit is configured to measure substantially simultaneously the first response from the individual to the first instance of the task and the response from the individual to the at least one computer-implemented time-varying element, and to receive data indicative of the first response and the response of the individual to the at least one computer-implemented time-varying element. The example processing unit is also configured to analyze the data indicative of the first response and the response of the individual to the at least one computer-implemented time-varying element to compute a first performance metric comprising at least one quantified indicator of cognitive abilities of the individual. The programmed processing unit is further configured to adjust a difficulty of one or more of the task and the interference based on the computed at least one first performance metric such that the apparatus renders the task with the interference at a second difficulty level, and compute a second performance metric representative of cognitive abilities of the individual based at least in part on the data indicative of the first response and the response of the individual to the at least one computer-implemented time-varying element.

Another example system, method, and apparatus according to the principles herein can be configured to enhance the cognitive skills in an individual. In an example implementation, a programmed processing unit is configured to execute processor-executable instructions to render a task with an interference at a user interface. As described in greater detail herein, one or more of the task and the interference can be time-varying and have a response deadline, such that the user interface imposes a limited time period for receiving at least one type of response from the individual interacting with the apparatus or system. An example processing unit is configured to control the user interface to render a first instance of a task with an interference at the user interface, requiring a first response from the individual to the first instance of the task in the presence of the interference and a response from the individual to at least one computer-implemented time-varying element. Either or both of the first instance of the task and the interference includes at least one a computer-implemented time-varying element. The user interface can be configured to measure data indicative of the response of the individual to the at least one computer-implemented time-varying element, the data including at least one measure of cognitive capabilities of the individual. The example processing unit is configured to measure substantially simultaneously the first response from the individual to the first instance of the task and the response from the individual to the at least one computer-implemented time-varying element, and to receive data indicative of the first response and the response of the individual to the at least one computer-implemented time-varying element. The example processing unit is also configured to analyze the data indicative of the first response and the response of the individual to the at least one computer-implemented time-varying element to compute at least one performance metric comprising at least one quantified indicator of cognitive abilities of the individual. Based at least in part on the at least one performance metric, the example processing unit is also configured to generate an output to the user interface indicative of at least one of: (i) a likelihood of the individual experiencing an adverse event in response to administration of the pharmaceutical agent, drug, or biologic, (ii) a recommended change in one or more of the amount, concentration, or dose titration of the pharmaceutical agent, drug, or biologic, (iii) a change in the individual's cognitive response capabilities, (iv) a recommended treatment regimen, or (v) a recommended or determined degree of effectiveness of at least one of a behavioral therapy, counseling, or physical exercise.

In a non-limiting example, the processing unit can be further configured to measure substantially simultaneously the first response from the individual to the first instance of the task, a secondary response of the individual to the interference, and the response to the at least one computer-implemented time-varying element.

In a non-limiting example, the processing unit can be further configured to output to the individual or transmits to a computing device the computed at least one performance metric.

In a non-limiting example, the processing unit can be further configured to render a second instance of the task at the user interface, requiring a second response from the individual to the second instance of the task, and analyze a difference between the data indicative of the first response and the second response to compute an interference cost as a measure of at least one additional indication of cognitive abilities of the individual.

In a non-limiting example, based on the results of the analysis of the performance metrics, a medical, healthcare, or other professional (with consent of the individual) can gain a better understanding of potential adverse events which may occur (or potentially are occurring) if the individual is administered a particular type of, amount, concentration, or dose titration of a pharmaceutical agent, drug, biologic, or other medication, including potentially affecting cognition.

In a non-limiting example, a searchable database is provided herein that includes data indicative of the results of the analysis of the performance metrics for particular individuals, along with known levels of efficacy of at least one types of pharmaceutical agent, drug, biologic, or other medication experiences by the individuals, and/or quantifiable information on one or more adverse events experienced by the individual with administration of the at least one types of pharmaceutical agent, drug, biologic, or other medication. The searchable database can be configured to provide metrics for use to determine whether a given individual is a candidate for benefiting from a particular type of pharmaceutical agent, drug, biologic, or other medication based on the performance metrics, response measures, response profiles, and/or decision boundary metric (such as but not limited to response criteria) obtained for the individual in interacting with the task and/or interference rendered at the computing device.

As a non-limiting example, performance metrics can assist with identifying whether the individual is a candidate for a particular type of drug (such as but not limited to a stimulant, e.g., methylphenidate or amphetamine) or whether it might be beneficial for the individual to have the drug administered in conjunction with a regiment of specified repeated interactions with the tasks and/or interference rendered to the computing device. Other non-limiting examples of a biologic, drug or other pharmaceutical agent applicable to any example described herein include methylphenidate (MPH), scopolamine, donepezil hydrochloride, rivastigmine tartrate, memantine HCl, solanezumab, aducanumab, and crenezumab.

In a non-limiting example, based on the results of the analysis of the performance metric, a medical, healthcare, or other professional (with consent of the individual) can gain a better understanding of potential adverse events which may occur (or potentially are occurring) if the individual is administered a different amount, concentration, or dose titration of a pharmaceutical agent, drug, biologic, or other medication, including potentially affecting cognition.

In a non-limiting example, a searchable database is provided herein that includes data indicative of the results of the analysis of the performance metrics for particular individuals, along with known levels of efficacy of at least one types of pharmaceutical agent, drug, biologic, or other medication experiences by the individuals, and/or quantifiable information on one or more adverse events experienced by the individual with administration of the at least one types of pharmaceutical agent, drug, biologic, or other medication. The searchable database can be configured to provide metrics for use to determine whether a given individual is a candidate for benefiting from a particular type of pharmaceutical agent, drug, biologic, or other medication based on the response measures, response profiles, and/or decision boundary metric (such as but not limited to response criteria) obtained for the individual in interacting with the task and/or interference rendered at the computing device. As a non-limiting example, based on data indicative of a user interaction with the tasks and/or interference (including the computer-implemented time-varying element) rendered at a user interface of a computing device, the performance metrics could provide information on the individual, based on the cognitive capabilities of the individual. This data can assist with identifying whether the individual is a candidate for a particular type of drug (such as but not limited to a stimulant, e.g., methylphenidate or amphetamine) or whether it might be beneficial for the individual to have the drug administered in conjunction with a regiment of specified repeated interactions with the tasks and/or interference rendered to the computing device. Other non-limiting examples of a biologic, drug or other pharmaceutical agent applicable to any example described herein include methylphenidate (MPH), scopolamine, donepezil hydrochloride, rivastigmine tartrate, memantine HCl, solanezumab, aducanumab, and crenezumab.

In an example, the change in the individual's cognitive response capabilities comprises an indication of a change in degree of impulsiveness or conservativeness of the individual's cognitive response strategy.

As a non-limiting example, given that impulsive behavior is attendant with ADHD, an example cognitive platform that is configured for delivering treatment (including of executive function) may promote less impulsive behavior in a regimen. This may target dopamine systems in the brain, increasing normal regulation, which may result in a transfer of benefits of the reduction of impulsive behavior to the everyday life of an individual.

Stimulants such as methylphenidate and amphetamine are also administered to individuals with ADHD, to increase levels of norepinephrine and dopamine in the brain. Their cognitive effects may be attributed to their actions at the prefrontal cortex, however, there may not be remediation of cognitive control deficits or other cognitive abilities. An example cognitive platform herein can be configured for delivering treatment (including of executive function) to remediate an individual's cognitive control deficit.

The use of the example systems, methods, and apparatus according to the principles described herein can be applicable to many different types of neuropsychological conditions, such as but not limited to dementia, Parkinson's disease, cerebral amyloid angiopathy, familial amyloid neuropathy, Huntington's disease, or other neurodegenerative condition, autism spectrum disorder (ASD), presence of the 16p11.2 duplication, and/or an executive function disorder, such as but not limited to attention deficit hyperactivity disorder (ADHD), sensory-processing disorder (SPD), mild cognitive impairment (MCI), Alzheimer's disease, multiple-sclerosis, schizophrenia, major depressive disorder (MDD), or anxiety.

In any example implementation, data and other information from an individual is collected, transmitted, and analyzed with their consent.

As a non-limiting example, the cognitive platform described in connection with any example system, method and apparatus herein, including a cognitive platform based on interference processing, can be based on or include the Project: EVO™ platform by Akili Interactive Labs, Inc., Boston, Mass.

Non-Limiting Example Tasks and Interference

Following is a summary of reported results showing the extensive physiological, behavioral, and cognitive measurements data and analysis of the regions of the brain, neural activity, and/or neural pathways mechanisms involved (e.g., activated or suppressed) as an individual interact with stimuli under differing cognitive or emotional load. The articles also described the differences that can be sensed and quantifiably measured based on the individual's performance at cognitive tasks versus stimuli with computer-implemented time-varying elements.

Based on physiological and other measurements, regions of the brain implicated in emotional processing, cognitive tasks, and tasks, are reported. For example, in the review article by Pourtois et al., 2013, "Brain mechanisms for emotional influences on perception and attention: What is magic and what is not," *Biological Psychology*, 92, 492-512, it is reported that the amygdala monitors the emotional value of stimuli, projects to several other areas of the brain, and sends feedback to sensory pathways (including striate and extrastriate visual cortex). It is also reported that, due to an individual's limited processing capacity, the individual cannot fully analyze simultaneous stimuli in parallel, and these stimuli compete for processing resources in order to gain access to higher cognitive stages and awareness of the individual. With an individual having to direct attention to the location or features of a given stimulus, neural activity in brain regions representing this stimulus increases, at the expense of other concurrent stimuli. Pourtois et al. indicates that this phenomenon has been extensively demonstrated by neuronal recordings as well as imaging methods (EEG, PET, fMRI), and attributed to a gain control. Pourtois et al. concludes that emotion signals may enhance processing efficiency and competitive strength of emotionally significant events through gain control mechanisms similar to those of other attentional systems, but mediated by distinct neural mechanisms in the amygdala and interconnected prefrontal areas, and indicate that alterations in these brain mechanisms might be associated with psychopathological conditions, such as anxiety or phobia. It is also reported that anxious or depressed patients can show maladaptive attentional biases towards negative information. Pourtois et al. also reports that imaging results from EEG and fMRI support a conclusion that the processing of emotional (such as fearful or threat-related) stimuli yields a gain control effect in the visual cortex and the emotional gain control effect can account for the more efficient processing of threat-related stimuli, in addition to or in parallel with any concurrent modulation by other task-dependent or exogenous stimulus-driven mechanisms of attention (see also Brosch et al., 2011, "Additive effects of emotional, endogenous, and exogenous attention: behavioral and electrophysiological evidence," *Neuropsychologia* 49, 1779-1787).

During selective visual attention tests, EEG measurements can provide useful results in the modulation of the gamma band. (See, e.g., Müller et al., (2000). "Modulation of induced gamma band activity in the human EEG by attention and visual information processing." International Journal of Psychophysiology 38.3: 283-299). There are also studies showing modification in the EEG alpha band signal during attentional shifts. (See, e.g., Sauseng et al. (2005) "A shift of visual spatial attention is selectively associated with human EEG alpha activity." European Journal of Neuroscience 22.11: 2917-2926.) The P300 event-related potential (ERP) also provides data cues about attention. For example, Näätänen et al., (1978) "Early selective-attention effect on evoked potential reinterpreted", Acta Psychologica, 42, 313-329, discloses studies of the auditory attention, which show that the evoked potential has an improved negative response when a subject is presented with infrequent stimuli as compared to frequent stimuli. Näätänen et al discloses that this negative component, called the mismatch negativity, occurs 100 to 200 ms after the stimuli, a time which is perfectly in the range of the pre-attentive attention phase.

As described hereinabove, emotional processing and cognitive processing each require interactions within and among specific brain networks. The degree to which a cognitive assessment, monitor, or treatment is successful can depend on the degree of user engagement, attention, and focus. Major depressive disorder and other similar or related disorders can be associated with changes to cognitive capabilities in multiple cognitive domains including attention (concentration), memory (learning), decision making (judgment), comprehension, judgment, reasoning, understanding, learning, and remembering. The cognitive changes associated with depression can contribute to some of the disabilities experienced by individuals with this disorder.

As described hereinabove, the individual's response to a stimulus can vary depending on the state of the individual, including based on the individual's cognitive condition, disease, or executive function disorder. Measurements of the individual's performance can provide insight into the individual's status relative to a cognitive condition, disease, or executive function disorder, including the likelihood of onset and/or stage of progression of the cognitive condition, disease, or executive function disorder.

The foregoing non-limiting examples of physiological measurement data, behavioral data, and other cognitive data, show that the responses of an individual to tasks can differ based on the type of stimuli. Furthermore, the foregoing examples indicate that the degree to which an individual is affected by a computer-implemented time-varying element, and the degree to which the performance of the individual at a task is affected in the presence of the computer-implemented time-varying element, is dependent on the degree to which the individual exhibits a form of emotional or affective bias. As described herein, the differences in the individual's performance may be quantifiably sensed and measured based on the performance of the individual at cognitive tasks versus stimuli with computer-implemented time-varying elements (e.g., emotional or affective elements). The reported physiological measurement data, behavioral data, and other cognitive data, also show that the cognitive or emotional load evoked by a stimulus can vary depending on the state of an individual, including based on the individual's cognitive condition, disease state, or presence or absence of executive function disorder. As described herein, measurements of the differences in the individual's performance at cognitive tasks versus stimuli with computer-implemented time-varying elements can provide quantifiable insight into the likelihood of onset and/or stage of progression of a cognitive condition, disease, and/or executive function disorder, in the individual, such as but not limited to, social anxiety, depression, bipolar disorder, major depressive disorder, post-traumatic stress disorder, schizophrenia, autism spectrum disorder, attention deficit hyperactivity disorder, dementia, Parkinson's disease, Huntington's disease, or other neurodegenerative condition, Alzheimer's disease, or multiple-sclerosis.

The effects of interference processing on the cognitive control abilities of individuals has been reported. See, e.g., A. Anguera, Nature 501, p. 97 (Sep. 5, 2013) (the "Nature article"). See, also, U.S. Publication No. 20140370479A1 (U.S. application Ser. No. 13/879,589), filed on Nov. 10, 2011, which is incorporated herein by reference. Some of those cognitive abilities include cognitive control abilities in the areas of attention (selectivity, sustainability, etc.), working memory (capacity and the quality of information maintenance in working memory) and goal management (ability to effectively parallel process two attention-demanding tasks or to switch tasks). As an example, children diagnosed with ADHD (attention deficit hyperactivity disorder) exhibit difficulties in sustaining attention. Attention selectivity was found to depend on neural processes involved in ignoring goal-irrelevant information and on processes that facilitate the focus on goal-relevant information. The publications report neural data showing that when two objects are simultaneously placed in view, focusing attention on one can pull visual processing resources away from the other. Studies were also reported showing that memory depended more on effectively ignoring distractions, and the ability to maintain information in mind is vulnerable to interference by both distraction and interruption. Interference by distraction can be, e.g., an interference that is a non-target, that distracts the individual's attention from the primary task, but that the instructions indicate the individual is not to respond to. Interference by interruption/interruptor can be, e.g., an interference that is a target or two or more targets, that also distracts the individual's attention from the primary task, but that the instructions indicate the individual is to respond to (e.g., for a single target) or choose between/among (e.g., a forced-choose situation where the individual decides between differing degrees of a feature).

There were also fMRI results reported showing that diminished memory recall in the presence of a distraction can be associated with a disruption of a neural network involving the prefrontal cortex, the visual cortex, and the hippocampus (involved in memory consolidation). Prefrontal cortex networks (which play a role in selective attention) can be vulnerable to disruption by distraction. The publications also report that goal management, which requires cognitive control in the areas of working memory or selective attention, can be impacted by a secondary goal that also demands cognitive control. The publications also reported data indicating beneficial effects of interference processing as an intervention with effects on an individual's cognitive abilities, including to diminish the detrimental effects of distractions and interruptions. The publications described cost measures that can be computed (including an interference cost) to quantify the individual's performance, including to assess single-tasking or multitasking performance.

An example cost measure disclosed in the publications is the percentage change in an individual's performance at a single-tasking task as compared to a multi-tasking task, such that greater cost (that is, a more negative percentage cost) indicates increased interference when an individual is engaged in single-tasking vs multi-tasking. The publications describe an interference cost determined as the difference between an individual's performance on a task in isolation versus a task with one or more interference applied, where the interference cost provide an assessment of the individual's susceptibility to interference.

The tangible benefits of computer-implemented interference processing are also reported. For example, the Nature paper states that multi-tasking performance assessed using computer-implemented interference processing was able to quantify a linear age-related decline in performance in adults from 20 to 79 years of age. The Nature paper also reports that older adults (60 to 85 years old) who interacted with an adaptive form of the computer-implemented interference processing exhibited reduced multitasking costs, with the gains persisting for six (6) months. The Nature paper also reported that age-related deficits in neural signatures of cognitive control, as measured with electroencephalography, were remediated by the multitasking training (using the computer-implemented interference processing), with enhanced midline frontal theta power and frontal-posterior theta coherence. Interacting with the computer-implemented interference processing resulted in performance benefits that extended to untrained cognitive control abilities (enhanced sustained attention and working memory), with an increase in midline frontal theta power predicting a boost in sustained attention and preservation of multitasking improvement six (6) months later.

The example systems, methods, and apparatus according to the principles herein are configured to classify an individual as to cognitive abilities and/or to enhance those cognitive abilities based on implementation of interference processing using a computerized cognitive platform. The example systems, methods, and apparatus are configured to implement a form of multi-tasking using the capabilities of a programmed computing device, where an individual is required to perform a task and an interference substantially simultaneously, where the task and/or the interference includes a computer-implemented time-varying element, and the individual is required to respond to the computer-implemented time-varying element. The sensing and measurement capabilities of the computing device are configured to collect data indicative of the physical actions taken by the individual during the response execution time to respond to the task at substantially the same time as the computing device collects the data indicative of the physical actions taken by the individual to respond to the computer-implemented time-varying element. The capabilities of the computing devices and programmed processing units to render the task and/or the interference in real time to a user interface, and to measure the data indicative of the individual's responses to the task and/or the interference and the computer-implemented time-varying element in real time and substantially simultaneously can provide quantifiable measures of an individual's cognitive capabilities, to rapidly switch to and from different tasks and interferences, or to perform multiple, different, tasks or interferences in a row (including for single-tasking, where the individual is required to perform a single type of task for a set period of time).

In any example herein, the task and/or interference includes a response deadline, such that the user interface imposes a limited time period for receiving at least one type of response from the individual interacting with the apparatus or computing device. For example, the period of time that an individual is required to interact with a computing device or other apparatus to perform a task and/or an interference can be a predetermined amount of time, such as but not limited to about 30 seconds, about 1 minute, about 4 minutes, about 7 minutes, about 10 minutes, or greater than 10 minutes.

The example systems, methods, and apparatus can be configured to implement a form of multi-tasking to provide measures of the individual's capabilities in deciding whether to perform one action instead of another and to activate the rules of the current task in the presence of an interference such that the interference diverts the individual's attention from the task, as a measure of an individual's cognitive abilities in executive function control.

The example systems, methods, and apparatus can be configured to implement a form of single-tasking, where measures of the individual's performance at interacting with a single type of task (i.e., with no interference) for a set period of time (such as but not limited to navigation task only or a target discriminating task only) can also be used to provide measure of an individual's cognitive abilities.

The example systems, methods, and apparatus can be configured to implement sessions that involve differing sequences and combinations of single-tasking and multi-tasking trials. In a first example implementation, a session can include a first single-tasking trial (with a first type of task), a second single-tasking trial (with a second type of task), and a multi-tasking trial (a primary task rendered with an interference). In a second example implementation, a session can include two or more multi-tasking trials (a primary task rendered with an interference). In a third example implementation, a session can include two or more single-tasking trials (all based on the same type of tasks or at least one being based on a different type of task).

The performance can be further analyzed to compare the effects of two different types of interference (e.g. distraction or interruptor) on the performances of the various tasks. Some comparisons can include performance without interference, performance with distraction, and performance with interruption. The cost of each type of interference (e.g. distraction cost and interruptor/multi-tasking cost) on the performance level of a task is analyzed and reported to the individual.

The interference processing provides a quantifiable way to measure and improve the ability to process interference events (interruptions and distractions). Interference susceptibility is recognized as a limiting factor across global executive function (including attention and memory) and is known to be fragile in multiple diseases. Changes in EEG signals are shown to occurred at neurological loci associated with cognitive control. For example, midline frontal theta (MFT) power as measured by stimulus-locked electroencephalography (EEG) before, during, or after an individual performs the interference processing can provide indications of attention and interference susceptibility.

In any example herein, the interference can a secondary task that includes a stimulus that is either a non-target (as a distraction) or a target (as an interruptor), or a stimulus that is differing types of targets (e.g., differing degrees of a facial expression or other characteristic/feature difference).

Based on the capability of a programmed processing unit to control the effecting of multiple separate sources (including sensors and other measurement components) and the receiving of data selectively from these multiple different sources at substantially simultaneously (i.e., at roughly the same time or within a short time interval) and in real-time, the example systems, methods, and apparatus herein can be used to collect quantitative measures of the responses form an individual to the task and/or interference, which could not be achieved using normal human capabilities. As a result, the example systems, methods, and apparatus herein can be configured to implement a programmed processing unit to render the interference substantially simultaneously with the task over certain time periods.

In some example implementations, the example systems, methods, and apparatus herein also can be configured to receive the data indicative of the measure of the degree and type of the individual's response to the task substantially simultaneously as the data indicative of the measure of the degree and type of the individual's response to the interference is collected (whether the interference includes a target or a non-target). In some examples, the example systems, methods, and apparatus are configured to perform the analysis by applying scoring or weighting factors to the measured data indicative of the individual's response to a non-target that differ from the scoring or weighting factors applied to the measured data indicative of the individual's response to a target, in order to compute a cost measure (including an interference cost).

In an example systems, methods, and apparatus herein, the cost measure can be computed based on the difference in measures of the performance of the individual at one or more tasks in the absence of interference as compared to the measures of the performance of the individual at the one or more tasks in the presence of interference, where the one or more tasks and/or the interference includes one or more computer-implemented time-varying elements. As described herein, the requirement of the individual to interact with (and provide a response to) the computer-implemented time-varying element(s) can introduce cognitive or emotional load that quantifiably affects the individual's capability at performing the task(s) and/or interference due to the requirement for emotional processing to respond to the computer-implemented time-varying element. In an example, the interference cost computed based on the data collected herein can provide a quantifiable assessment of the individual's susceptibility to interference. The determination the difference between an individual's performance on a task in isolation versus a task in the presence of one or more interference (the task and/or interference including the computer-implemented time-varying element) provides an interference cost metric that can be used to assess and classify cognitive capabilities of the individual. The interference cost computed based on the individuals performance of tasks and/or interference performed can also provide a quantifiable measure of the individual's cognitive condition, disease state, or presence or stage of an executive function disorder, such as but not limited to, social anxiety, depression, bipolar disorder, major depressive disorder, post-traumatic stress disorder, schizophrenia, autism spectrum disorder, attention deficit hyperactivity disorder, dementia, Parkinson's disease, Huntington's disease, or other neurodegenerative condition, Alzheimer's disease, or multiple-sclerosis.

The example systems, methods, and apparatus herein can be configured to perform the analysis of the individual's susceptibility to interference (including as a cost measure such as the interference cost), as a reiterating, cyclical process. For example, where an individual is determined to have minimized interference cost for a given task and/or interference, the example systems, methods, and apparatus can be configured to require the individual to perform a more challenging task and/or interference (i.e., having a higher difficulty level) until the individual's performance metric indicates a minimized interference cost in that given condition, at which point example systems, methods, and apparatus can be configured to present the individual with an even more challenging task and/or interference until the individual's performance metric once again indicates a minimized interference cost for that condition. This can be repeated any number of times until a desired end-point of the individual's performance is obtained.

As a non-limiting example, the interference cost can be computed based on measurements of the individual's performance at a single-tasking task (without an interference) as compared to a multi-tasking task (with interference), to provide an assessment. For example, an individual's performance at a multi-tasking task (e.g., targeting task with interference) can be compared to their performance at a single-tasking targeting task without interference to provide the interference cost.

Example systems, apparatus and methods herein are configured to analyze data indicative of the degree to which an individual is affected by a computer-implemented time-varying element, and/or the degree to which the performance of the individual at a task is affected in the presence of the computer-implemented time-varying element, to provide performance metric including a quantified indicator of cognitive abilities of the individual. The performance metric can be used as an indicator of the degree to which the individual exhibits a form of emotional or affective bias.

In some example implementations, the example systems, methods, and apparatus herein also can be configured to selectively receive data indicative of the measure of the degree and type of the individual's response to an interference that includes a target stimulus (i.e., an interruptor) substantially simultaneously (i.e., at substantially the same time) as the data indicative of the measure of the degree and type of the individual's response to the task is collected and to selectively not collect the measure of the degree and type of the individual's response to an interference that includes a non-target stimulus (i.e., a distraction) substantially simultaneously (i.e., at substantially the same time) as the data indicative of the measure of the degree and type of the individual's response to the task is collected. That is, the example systems, methods, and apparatus are configured to discriminate between the windows of response of the individual to the target versus non-target by selectively controlling the state of the sensing/measurement components for measuring the response either temporally and/or spatially. This can be achieved by selectively activating or de-activating sensing/measurement components based on the presentation of a target or non-target, or by receiving the data measured for the individual's response to a target and selectively not receiving (e.g., disregarding, denying, or rejecting) the data measured for the individual's response to a non-target.

As described herein, using the example systems, methods, and apparatus herein can be implemented to provide a measure of the cognitive abilities of an individual in the area of attention, including based on capabilities for sustainability of attention over time, selectivity of attention, and reduction of attention deficit. Other areas of an individual's cognitive abilities that can be measured using the example systems, methods, and apparatus herein include affective bias, mood, level of cognitive bias, impulsivity, inhibition, perceptive abilities, reaction and other motor functions, visual acuity, long-term memory, working memory, short-term memory, logic, and decision-making.

As described herein, using the example systems, methods, and apparatus herein can be implemented to adapt the tasks and/or interference (at least one including a computer-implemented time-varying element) from one user session to another (or even from one user trial to another) to enhance the cognitive skills of an individual based on the science of brain plasticity. Adaptivity is a beneficial design element for any effective plasticity-harnessing tool. In example systems, methods, and apparatus, the processing unit is configured to control parameters of the tasks and/or interference, such as but not limited to the timing, positioning, and nature of the stimuli, so that the physical actions of the individual can be recorded during the interaction(s). As described hereinabove, the individual's physical actions are affected by their neural activity during the interactions with the computing device to perform single-tasking and multi-tasking tasks. The science of interference processing shows (based on the results from physiological and behavioral measurements) that the aspect of adaptivity can result in changes in the brain of an individual in response to the training from multiple sessions (or trials) based on neuroplasticity, thereby enhancing the cognitive skills of the individual. The example systems, methods, and apparatus are configured to implement tasks and/or interference with at least one computer-implemented time-varying element, where the individual performs the interference processing. As supported in the published research results described hereinabove, the effect on an individual of performing tasks can tap into novel aspects of cognitive training to enhance the cognitive abilities of the individual.

FIGS. 7A-10D show non-limiting example user interfaces that can be rendered using example systems, methods, and apparatus herein to render the tasks and/or interferences (either or both with computer-implemented time-varying element) for user interactions. The non-limiting example user interfaces of FIGS. 7A-10D also can be used for one or more of: to display instructions to the individual for performing the tasks and/or interferences, interact with the computer-implemented time-varying element, to collect the data indicative of the individual's responses to the tasks and/or the interferences and the computer-implemented time-varying element, to show progress metrics, and to provide analysis metrics.

FIGS. 7A-7D show non-limiting example user interfaces rendered using example systems, methods, and apparatus herein. As shown in FIGS. 7A-7B, an example programmed processing unit can be used to render to the user interfaces (including graphical user interfaces) display features 700 for displaying instructions to the individual for performing the tasks and/or interferences and to interact with the computer-implemented time-varying element, and metric features 702 to show status indicators from progress metrics and/or results from application of analytics to the data collected from the individual's interactions (including the responses to tasks/interferences) to provide the analysis metrics. In any example systems, methods, and apparatus herein, the predictive model can be used to provide the analysis metrics provided as a response output. In any example systems, methods, and apparatus herein, the data collected from the user interactions can be used as input to train the predictive model. As shown in FIGS. 7A-7B, an example programmed processing unit also may be used to render to the user interfaces (including graphical user interfaces) an avatar or other processor-rendered guide 704 that an individual is required to control (such as but not limited to navigate a path or other environment in a visuo-motor task, and/or to select an object in a target discrimination task). In an example, the computer-implemented time-varying element may be includes as a component of the visuo-motor task (e.g., as a milestone object along the math) or as a component of the target discrimination task, e.g., where a specific type of computer-implemented time-varying element is the target, and other types of the computer-implemented time-varying element are not. As shown in FIG. 7B, the display features 700 can be used to instruct the individual what is expected to perform a navigation task while the user interface depicts (using the dashed line) the type of movement of the avatar or other processor-rendered guide 704 required for performing the navigation task. In an example, the navigation task may include milestone objects (possibly including computer-implemented time-varying elements) that the individual is required to steer an avatar to cross or avoid, in order to determine the scoring. As shown in FIG. 7C, the display features 700 can be used to instruct the individual what is expected to perform a target discrimination task while the user interface depicts the type of object(s) 706 and 708 that may be rendered to the user interface, with one type of object 706 (possibly including a target computer-implemented time-varying element) designated as a target while the other type of object 708 that may be rendered to the user interface is designated as a non-target (possibly including a non-target computer-implemented time-varying element), e.g., by being crossed out in this example. As shown in FIG. 7D, the display features 700 can be used to instruct the individual what is expected to perform both a navigation task as a primary task and a target discrimination as a secondary task (i.e., an interference) while the user interface depicts (using the dashed line) the type of movement of the avatar or other processor-rendered guide 704 required for performing the navigation task, and the user interface renders the object type designated as a target object 706 and the object type designated as a non-target object 708.

FIGS. 8A-8D show examples of the features of object(s) (targets or non-targets) that can be rendered as time-varying characteristics to an example user interface, according to the principles herein. FIG. 8A shows an example where the modification to the time-varying characteristics of an aspect of the object 800 rendered to the user interface is a dynamic change in position and/or speed of the object 800 relative to environment rendered in the graphical user interface. FIG. 8B shows an example where the modification to the time-varying characteristics of an aspect of the object 802 rendered to the user interface is a dynamic change in size and/or direction of trajectory/motion, and/or orientation of the object 802 relative to the environment rendered in the graphical user interface. FIG. 8C shows an example where the modification to the time-varying characteristics of an aspect of the object 804 rendered to the user interface is a dynamic change in shape or other type of the object 804 relative to the environment rendered in the graphical user interface. In this non-limiting example, the time-varying characteristic of object 804 is effected using morphing from a first type of object (a star object) to a second type of object (a round object). In another non-limiting example, the time-varying characteristic of object 804 is effected by rendering a blendshape as a proportionate combination of a first type of object and a second type of object. FIG. 8C shows an example where the modification to the time-varying characteristics of an aspect of the object 804 rendered to the user interface is a dynamic change in shape or other type of the object 804 rendered in the graphical user interface (in this non-limiting example, from a star object to a round object). FIG. 8D shows an example where the modification to the time-varying characteristics of an aspect of the object 806 rendered to the user interface is a dynamic change in pattern, or color, or visual feature of the object 806 relative to environment rendered in the graphical user interface (in this non-limiting example, from a star object having a first pattern to a star object having a second pattern). In another non-limiting example, the time-varying characteristic of object can be a rate of change of a facial expression depicted on or relative to the object. In any example herein, the foregoing time-varying characteristic can be applied to an object including the computer-implemented time-varying element to modify a cognitive or emotional load of the individual's interaction with the apparatus (e.g., computing device or cognitive platform).

Figure 9A:
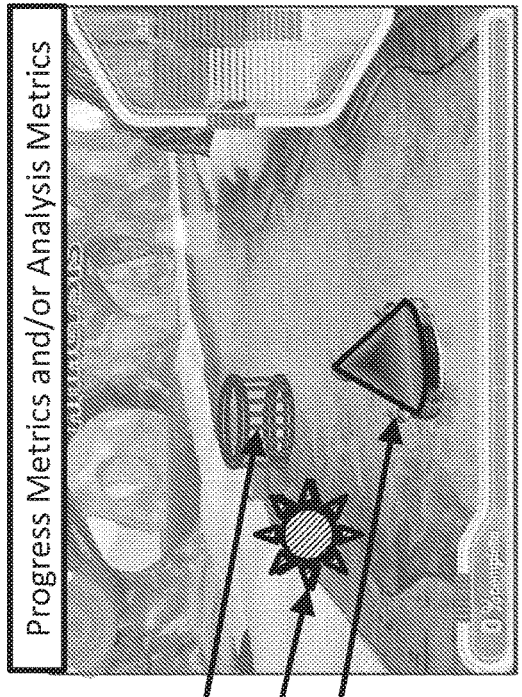
FIGS. 9A-9T show examples of the dynamics of tasks and interferences that can be rendered at user interfaces, according to the principles herein.
Figure 9B:
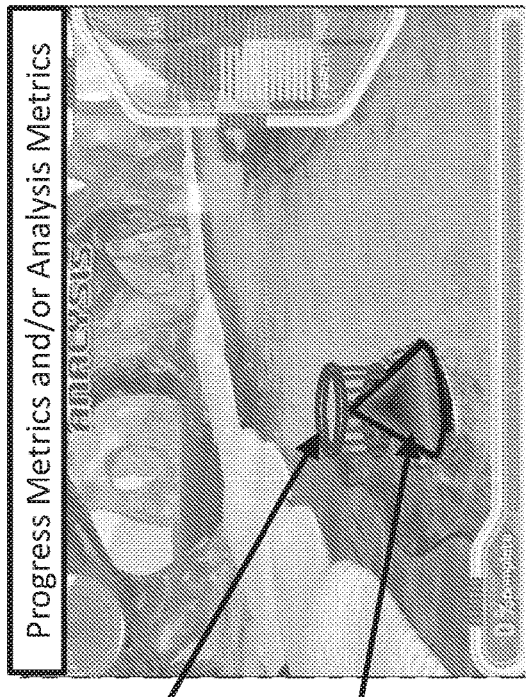
Figure 9C:
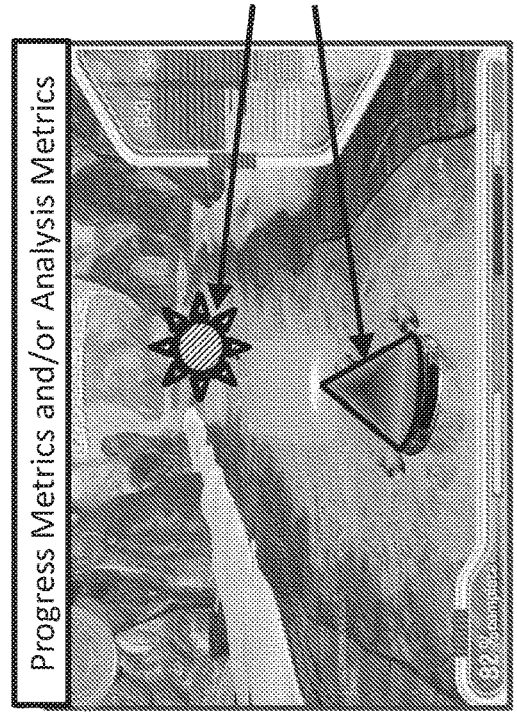
Figure 9D:
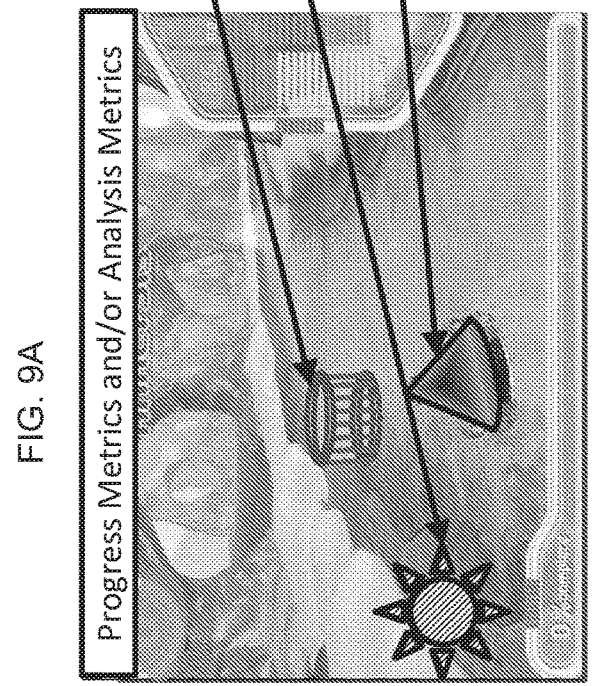
Figure 9I:
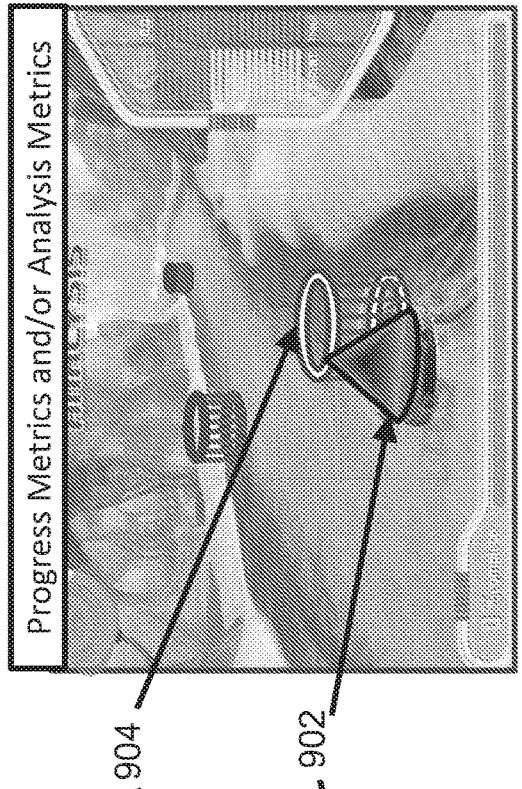
Figure 9K:
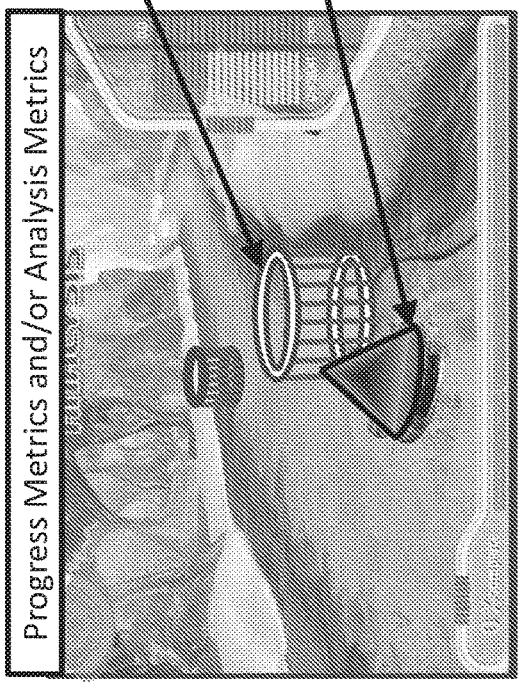
Figure 9J:
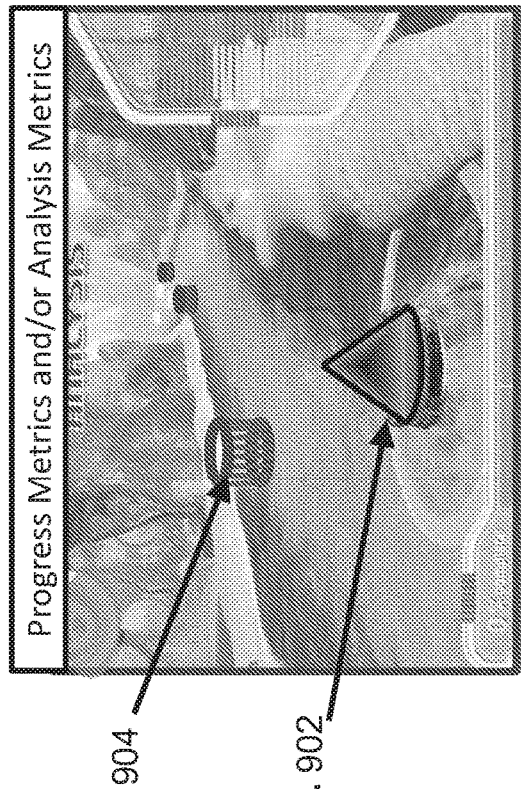
Figure 9L:
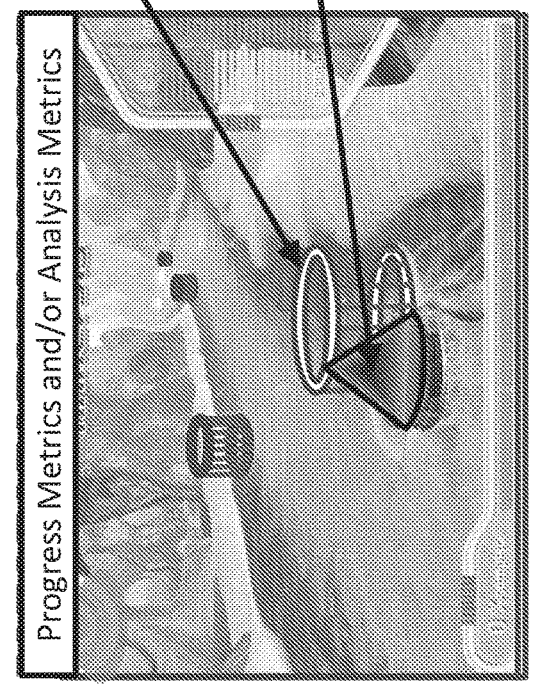
Figure 9M:
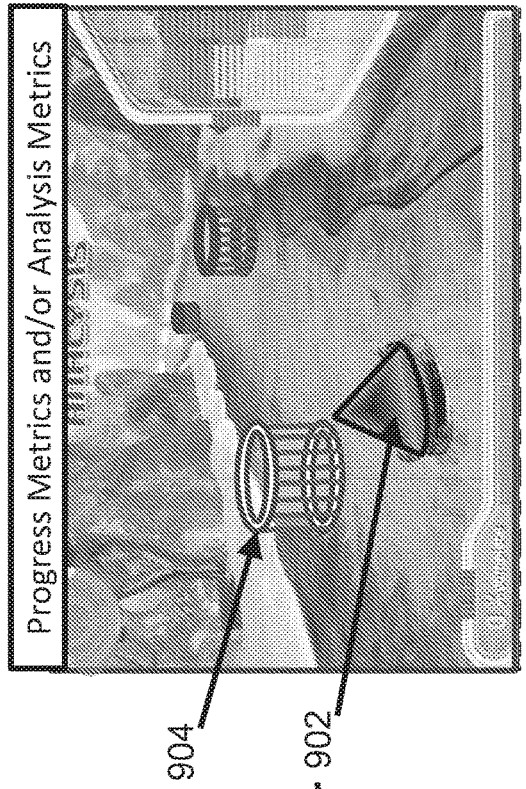
Figure 9O:
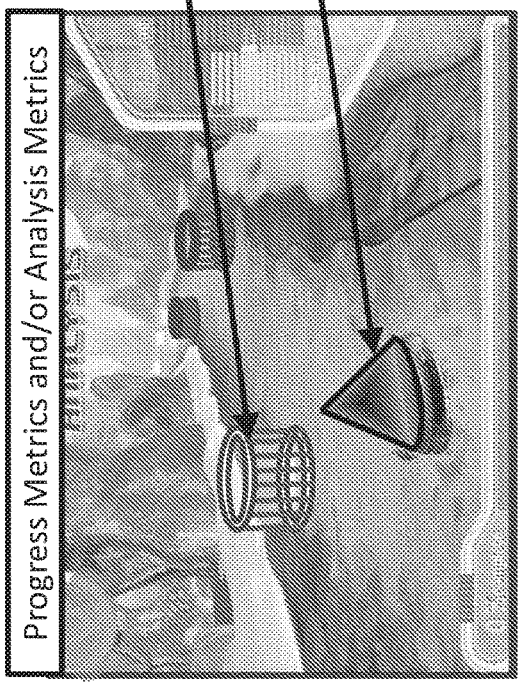
Figure 9N:
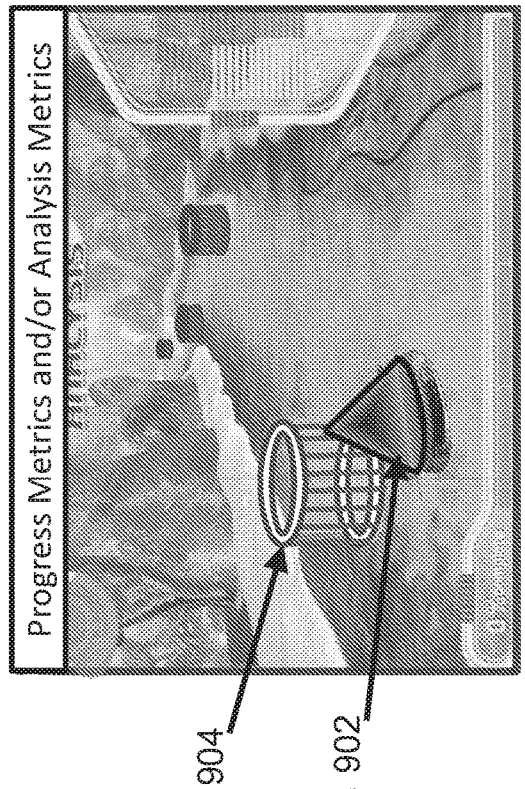
Figure 9P:
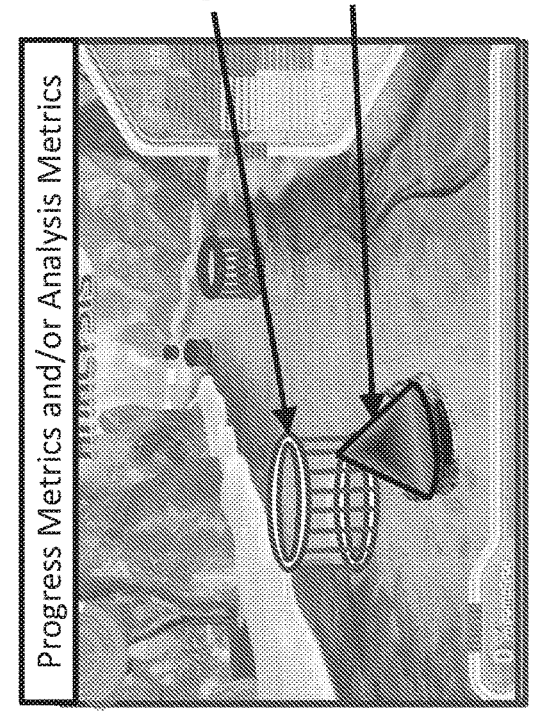
Figure 9Q:
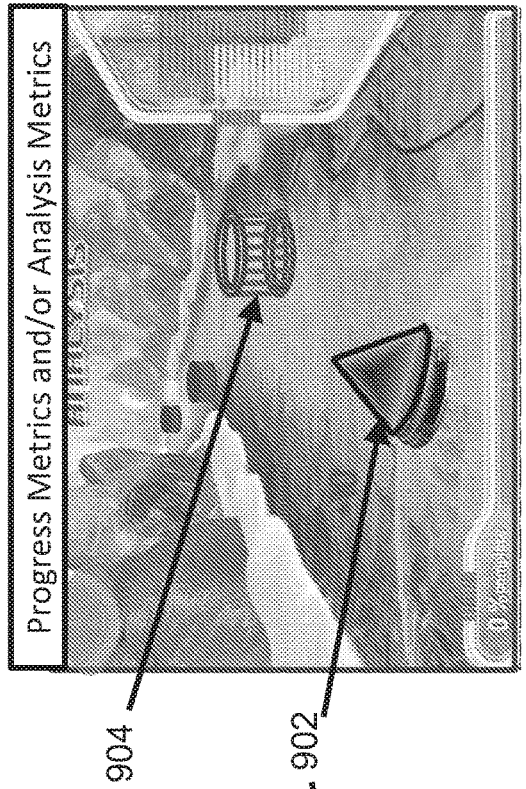
Figure 9R:
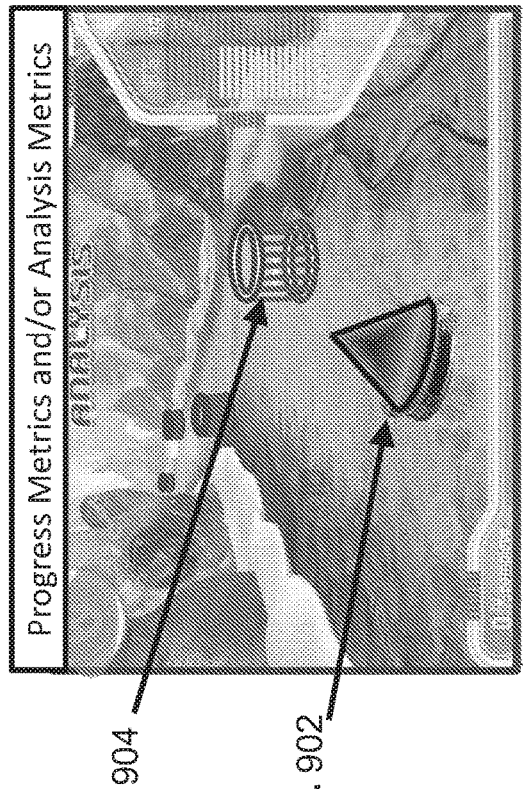
Figure 9S:
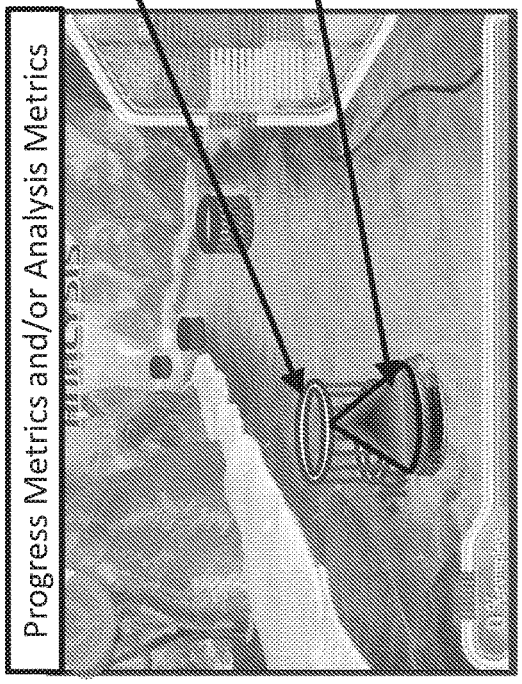
Figure 9T:
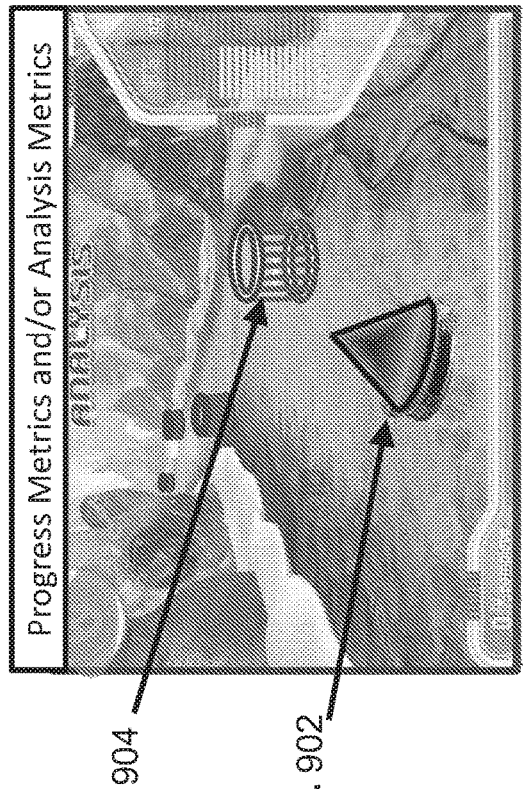

FIGS. 9A-9T show a non-limiting example of the dynamics of tasks and interferences that can be rendered at user interfaces, according to the principles herein. In this example, the task is a visuo-motor navigation task, and the interference is target discrimination (as a secondary task). As shown in FIGS. 9D, 9I-9K, and 9O-9Q, the individual is required to perform the navigation task by controlling the motion of the avatar 902 along a path that coincides with the milestone objects 904. FIGS. 9A-9T show a non-limiting example implementation where the individual is expected to actuate an apparatus or computing device (or other sensing device) to cause the avatar 902 to coincide with the milestone object 904 as the response in the navigation task, with scoring based on the success of the individual at crossing paths with (e.g., hitting) the milestone objects 904. In another example, the individual is expected to actuate an apparatus or computing device (or other sensing device) to cause the avatar 902 to miss the milestone object 904, with scoring based on the success of the individual at avoiding the milestone objects 904. FIGS. 9A-9C show the dynamics of a target object 906 (a star having a first type of pattern), where the time-varying characteristic is the trajectory of motion of the target object. FIGS. 9E-9H show the dynamics of a non-target object 908 (a star having a second type of pattern), where the time-varying characteristic is the trajectory of motion of the object. FIGS. 9I-9T show the dynamics of other portions of the navigation task, where the individual is expected to guide the avatar 902 to cross paths with the milestone object 904 in the absence of an interference (a secondary task).

In the example of FIGS. 9A-9T, the processing unit of the example system, method, and apparatus is configured to receive data indicative of the individual's physical actions to cause the avatar 902 to navigate the path. For example, the individual may be required to perform physical actions to "steer" the avatar, e.g., by changing the rotational orientation or otherwise moving a computing device. Such action can cause a gyroscope or accelerometer or other motion or position sensor device to detect the movement, thereby providing measurement data indicative of the individual's degree of success in performing the navigation task.

In the example of FIGS. 9A-9C and 9E-9H, the processing unit of the example system, method, and apparatus is configured to receive data indicative of the individual's physical actions to perform the target discrimination task. For example, the individual may be instructed prior to a trial or other session to tap, or make other physical indication, in response to display of a target object 906, and not to tap to make the physical indication in response to display of a non-target object 908. In FIGS. 9A-9C and 9E-9H, the target discrimination task acts as an interference (i.e., a secondary task) to the primary navigation task, in an interference processing multi-tasking implementation. As described hereinabove, the example systems, methods, and apparatus can cause the processing unit to render a display feature to display the instructions to the individual as to the expected performance. As also described hereinabove, the processing unit of the example system, method, and apparatus can be configured to (i) receive the data indicative of the measure of the degree and type of the individual's response to the primary task substantially simultaneously as the data indicative of the measure of the degree and type of the individual's response to the interference is collected (whether the interference includes a target or a non-target), or (ii) to selectively receive data indicative of the measure of the degree and type of the individual's response to an interference that includes a target stimulus (i.e., an interruptor) substantially simultaneously (i.e., at substantially the same time) as the data indicative of the measure of the degree and type of the individual's response to the task is collected and to selectively not collect the measure of the degree and type of the individual's response to an interference that includes a non-target stimulus (i.e., a distraction) substantially simultaneously (i.e., at substantially the same time) as the data indicative of the measure of the degree and type of the individual's response to the task is collected FIGS. 10A-10D show another non-limiting example of the dynamics of tasks and interferences that can be rendered at user interfaces, according to the principles herein. In this example, the task is a visuo-motor navigation task, and the interference is target discrimination (as a secondary task), where an individual is required to perform physical actions to cause an avatar 1002 to navigate to cross paths with the milestone object 1004 as the primary task and interact with an object 1006 as target discrimination (interference as a secondary task). FIGS. 10A-10D show an example of the type of reward 1008 that can be shown on the graphical user interface responsive to the individual's indication of selecting a target object. In this non-limiting example, the reward 1008 is a set of rings that are rendered near the target 1006 at substantially the time the individual makes the second response selecting the target. In a non-limiting example, the second response is made by a tap, or other physical action to a portion of the user interface based on the individual's decision to enter a response.

In various examples, the degree of non-linearity of the accumulation of belief for an individual's decision making (i.e., as to whether to execute a response) can be modulated based on adjusting the time-varying characteristics of the task and/or interference. As a non-limiting example, where the time-varying characteristic is a trajectory, speed, orientation, type and/or size of the object (target or non-target), the amount of information available to an individual to develop a belief (in order to make decision as to whether to execute a response) can be made smaller initially, e.g., where the object caused to be more difficult to discriminate by being rendered as farther away or smaller, and can be made to increase at differing rates (nonlinearly) depending on how quickly more information is made available to the individual to develop belief (e.g., as the object is rendered to appear to get larger, change orientation, move slower, or move closer in the environment). Other non-limiting example time-varying characteristics of the task and/or interference that can be adjusted to modulate the degree of non-linearity of the accumulation of belief include one or more of a rate of change of a facial expression, at least one color of an object, the type of the object (including whether there is one or two or more differing types of target objects), a rate of morphing of a first type of object to change to a second type of object, and a blendshape of computer-implemented time-varying elements.

The data indicative of the individual's response to the task and the response of the individual to the at least one computer-implemented time-varying element is used to compute at least one performance metric comprising at least one quantified indicator of cognitive abilities of the individual. In a non-limiting example, the performance metric can include the computed interference cost.

The difficulty levels (including the difficulty of the task and/or interference, and of the computer-implemented time-varying element) of a subsequent session can be set based on the performance metric computed for the individual's performance from a previous session, and can be optimized to modify an individual's performance metric (e.g., to lower or optimize the interference cost).

In a non-limiting example, the adaptation of the difficulty of a task and/or interference may be adapted with each different stimulus that is presented as a computer-implemented time-varying element.

In another non-limiting example, the example system, method, and apparatus herein can be configured to adapt a difficulty level of a task and/or interference (including the computer-implemented time-varying element) one or more times in fixed time intervals or in other set schedule, such as but not limited to each second, in 10 second intervals, every 30 seconds, or on frequencies of once per second, 2 times per second, or more (such as but not limited to 30 times per second).

In an example, the difficulty level of a task or interference can be adapted by changing the time-varying characteristics, such as but not limited to a speed of an object, a rate of change of a facial expression, a direction of trajectory of an object, a change of orientation of an object, at least one color of an object, a type of an object, or a size of an object, or changing a sequence or balance of presentation of a target stimulus versus a non-target stimulus.

In a non-limiting example of a visuo-motor task (a type of navigation task), one or more of navigation speed, shape of the course (changing frequency of turns, changing turning radius), and number and/or size of obstacles can be changed to modify the difficulty of a navigation game level, with the difficulty level increasing with increasing speed and/or increasing numbers and/or sizes of obstacles (including types of milestone objects (e.g., some milestone objects to avoid or some milestone objects to cross/coincide with)).

In a non-limiting example, the difficulty level of a task and/or interference of a subsequent level can also be changed in real-time as feedback, e.g., the difficulty of a subsequent level can be increased or decreased in relation to the data indicative of the performance of the task.

In a non-limiting example implementation, measurements are made using a cognitive platform that is configured for coupling with a lower-cost EEG, such as but not limited to a NeuroSky® EEG biosensor (NeuroSky, Inc., San Jose, Calif.). Measurements are performed using the EEG, to collect EEG nData, while a user is interacting with the cognitive platform in a diagnostic mode. The storage and graphing of the nData is performed. Analysis of the data indicates that there appears to be measurable differences in the trend of the EEG biosensor measurements during the various sessions of user interaction with the cognitive platform. The example EEG can be used to measures the EEG power spectrums, including alpha waves and beta waves, and provide measurement data, such as but not limited to alpha waves, beta waves, measures of attention and meditation, and/or eye blinks. The example EEG device includes a headset and a sensor mount, where a coupling component including a reference electrode and a ground electrode is mounted to, e.g., the ear of the individual, and coupled to the headset, and an EEG electrode is coupled to the sensor mount (coupled to the individual, e.g., on the forehead above the eye (FP1 position)). The example lower-cost EEG can be used to measure alpha waves, beta waves, and gamma waves.

The physiological measurements are made of the individual using the EEG device as the individual engages in the physical actions to perform the tasks and/or interference. In the non-limiting example implementation, the cognitive platform renders a primary task and a primary task with an interference in differing modes. The example first mode (mode 1) involves a primary navigation task with an interference of a target discrimination (as a secondary task) in a first multi-tasking task. The example second mode (mode 2) involves a target discrimination task only (single-tasking). The example third mode (mode 3) involves a navigation task only (single-tasking). The example fourth mode (mode 4) involves a primary navigation task with an interference of a target discrimination (as a secondary task) in a second multi-tasking task.

Figure 11A:
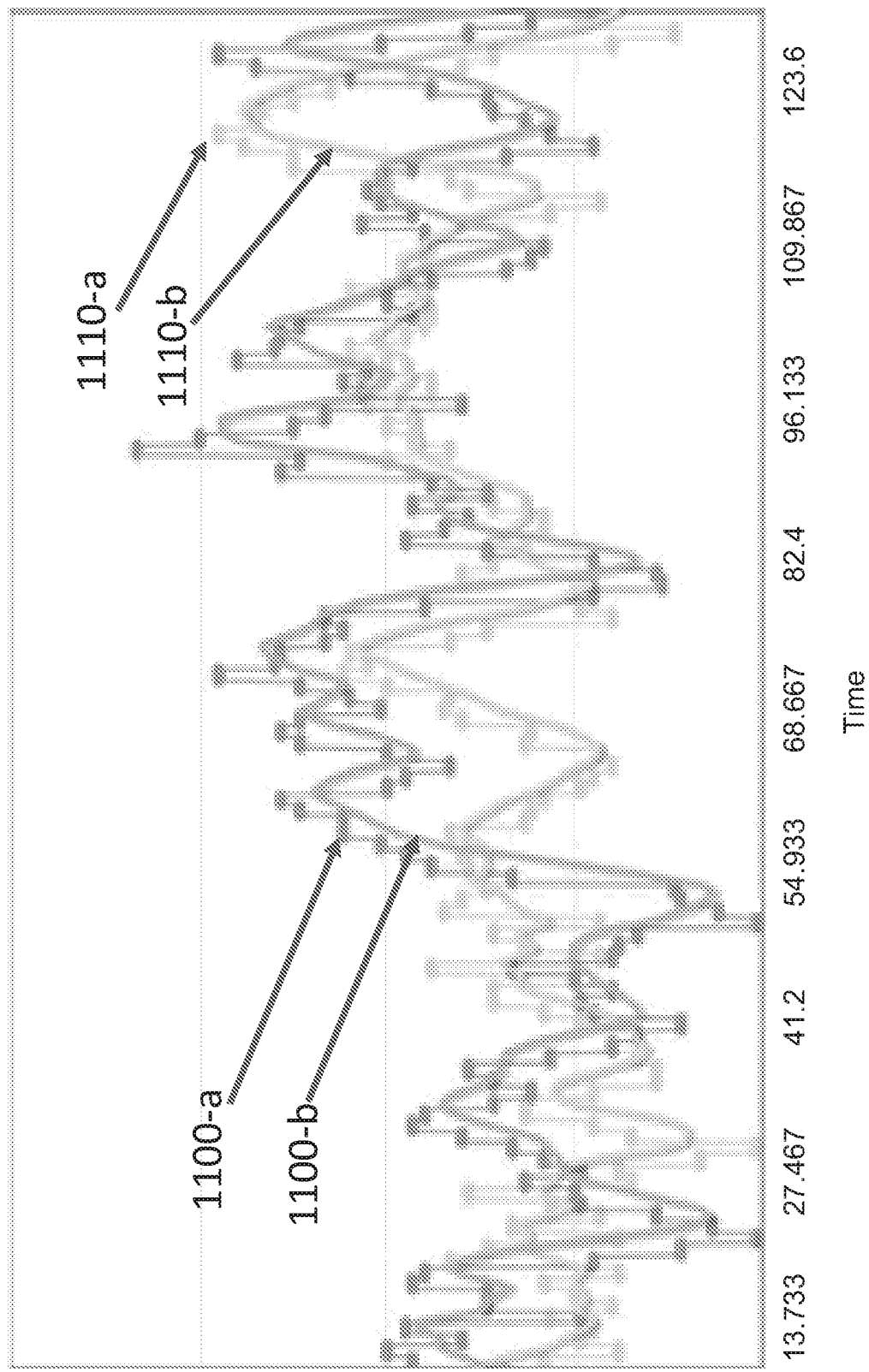
FIGS. 11A-11B show example plots of physiological measurements made using an electroencephalogram (EEG), according to the principles herein.

FIG. 11A shows an example plot of EEG signal data versus time from measurements collected using a lower-cost EEG biosensor that is mounted to a portion of a head of an individual who is interacting with the example cognitive platform to perform the multi-tasking task. Curves 1100-a and 1100-b are data indicative of the individual's focus. Curves 1110-a and 1110-b are data indicative of the individual's meditative state (calmness). The solid line curve 1100-b is a running average of the data points that form curve 1100-a. The solid line curve 1110-b is a running average of, and therefore slightly displaced relative to, the data points that form curve 1110-a. In this example, the individual is performing computer-implemented multi-tasking tasks in sessions involving targeting task (interference) and navigation task (primary task), that require responses from the individual. In an example, the user response recorded for the targeting or navigation task can be, but is not limited to, a touch, swipe or other gesture relative to a user interface or image collection device (including a touch-screen or other pressure sensitive screen, or a camera) to interact with a user interface. In another example, the user response recorded for the targeting or navigation task can be, but is not limited to, user actions that cause changes in a position, orientation, or movement of a computing device including the cognitive platform, that is recorded using a sensor disposed in or otherwise coupled to the computing device (such as but not limited to a motion sensor or position sensor).

Figure 11B:
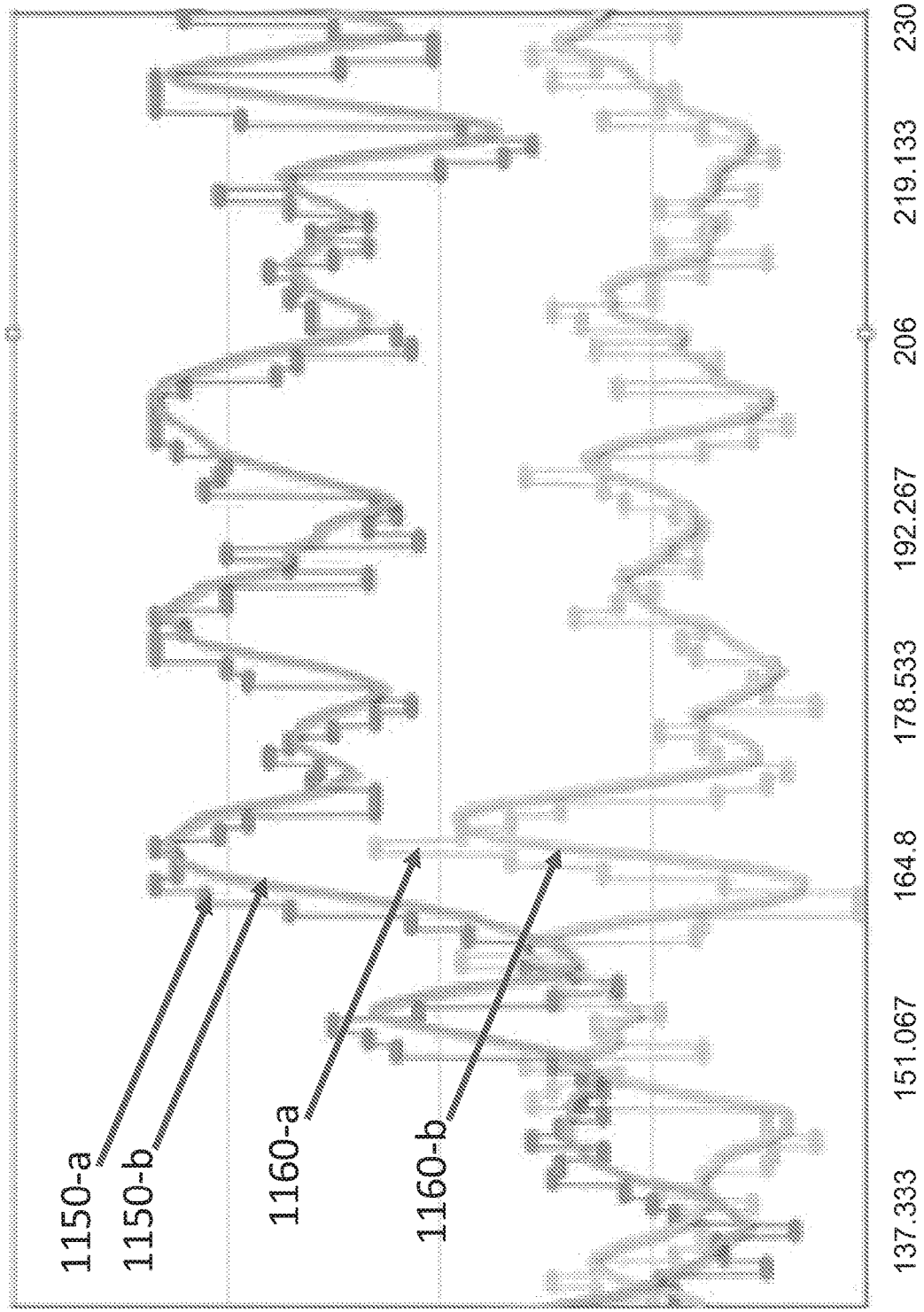

FIG. 11B shows an example plot of EEG signal data versus time from measurements collected using the lower-cost EEG biosensor as the individual is interacting with an example apparatus according to the principles herein to perform computer-implemented single-tasking tasks (including performing physical actions to provide responses to a primary in the absence of an interference) in sessions involving solely targeting, that require responses from the individual. Curves 1150-*a* and 1150-*b* are data indicative of the individual's focus. Curves 1160-*a* and 1160-*b* are data indicative of the individual's meditative state (calmness). The solid line curve 1150-*b* is a running average of the data points that form curve 1150-*a*. The solid line curve 1160-*b* is a running average of, and therefore slightly displaced relative to, the data points that form curve 1160-*a*.

In an example, the response recorded for the targeting task can be, but is not limited to, a touch, swipe or other gesture relative to a user interface or image collection device (including a touch-screen or other pressure sensitive screen, or a camera) to interact with a user interface. In another example, the response recorded for the targeting task can be, but is not limited to, user actions that cause changes in a position, orientation, or movement of a computing device including the cognitive platform, that is recorded using a sensor disposed in or otherwise coupled to the computing device (such as but not limited to a motion sensor or position sensor).

Figure 12:
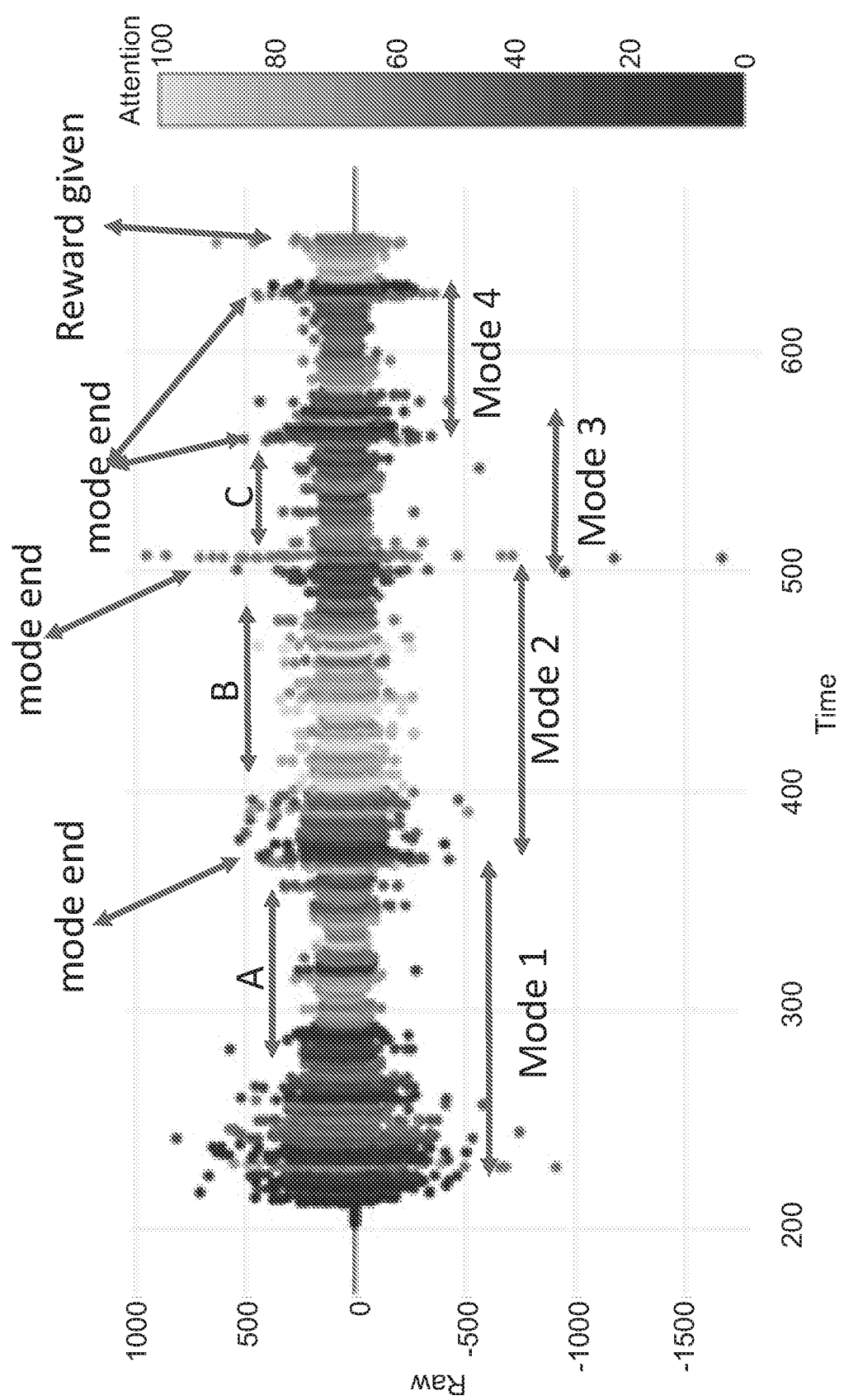
FIG. 12 shows an example plot of physiological measurements made using an EEG, according to the principles herein.

FIG. 12 shows an example plot of data from measurements collected using the lower-cost EEG biosensor, where the data is indicative of the attention of the individual as the individual performs computer-implemented multi-tasking tasks (including performing physical actions to provide responses to primary tasks in the presence of interference and in the absence of interference) during the various sessions of the cognitive platform. FIG. 12 shows the regions of the EEG attention measure that correspond to the intervals of time that the individual is interacting with the cognitive platform in each of the four modes (modes 1, 2, 3, and 4). The beginning and end of each mode is evidenced by the greater scatter of EEG signal data points indicating changes in attention. For example, the greater scatter of data points occurs at time points t=about 375 (end of mode 1), t=about 500 (end of mode 2), t=about 575 (end of mode 3), and about 625 (end of mode 4). The data points are also shown to scatter at the end of the modes when a reward is given to the individual after completion of the final mode (at t=about 650). At points during the interaction, the data points are seen to become less scattered (e.g., at regions A, B, and C), indicating a more stable level of attention being measured.

In a non-limiting example, the processing unit may use for the analysis only the data from measurements of the individual's performance of the tasks and/or interference made during the time intervals of the physiological measurement indicating more focused attention or higher user engagement (e.g., regions A, B, and C) to compute the performance metrics for the individual, such as but not limited to a decision boundary metric or the interference cost. In another non-limiting example, the processing unit may apply differing weighting factors to subsets the data from measurements of the individual's performance of the tasks and/or interference made during the time intervals of the physiological measurement indicating more focused attention or higher user engagement (e.g., regions A, B, and C) as compared to time intervals of less focused attention, prior to computing the performance metrics for the individual, such as but not limited to a decision boundary metric or the interference cost. In another non-limiting example, the processing unit can be configured to use physiological measurements indicating more focused attention or higher user engagement in a first trial or session to modify (adjust) time-varying characteristics or other characteristics of the tasks and/or interference in a subsequent trial or session, e.g., using one or more controllers to effect a feedback loop, such that physiological measurements from the individual in the subsequent trial or session indicates more focused attention or higher user engagement (e.g., longer time intervals of regions A, B, or C) of the individual during interaction with the tasks and/or interference. The physiological measurement indicative of more focused attention or higher user engagement may be collected either during a previous session of the individual's interaction with the tasks and/or interference or based on preset thresholds of aggregated physiological measurement data collected based on the interaction of two or more individuals (up to a group or population) with the task and/or interference.

Table 1 shows example EEG signal data from the EEG to the cognitive platform

TABLE 1

| Run No. | Time | .Raw Data |
|---|---|---|
| 1 | 213.5491 | −18 |
| 2 | 213.5824 | 113 |
| 3 | 213.6158 | .162 |
| 4 | 213.6491 | 121. |
| 5 | 213.6825 | −4 |
| 6 | 213.7157 | −4. |
| 7 | 213.7493 | −4 |

For each run, the following values of parameters were used or measured: Poor Signal=25; Attention=0; Meditation=0; Blink=0; Delta=433068; Theta=113711; Low-Alpha=20951; High-Alpha=10596; Low-Beta=5082; High-Beta=6601; Low-Gamma=3943; High-Gamma=5484; Stars=0

In another example, the physiological measurements can be used to indicate user physical movement and/or muscle isolation, such as but not limited to using an EEG. In this example, the measurement data indicating physical or muscle component of the EEG are separated from the measurement data indicative of brain-targeted measurements. In this example, the lower-cost EEG is integrated for brainwave and/or muscle trigger detection. In an example where the large physical component of the cognitive platform is steering/rotating a device (such as but not limited to a tablet), the platform product is configured to detect when these events are happening with the EEG.

Measurement data of user reaction time while interacting with the cognitive platform are also collected and the EEG measurement data is collected as the user is reacting to the triggers in the cognitive platform.

Figure 13:
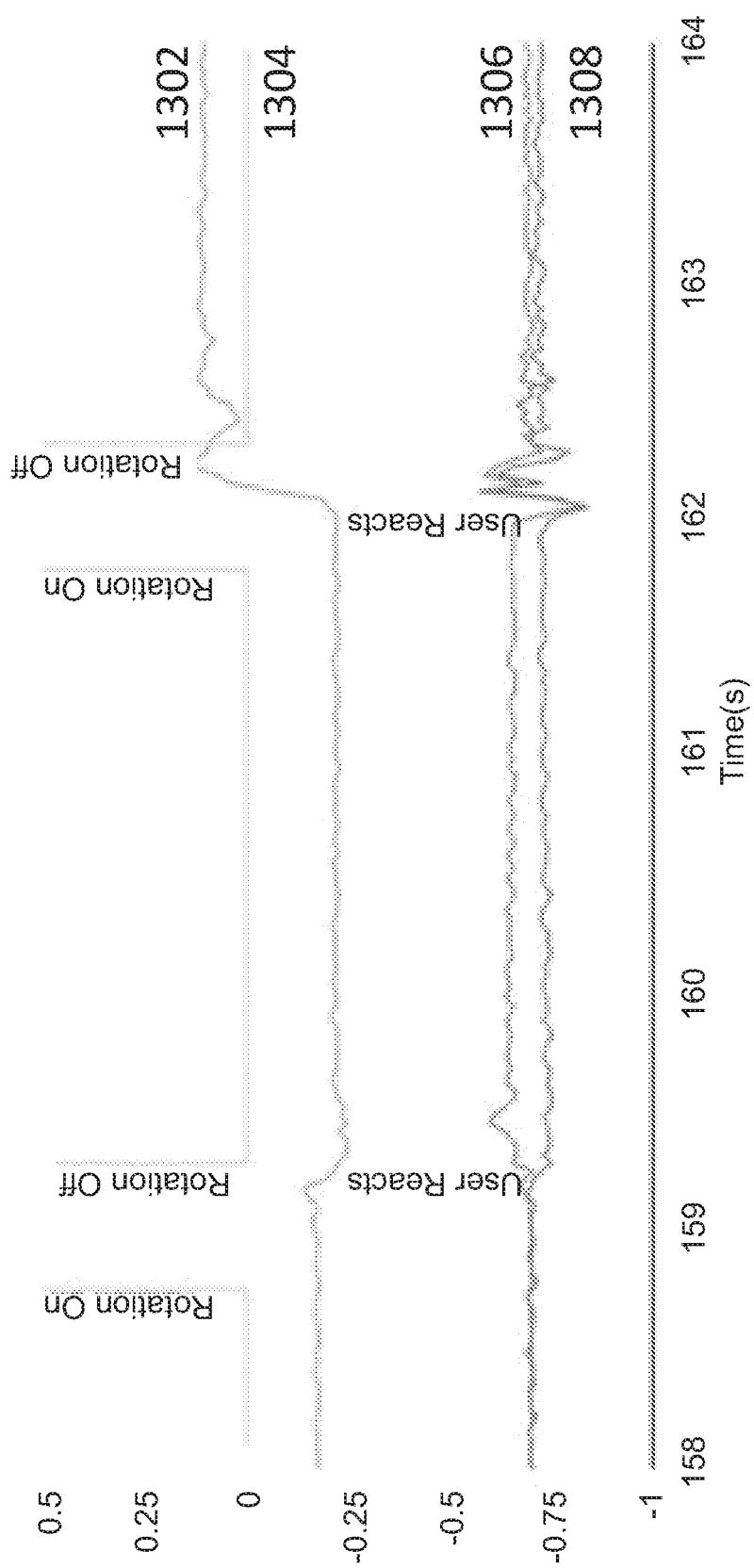
FIG. 13 shows an example plot of physiological measurements made using an EEG, according to the principles herein.

FIG. 13 shows non-limiting example EEG data from the measurements of muscle isolation as the individual performs physical actions. FIG. 13 shows plot of data from measurement of EEG signals for high alpha/Accx (1302), low alpha/TR (1304), low beta/Accy (1306), and high beta/AccZ (1308). The example data can be used to provide measures of individual's reaction time. The measurements allow the filtering of EEG signals related to physical activity from EEG signals related to brain wave activity. At t=about 158.5 and about 161.7, the label "rotation on" indicates the time point (relative to the EEG signals) where the computing device is instructing the individual (e.g., using a visual cue rendered to the user interface) to rotate the computing device. At t=about 159 and about 162.3, the label "rotation off" indicates the time point on the EEG signals where the computing device is instructing the individual to no longer rotate the computing device. At the points t=about 159.2 and t=about 162, the EEG signal change to indicate the points at which the individual reactions to perform the action (providing data indicative of the individual's reaction time).

In a non-limiting example implementation, measurements are made using a cognitive platform that is configured for coupling with a fMRI, for use for medical application validation and personalized medicine. Consumer-level fMRI devices may be used to improve the accuracy and the validity of medical applications by tracking and detecting changes in the level of stimulation in various regions of the brain.

In a non-limiting example use for treatment validation, the user interacts with a cognitive platform, and the fMRI is user to measure physiological data. The user is expected to have stimulation of a particular brain region or combination of brain regions based on the actions of the user while interacting with the cognitive platform. In this example, the platform product may be configured as an integrated device including the fMRI component coupled with the cognitive platform, or as a cognitive platform that is separate from, but configured for coupling with the fMRI component. Using the application with the fMRI, measurement can be made of the stimulation of portions of the user brain, and analysis can be performed to detect changes to determining whether the user is exhibit the desired responses.

In a non-limiting example use for personalized medicine, the fMRI can be used to collect measurement data to be used to identify the progress of the user in interacting with the cognitive platform. The analysis can be used to determine whether the cognitive platform should be caused to provide tasks and/or CSIs to enforce or diminish these user results that the fMRI is detecting, by adjusting users experience in the application.

In this example and any other example herein, the cData and/or nData can be collected in real-time.

In this example and any other example herein, the adjustments to the type of tasks and/or CSIs can be made in real-time.

Figure 14A:
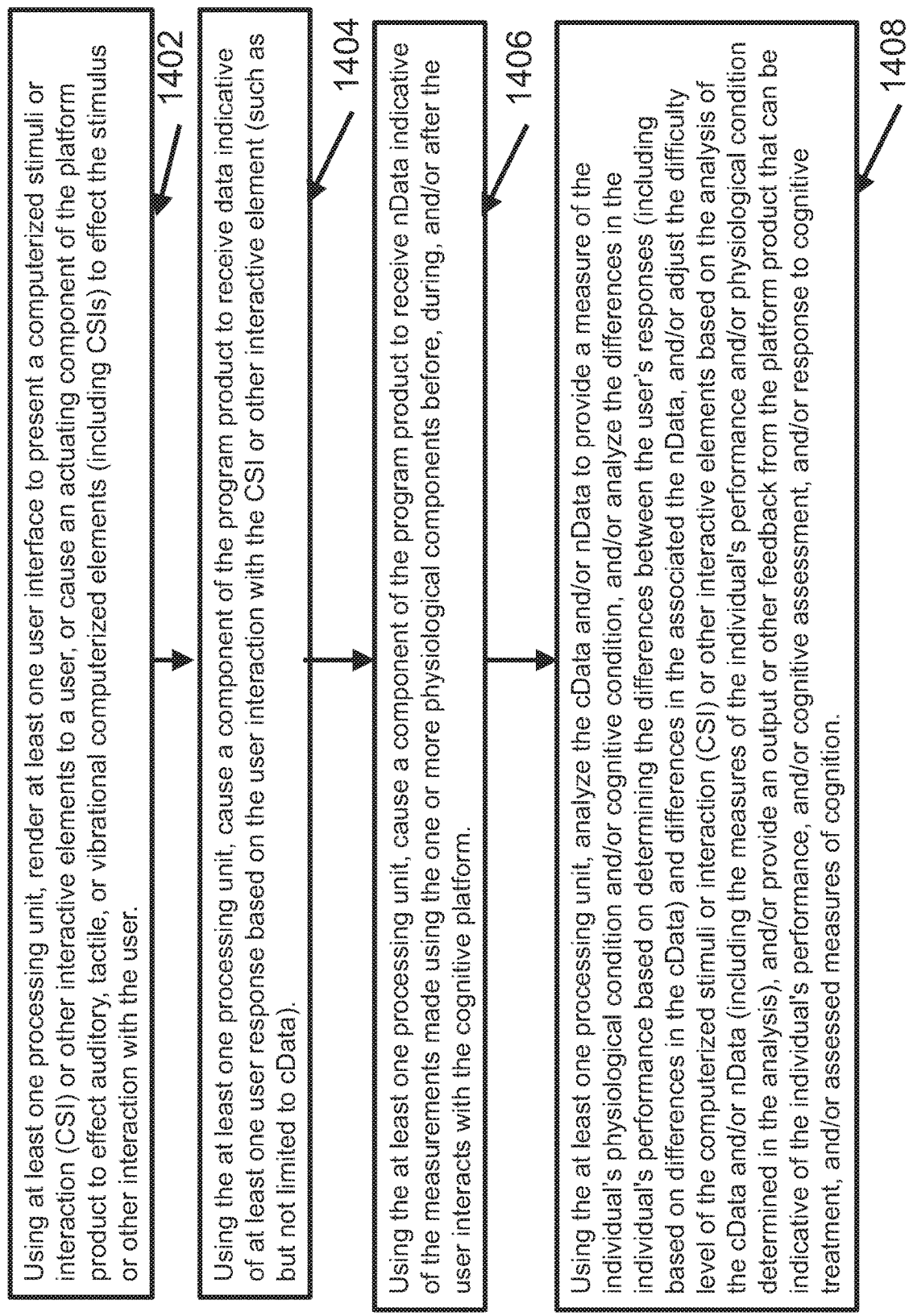
FIG. 14A-14C show flowcharts of example methods, according to the principles herein.

FIG. 14A shows a flowchart of a non-limiting example method that can be implemented using a platform product that includes at least one processing unit. In block 1402, the at least one processing unit is used to render at least one user interface to present a computerized stimuli or interaction (CSI) or other interactive elements to the user, or cause an actuating component of the platform product to effect auditory, tactile, or vibrational computerized elements (including CSIs) to effect the stimulus or other interaction with a user. In block 1404, the at least one processing unit is used to cause a component of the program product to receive data indicative of at least one user response based on the user interaction with the CSI or other interactive element (such as but not limited to cData). In an example where at least one user interface is rendered to present the computerized stimuli or interaction (CSI) or other interactive elements to the user, the at least one processing unit can be programmed to cause user interface to receive the data indicative of at least one user response. In block 1406, the at least one processing unit is used to cause a component of the program product to receive nData indicative of the measurements made using the one or more physiological components before, during, and/or after the user interacts with the cognitive platform. In block 1408, the at least one processing unit also is used to: analyze the cData and/or nData to provide a measure of the individual's physiological condition and/or cognitive condition, and/or analyze the differences in the individual's performance based on determining the differences between the user's responses (including based on differences in the cData) and differences in the associated the nData, and/or adjust the difficulty level of the computerized stimuli or interaction (CSI) or other interactive elements based on the analysis of the cData and/or nData (including the measures of the individual's performance and/or physiological condition determined in the analysis), and/or provide an output or other feedback from the platform product that can be indicative of the individual's performance, and/or cognitive assessment, and/or response to cognitive treatment, and/or assessed measures of cognition.

Figure 14B:
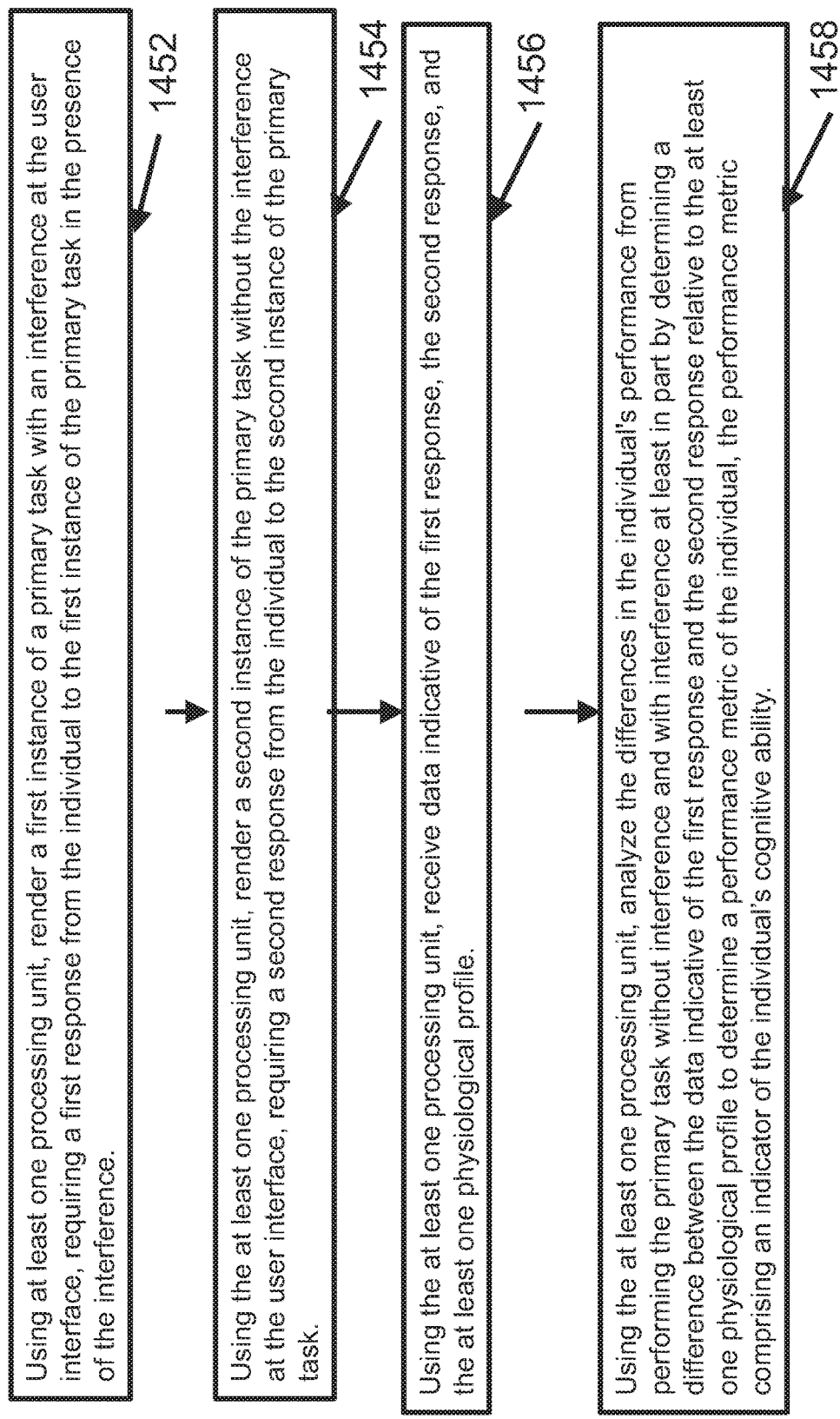

FIG. 14B shows a flowchart of a non-limiting example method that can be implemented using a platform product that includes at least one processing unit. In block 1452, the at least one processing unit is used to render a first instance of a primary task with an interference at the user interface, requiring a first response from the individual to the first instance of the primary task in the presence of the interference. In block 1454, the at least one processing unit is used to render a second instance of the primary task without the interference at the user interface, requiring a second response from the individual to the second instance of the primary task. In block 1456, the at least one processing unit is used to receive data indicative of the first response, the second response, and the at least one physiological profile. In block 1458, the at least one processing unit also is used to analyze the differences in the individual's performance from performing the primary task without interference and with interference at least in part by determining a difference between the data indicative of the first response and the second response relative to the at least one physiological profile to determine a performance metric of the individual, the performance metric comprising an indicator of the individual's cognitive ability.

Figure 14C:
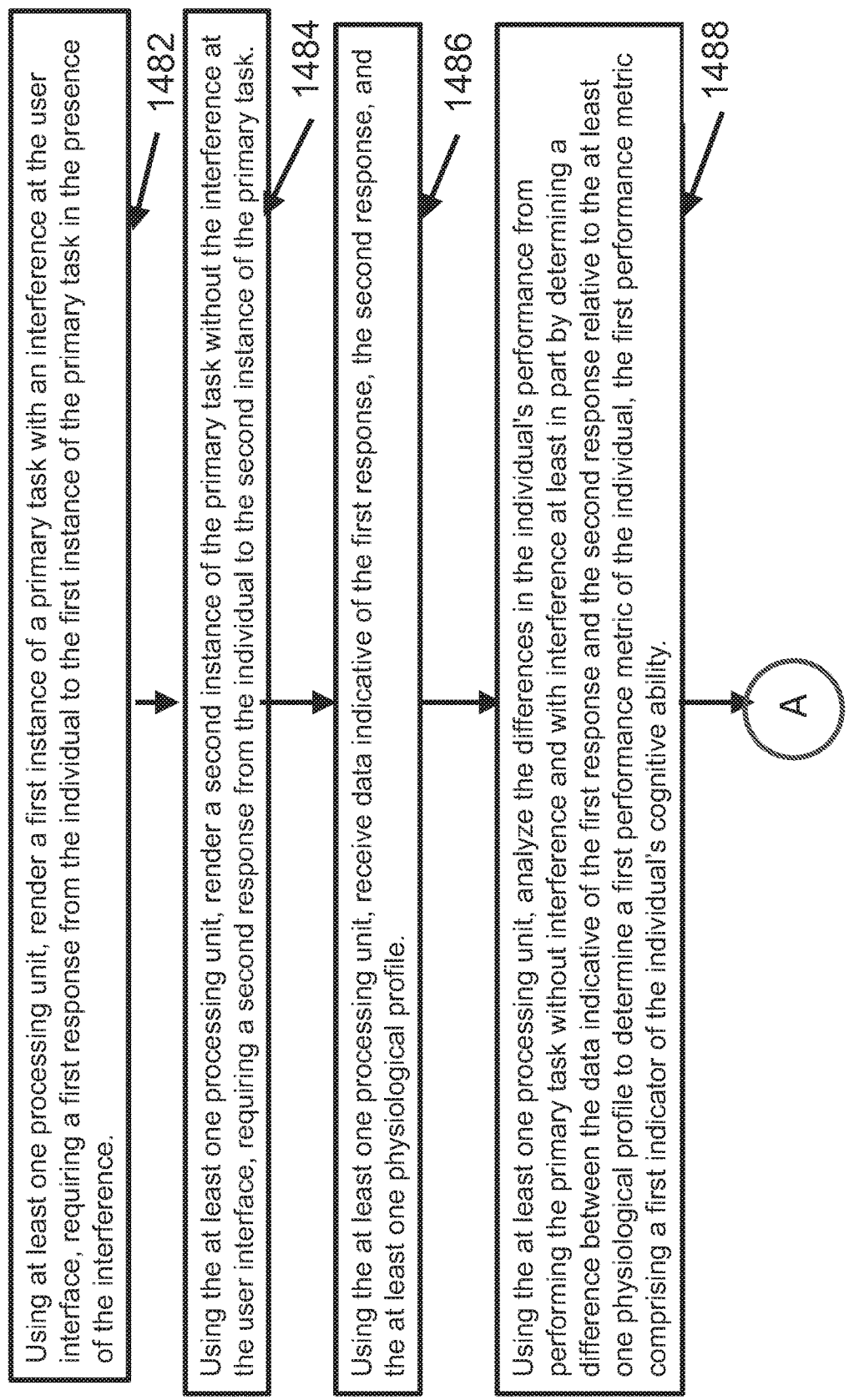
Figure 14C:
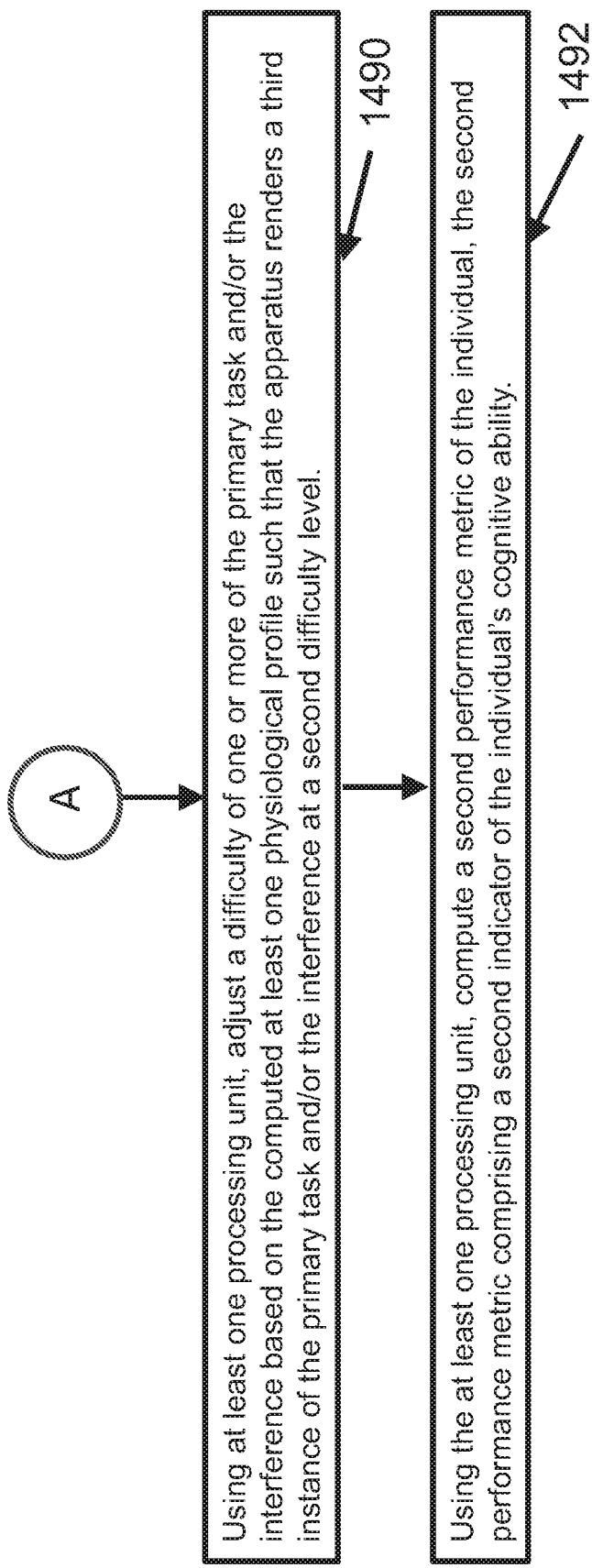

FIG. 14C shows a flowchart of a non-limiting example method that can be implemented using a platform product that includes at least one processing unit. In block 1482, the at least one processing unit is used to render a first instance of a primary task with an interference at the user interface, requiring a first response from the individual to the first instance of the primary task in the presence of the interference. In block 1484, the at least one processing unit is used to render a second instance of the primary task without the interference at the user interface, requiring a second response from the individual to the second instance of the primary task. In block 1486, the at least one processing unit is used to receive data indicative of the first response, the second response, and the at least one physiological profile. In block 1488, the at least one processing unit also is used to analyze the differences in the individual's performance from performing the primary task without interference and with interference at least in part by determining a difference between the data indicative of the first response and the second response relative to the at least one physiological profile to determine a first performance metric of the individual, the first performance metric comprising an indicator of the individual's cognitive ability. In block 1490, the at least one processing unit is used to adjust a difficulty of one or more of the primary task and/or the interference based on the computed at least one physiological profile such that the apparatus renders a third instance of the primary task and/or the interference at a second difficulty level. In block 1492, the at least one processing unit is used to compute a second performance metric of the individual, the second performance metric comprising a second indicator of the individual's cognitive ability.

In some examples, the results of the analysis may be used to modify the difficulty level or other property of the computerized stimuli or interaction (CSI) or other interactive elements.

Figure 15:
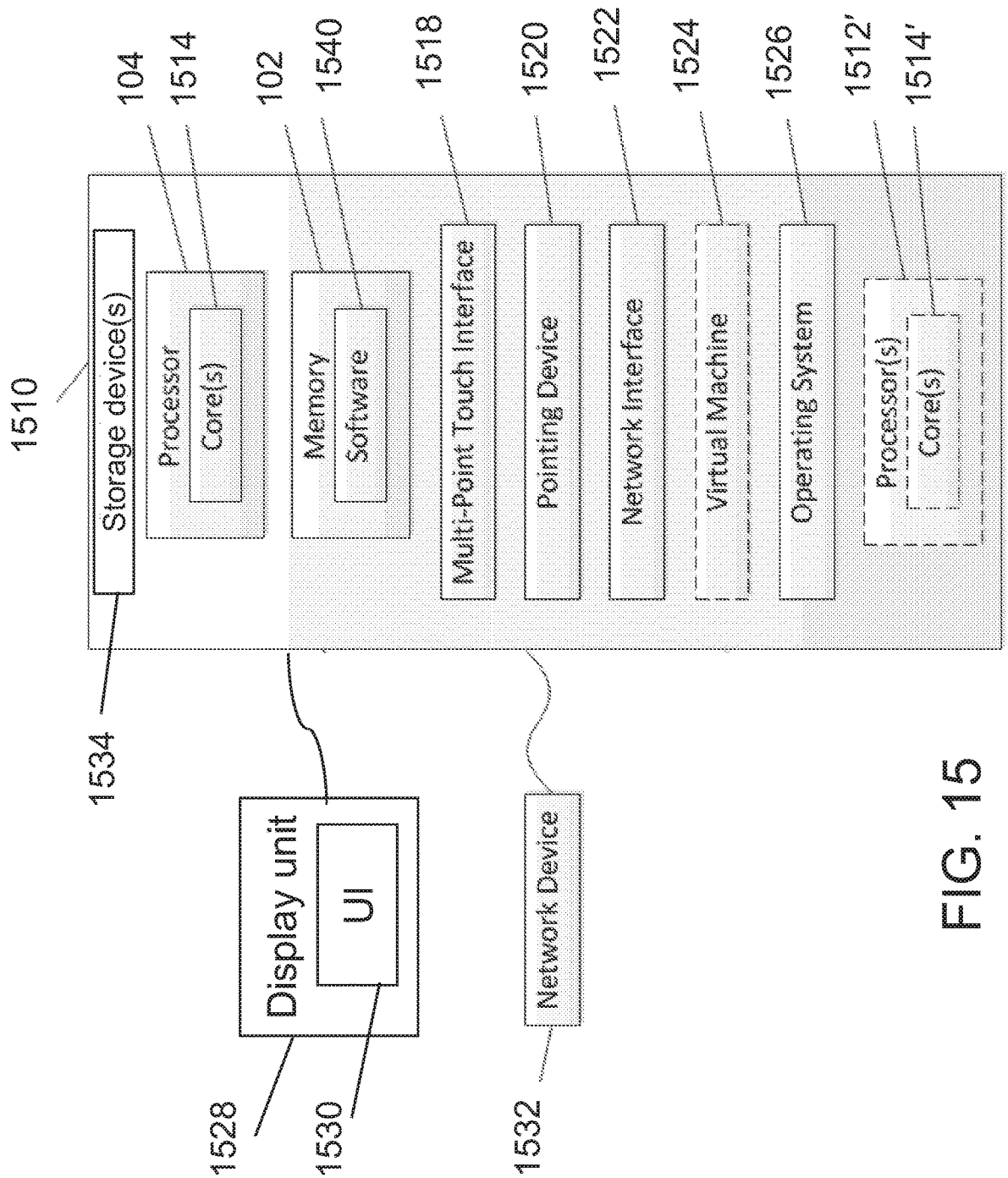
FIG. 15 shows a block diagram of an example computer system, according to the principles herein.

FIG. 15 is a block diagram of an example system (e.g., computer system) including a computing device 1510 that can be used as a computing component according to the principles herein. In any example herein, computing device 1510 can be configured as a console that receives user input to implement the computing component, including to apply the signal detection metrics in computer-implemented adaptive response-deadline procedures. For clarity, FIG. 15 also refers back to and provides greater detail regarding various elements of the example system of FIG. 1 and the example computing device of FIG. 2. The computing device 1510 can include one or more non-transitory computer-readable media for storing one or more computer-executable instructions or software for implementing examples. The non-transitory computer-readable media can include, but are not limited to, one or more types of hardware memory, non-transitory tangible media (for example, one or more magnetic storage disks, one or more optical disks, one or more flash drives), and the like. For example, memory 102 included in the computing device 1510 can store computer-readable and computer-executable instructions or software for performing the operations disclosed herein. For example, the memory 102 can store a software application 1540 which is configured to perform various of the disclosed operations (e.g., analyze cognitive platform measurement data, physiological component measurement data, and the response data to the tasks and/or interference, compute a performance metric (including an interference cost or a decision boundary metric), apply a signal detection metrics in adaptive response-deadline procedures, and/or performing other computation, as described herein). The computing device 1510 also includes configurable and/or programmable processor 104 and an associated core 1514, and optionally, one or more additional configurable and/or programmable processing devices, e.g., processor(s) 1512' and associated core(s) 1514' (for example, in the case of computational devices having multiple processors/cores), for executing computer-readable and computer-executable instructions or software stored in the memory 102 and other programs for controlling system hardware. Processor 104 and processor(s) 1512' can each be a single core processor or multiple core (1514 and 1514') processor.

Virtualization can be employed in the computing device 1510 so that infrastructure and resources in the console can be shared dynamically. A virtual machine 1524 can be provided to handle a process running on multiple processors so that the process appears to be using only one computing resource rather than multiple computing resources. Multiple virtual machines can also be used with one processor.

Memory 102 can include a computational device memory or random access memory, such as DRAM, SRAM, EDO RAM, and the like. Memory 102 can include other types of memory as well, or combinations thereof.

A user can interact with the computing device 1510 through a visual display unit 1528, such as a computer monitor, which can display one or more user interfaces 1530 that can be provided in accordance with example systems and methods. The computing device 1510 can include other I/O devices for receiving input from a user, for example, a keyboard or any suitable multi-point touch interface 1518, a pointing device 1520 (e.g., a mouse), a camera or other image recording device, a microphone or other sound recording device, an accelerometer, a gyroscope, a sensor for tactile, vibrational, or auditory signal, and/or at least one actuator. The multi-point touch interface 1518 and the pointing device 1520 can be coupled to the visual display unit 1528. The computing device 1510 can include other suitable conventional I/O peripherals.

The computing device 1510 can also include one or more storage devices 1534, such as a hard-drive, CD-ROM, or other computer readable media, for storing data and computer-readable instructions and/or software that perform operations disclosed herein. Example storage device 1534 can also store one or more databases for storing any suitable information required to implement example systems and methods. The databases can be updated manually or automatically at any suitable time to add, delete, and/or update one or more items in the databases.

The computing device 1510 can include a network interface 1522 configured to interface via one or more network devices 1532 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 1522 can include a built-in network adapter, network interface card, PCMCIA network card, card bus network adapter, wireless network adapter, USB network adapter, modem or any other device suitable for interfacing the computing device 1510 to any type of network capable of communication and performing the operations described herein. Moreover, the computing device 1510 can be any computational device, such as a workstation, desktop computer, server, laptop, handheld computer, tablet computer, or other form of computing or telecommunications device that is capable of communication and that has sufficient processor power and memory capacity to perform the operations described herein.

The computing device 1510 can run any operating system 1526, such as any of the versions of the Microsoft® Windows® operating systems, iOS® operating system, Android™ operating system, the different releases of the Unix and Linux operating systems, any version of the MacOS® for Macintosh computers, any embedded operating system, any real-time operating system, any open source operating system, any proprietary operating system, or any other operating system capable of running on the console and performing the operations described herein. In some examples, the operating system 1526 can be run in native mode or emulated mode. In an example, the operating system 1526 can be run on one or more cloud machine instances.

Examples of the systems, methods and operations described herein can be implemented in digital electronic circuitry, or in computer software, firmware, or hardware, including the structures disclosed in this specification and their structural equivalents, or in combinations of one or more thereof. Examples of the systems, methods and operations described herein can be implemented as one or more computer programs, i.e., one or more modules of computer program instructions, encoded on computer storage medium for execution by, or to control the operation of, data processing apparatus. The program instructions can be encoded on an artificially generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" or "computing device" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer program (also known as a program, software, software application, script, application or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing on one or more computer programs to perform actions by operating on input data and generating output. The processes and logic flows can also be performed by, and apparatuses can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), for example. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, for displaying information to the user and a keyboard and a pointing device, e.g., a mouse, a stylus, touch screen or a trackball, by which the user can provide input to the computer. Other kinds of devices can be used to provide for interaction with a user as well. For example, feedback (i.e., output) provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

In some examples, a system, method or operation herein can be implemented in a computing system that includes a back end component, e.g., as a data server, or that includes a middleware component, e.g., an application server, or that includes a front end component, e.g., a client computer having a user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Example computing system 400 can include clients and servers. A client and server are generally remote from each other and typically interact through a communication network. The relationship of client and server arises by virtue of computer programs running on the respective computers and having a client-server relationship to each other. In some embodiments, a server transmits data to a client device (e.g., for purposes of displaying data to and receiving user input from a user interacting with the client device). Data generated at the client device (e.g., a result of the user interaction) can be received from the client device at the server.

CONCLUSION

The above-described embodiments can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An apparatus for generating a quantifier of cognitive skills in an individual, said apparatus being coupled to at least one physiological component, the apparatus comprising:

a user interface comprising a display and an input device;
a memory to store processor-executable instructions; and a processing unit communicatively coupled to the user interface and the memory, wherein upon execution of the processor-executable instructions by the processing unit, the processing unit is configured to:

render a first instance of a primary task with an interference at a graphical user interface being displayed at the display of the user interface, wherein the primary task comprises one or more first computerized stimuli or interaction comprising one or more graphical objects configured to prompt a first response from the individual to the first instance of the primary task in the presence of the interference via the input device of the user interface, wherein the primary task comprises a time-varying task having a response deadline;

wherein the interference comprises one or both of an interruptor or a distraction, wherein the interruptor or the distraction comprises one or more additional graphical objects configured to divert the individual's attention from performing the primary task;

render a second instance of the primary task without the interference at the user interface, wherein the second instance of the primary task without the interference is configured to require a second response from the individual to the second instance of the primary task;

wherein the processing unit is configured to:
(i) receive a secondary response to the interference at substantially the same time as the processing unit receives the second response; or
(ii) receive the secondary response to the interference that is an interruptor at substantially the same time as the processing unit receives the first response and not receive the secondary response to the interference that is a distraction at substantially the same time that the processing unit receives the first response; and wherein the processing unit is configured to receive data indicative of at least one physiological profile of the individual, the physiological profile being based on one or more measurements of the at least one physiological component, the at least one physiological component being coupled to measure a physiological measurement of the individual;

receive data indicative of the first response, the second response, and the at least one physiological profile;

analyze the differences in the individual's performance from performing the primary task without interference and with interference at least in part by determining a difference between the data indicative of the first response and the data indicative of the second response relative to the at least one physiological profile to determine a performance metric of the individual, the performance metric comprising an indicator of the cognitive ability of the individual; and modify a time-varying aspect of one or both of the primary task or the interference in response to the performance metric, wherein modifying the time-varying aspect of one or both of the primary task or the interference comprises modifying one or more of a speed of an object, a rate of change of a facial expression, a direction of trajectory of an object, a change of orientation of an object, at least one color of an object, a type of an object, or a size of an object.

2. The apparatus of claim 1, wherein the processing unit is further configured to send a control signal to the at least one physiological component to perform the one or more measurements.

3. The apparatus of claim 1, wherein the physiological profile provides an indication of a state of attentiveness of the individual to the primary task and/or the interference.

4. The apparatus of claim 1, wherein the processing unit is further configured to:
identify physiological profiles indicative of one or both of a state of anger or a state of frustration of the individual; and
adjust a difficulty of one or both of the primary task or the interference to normalize such that a subsequently computed at least one physiological profile is indicative of a modification of the state of anger or the state of frustration of the individual.

5. The apparatus of claim 1, wherein the processing unit is further configured to analyze the at least one physiological profile to determine whether a user is likely to respond or not to respond to a treatment.

6. The apparatus of claim 1, wherein the processing unit is further configured to:
adjust a difficulty of one or both of the primary task or the interference to normalize such that a subsequently computed at least one physiological profile is indicative of an emotionally-regulated state of the individual.

7. The apparatus of claim 1, wherein the processing unit is further configured to compute the performance metric as an interference cost.

8. The apparatus of claim 1, further comprising at least one actuating component, wherein the processing unit is further configured to control the actuating component to effect one or both of the primary task or the interference as comprising one or more of an auditory stimulus, a tactile stimulus, or a vibrational stimulus.

9. The apparatus of claim 1, wherein the performance metric comprises data indicative of one or both of: (i) a projected performance of the individual at one or both of a cognitive test or a behavioral test, and (ii) a diagnosis of a status or progression of a cognitive condition, a disease or an executive function disorder of the individual.

10. The apparatus of claim 1, wherein the processing unit is further configured to use the performance metric to perform at least one of (i) changing one or more of an amount, concentration, or dose titration of a pharmaceutical agent, drug, or biologic, (ii) identifying a likelihood of the individual experiencing an adverse event in response to administration of the pharmaceutical agent, drug, or biologic, (iii) identifying a change in the individual's cognitive abilities, (iv) recommending a treatment regimen, or (v) recommending or determining a degree of effectiveness of at least one of a behavioral therapy, counseling, or physical exercise.

11. The apparatus of claim 1, wherein the processing unit is configured to control the user interface to render the first instance of one or both of the primary task or the interference as a continuous visuo-motor tracking task, and wherein the first instance of the primary task or the interference is a first time interval of the continuous visuo-motor task.

12. The apparatus of claim 1, wherein the processing unit is configured to control the user interface to render one or both of the primary task or the interference as a target discrimination interference.

13. The apparatus of claim 1, wherein the processing unit is configured to render the first instance of the primary task with the interference by configuring the user interface to:
render the first instance of the primary task in the presence of the interference such that the interference diverts the individual's attention from the primary task, in which the interference is rendered as one or both of a distraction or an interruptor.

14. The apparatus of claim 1, wherein the processing unit is further configured to render a predictive model based on the determined performance metric, to generate a predictive model output indicative of a measure of one or more of a cognition, a mood, a level of cognitive bias, attentiveness, user engagement, or an affective bias of the individual.

15. The apparatus of claim 1, wherein the determined performance metric comprises an indicator of a projected response of the individual to a cognitive treatment being or to be delivered.

16. The apparatus of claim 1, wherein the processing unit is further configured to transmit control signals to one or more of a controller to implement a feedback loop based on the one or more measurements of the at least one physiological component.

17. A system comprising one or more physiological components and an apparatus of claim 1, wherein upon execution of the processor-executable instructions by the processing unit, the processing unit is configured to:
receive data indicative of one or more measurements of the physiological component; and
analyze the data indicative of the first response and the second response, and the data indicative of the one or more measurements of the physiological component to compute the performance metric.

18. The apparatus of claim 1, wherein the processing unit is configured to control at least one sensing device to measure at least one physical action of the individual to provide one or both of the first response or the second response, and (ii) the sensing device comprises one or more of a gyroscope, an accelerometer, a motion sensor, a position sensor, a pressure sensor, an optical sensor, an auditory sensor, a vibrational sensor, a video camera, a pressure-sensitive surface, or a touch-sensitive surface.

19. The apparatus of claim 1, wherein the at least one physiological component comprises one or more of a electroencephalogram, magnetoencephalography, electrocardiograph, heart rate monitor, heart rate variability monitor, blood pressure monitor, event-related potential (ERP) monitor, functional magnetic resonance imaging (fMRI), skin electrical potential measurement device, galvanic skin response (GSR), eye-tracking device, optical detection device, functional near-infrared spectroscopy (fNIRS), or positron emissiontomography (PET).

20. An apparatus for enhancing cognitive skills in an individual, said apparatus comprising:
a user interface comprising a display and an input device;
a memory to store processor-executable instructions; and
a processing unit communicatively coupled to the user interface and the memory, wherein upon execution of the processor-executable instructions by the processing unit, the processing unit is configured to:
render a first instance of a primary task with an interference at a graphical user interface being displayed at the display of the user interface, wherein the primary task comprises one or more first computerized stimuli or interaction comprising one or more graphical objects configured to prompt a first response from the individual to the first instance of the primary task in the presence of the interference via the input device of the user interface, wherein the primary task comprises a time-varying task having a response deadline;
wherein the interference comprises one or both of an interruptor or a distraction wherein the interruptor or the distraction comprises one or more additional graphical objects configured to divert the individual's attention from performing the primary task;
render a second instance of the primary task without the interference at the user interface, wherein the second instance of the primary task without the interference is configured to require a second response from the individual to the second instance of the primary task;
wherein the processing unit is configured to:
(i) receive a secondary response to the interference at substantially the same time as the processing unit receives the second response; or
(ii) receive the secondary response to the interference that is an interruptor at substantially the same time as the processing unit receives the first response and not receive the secondary response to the interference that is a distraction at substantially the same time that the processing unit receives the first response; and
wherein the processing unit is configured to receive data indicative of at least one physiological profile of the individual, the physiological profile being based on one or more measurements of at least one physiological component to provide a physiological measurement, the at least one physiological component being coupled to measure a physiological measurement of the individual;
receive data indicative of the first response, the second response, and the at least one physiological profile;
analyze the differences in the individual's performance from performing the primary task without interference and with interference at least in part by determining a difference between the data indicative of the first response and the data indicative of the second response relative to the at least one physiological profile to determine a first performance metric of the individual, the first performance metric comprising a first indicator of a cognitive ability of the individual;
adjust a difficulty of one or both of the primary task or the interference based on the at least one physiological profile such that the apparatus renders one or both of a third instance of the primary task or the interference at a second difficulty level; and
determine a second performance metric of the individual, the second performance metric comprising a second indicator of the cognitive ability of the individual,
wherein adjusting the difficulty of one or both of the primary task or the interference comprises modifying a time-varying aspect of one or both of the primary task or the interference in response to one or both of the first performance metric and the second performance metric,
wherein modifying the time-varying aspect of one or both of the primary task or the interference comprises modifying one or more of a speed of an object, a rate of change of a facial expression, a direction of trajectory of an object, a change of orientation of an object, at least one color of an object, a type of an object, or a size of an object.

21. The apparatus of claim 20, wherein the processing unit is further configured to send a control signal to the at least one physiological component to perform the one or more measurements.

22. The apparatus of claim 20, wherein the processing unit is further configured to send a control signal to one or more controllers, to adjust the difficulty of one or both of the primary task or the interference based on a feedback loop.

23. The apparatus of claim 20, wherein the processing unit is further configured to adjust, based on the first performance metric, one or both of at least one user instruction to the individual rendered to the user interface or at least one reward rendered to the user interface.

24. The apparatus of claim 20, wherein the processing unit is further configured to adjust the difficulty of one or both of the primary task or the interference such that the at least one physiological profile is indicative of at least one of (i) a state of attentiveness of the individual to one or both of the primary task or the interference, or (ii) increased engagement of the individual to one or both of the primary task or the interference.

25. The apparatus of claim 20, wherein the processing unit is further configured to adjust the difficulty of one or both of the primary task or the interference in response to the at least one physiological profile indicating task automation.

26. The apparatus of claim 20, wherein the processing unit is further configured to render the first instance of the primary task and the second instance of the primary task to obtain the first and second responses in an iterative manner, with the difficulty being adjusted between two or more of the iterations.

27. The apparatus of claim 20, further comprising at least one actuating component, wherein the processing unit is further configured to control the actuating component to effect one or both of the primary task or the interference as comprising one or more of an auditory stimulus, a tactile stimulus, and a vibrational stimulus.

28. The apparatus of claim 20, wherein the processing unit is configured to control the user interface to render the first instance of the primary task as a continuous visuo-motor tracking task, and wherein the first instance of the primary task is a first time interval of the continuous visuo-motor task.

29. The apparatus of claim 20, wherein (i) the processing unit is configured to control at least one sensing device to measure at least one physical action of the individual to provide one or both of the first response or the second response, and (ii) the sensing device comprises one or more of a gyroscope, an accelerometer, a motion sensor, a position sensor, a pressure sensor, an optical sensor, an auditory sensor, a vibrational sensor, a video camera, a pressure-sensitive surface, or a touch-sensitive surface.

30. The apparatus of claim 20, wherein the at least one physiological component comprises one or more of a electroencephalogram, magnetoencephalography, electrocardiograph, heart rate monitor, heart rate variability monitor, blood pressure monitor, event-related potential (ERP) monitor, functional magnetic resonance imaging (fMRI), skin electrical potential measurement device, galvanic skin response (GSR), eye-tracking device, optical detection device, functional near-infrared spectroscopy (fNIRS), or positron emission tomography (PET).

31. The apparatus of claim 20, wherein one or both of the primary task or interference comprises a targeting task.

32. The apparatus of claim 20, wherein the adjusting the difficulty comprises modifying a time-varying aspect of one or both of the primary task or the interference.

33. A system comprising the at least one physiological component and the apparatus of claim 20, wherein upon execution of the processor-executable instructions by the processing unit, the processing unit is configured to:
  receive data indicative of one or more measurements of the at least one physiological component; and
  analyze the data indicative of the first response and the second response, and the data indicative of the one or more measurements of the at least one physiological component to compute the performance metric.

* * * * *